United States Patent
Krainc et al.

(10) Patent No.: US 10,442,812 B2
(45) Date of Patent: *Oct. 15, 2019

(54) SUBSTITUTED 4-METHYL-PYRROLO[1,2-A]PYRIMIDINE-8-CARBOXAMIDE COMPOUNDS AND USES THEREOF FOR MODULATING GLUCOCEREBROSIDASE ACTIVITY

(71) Applicant: Northwestern University, Evanston, IL (US)

(72) Inventors: Dimitri Krainc, Chicago, IL (US); Richard B. Silverman, Winnetka, IL (US); Jianbin Zheng, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/252,053

(22) Filed: Jan. 18, 2019

(65) Prior Publication Data

US 2019/0152980 A1 May 23, 2019

Related U.S. Application Data

(63) Continuation of application No. 16/021,972, filed on Jun. 28, 2018, now Pat. No. 10,227,352, which is a continuation of application No. 15/789,645, filed on Oct. 20, 2017, now Pat. No. 10,040,799, which is a continuation of application No. 15/199,220, filed on Jun. 30, 2016, now Pat. No. 9,802,942.

(60) Provisional application No. 62/187,463, filed on Jul. 1, 2015.

(51) Int. Cl.
| | |
|---|---|
| C07D 487/04 | (2006.01) |
| A61K 9/48 | (2006.01) |
| A61K 9/12 | (2006.01) |
| A61K 9/20 | (2006.01) |
| A61K 9/02 | (2006.01) |
| A61K 9/10 | (2006.01) |
| A61K 9/00 | (2006.01) |
| A61K 38/46 | (2006.01) |
| C09B 11/24 | (2006.01) |
| A61K 31/519 | (2006.01) |
| A61K 31/5377 | (2006.01) |
| C07D 519/00 | (2006.01) |
| C12N 9/24 | (2006.01) |
| A61K 45/06 | (2006.01) |
| A61K 31/5355 | (2006.01) |
| A61K 47/26 | (2006.01) |
| A61K 47/38 | (2006.01) |
| A61P 25/16 | (2006.01) |
| A61P 25/28 | (2006.01) |

(52) U.S. Cl.
CPC ............ *C07D 487/04* (2013.01); *A61K 9/008* (2013.01); *A61K 9/0019* (2013.01); *A61K 9/02* (2013.01); *A61K 9/10* (2013.01); *A61K 9/12* (2013.01); *A61K 9/20* (2013.01); *A61K 9/2054* (2013.01); *A61K 9/2059* (2013.01); *A61K 9/48* (2013.01); *A61K 9/4866* (2013.01); *A61K 31/519* (2013.01); *A61K 31/5355* (2013.01); *A61K 31/5377* (2013.01); *A61K 38/465* (2013.01); *A61K 45/06* (2013.01); *A61K 47/26* (2013.01); *A61K 47/38* (2013.01); *A61P 25/16* (2018.01); *A61P 25/28* (2018.01); *C07D 519/00* (2013.01); *C09B 11/24* (2013.01); *C12N 9/2402* (2013.01); *C12Y 302/01045* (2013.01); *G01N 2800/28* (2013.01)

(58) Field of Classification Search
CPC .................................................... C07D 487/04
USPC ........................................................ 424/94.3
See application file for complete search history.

(56) References Cited

U.S. PATENT DOCUMENTS

| | | | |
|---|---|---|---|
| 8,431,593 B2 | 4/2013 | Hutchison et al. | |
| 9,802,842 B2 | 10/2017 | Krainc | |
| 9,802,942 B2 * | 10/2017 | Krainc | C07D 487/04 |
| 10,040,799 B2 * | 8/2018 | Krainc | C07D 487/04 |
| 2018/0185368 A1 * | 7/2018 | Skerlj | C07D 519/00 |

FOREIGN PATENT DOCUMENTS

| | | |
|---|---|---|
| AW | 2017161137 A1 | 9/2017 |
| WO | 2005066142 A2 | 7/2005 |
| WO | 2012078855 A1 | 6/2012 |
| WO | 2012129084 A2 | 9/2012 |
| WO | 2016073891 A1 | 5/2016 |
| WO | 2017161137 A1 | 9/2017 |
| WO | 2017176962 A1 | 10/2017 |
| WO | 2017192841 A1 | 11/2017 |

OTHER PUBLICATIONS

Angelini et al., "Enzyme replacement therapy for Pompe disease." Curr Neurol Neurosci Rep, 2012, 12(1):70-75.

(Continued)

*Primary Examiner* — Kahsay Habte
(74) *Attorney, Agent, or Firm* — Quarles & Brady LLP; M. Scott McBride

(57) ABSTRACT

Disclosed are new small molecules having a 4-methylpyrrolo[1,2-a]pyrimidine-8-carboxamide core structure and the uses thereof for modulating glucocerebrosidase activity. Also disclosed are pharmaceutical compositions comprising the small molecules which may be administered in methods of treating diseases or disorders associated with glucocerebrosidase activity, including neurological diseases and disorders such as Gaucher's disease and Parkinson's disease. The small molecules may contain a fluorophore or may be conjugated to a fluorophore in order to prepare a fluorescent probe for use in high throughput screening methods to identify new modulators of glucocerebrosidase activity via fluorescence polarization.

20 Claims, 7 Drawing Sheets

(56) References Cited

OTHER PUBLICATIONS

Atrian et al., "An evolutionary and structure-based docking model for glucocerebrosidase-saposin C and glucocerebrosidase-substrate interactions—relevance for Gaucher disease." Proteins, 2008, 70(3):882-891.
Bennett et al., "Gaucher disease and its treatment options." Ann Pharmacother, 2013, 47(9):1182-1193.
Brumshtein et al. "Characterization of gene-activated human acid-beta-glucosidase: crystal structure, glycan composition, and internalization into macrophages." Glycobiology, 2010, 20(1):24-32.
Choi et al., "Chemoselective small molecules that covalently modify one lysine in a non-enzyme protein in plasma." Nature Chemical Biology, 2010, 6(2):133-139.
Desnick et al. "Enzyme replacement therapy for lysosomal diseases: lessons from 20 years of experience and remaining challenges." Annu Rev Genomics Hum Genet, 2012, 13:307-335.
Futerman et al., "New directions in the treatment of Gaucher disease." Trends in Pharmacological Sciences, 2004, 25(3):147-151.
Futerman et al., "The cell biology of lysosomal storage disorders." Nat Rev Mol Cell Biol, 2004, 5(7):554-565.
Grabowski, "Phenotype, diagnosis, and treatment of Gaucher's disease." Lancet, 2008, 372(9645):1263-1271.
Lin et al., "Genetics and genomics of Parkinson's disease." Genome Medicine 6, 2014.
Mazzulli et al., "Gaucher disease glucocerebrosidase and alpha-synuclein form a bidirectional pathogenic loop in synucleinopathies." Cell, 2011, 146(1):37-52.
Motabar et al., "A high throughput glucocerebrosidase assay using the natural substrate glucosylceramide." Anal Bioanal Chem, 2012, 402(2):731-739.
Nakamura et al., "Covalent modification of lysine residues by allyl isothiocyanate in physiological conditions: plausible transformation of isothiocyanate from thiol to amine." Chem Res Toxicol, 2009, 22(3):536-542.
Nanda et al., "Labeling a Protein with Fluorophores Using NHS Ester Derivitization." Laboratory Methods in Enzymology: Protein Pt A, 2014, 536:87-94.
Patnaik et al., "Discovery, structure-activity relationship, and biological evaluation of noninhibitory small molecule chaperones of glucocerebrosidase." J Med Chem, 2012, 55(12):5734-5748.
Pisani et al., "Enzyme replacement therapy in patients with Fabry disease: state of the art and review of the literature." Mol Genet Metab, 2012, 107(3):267-275.
Rossi et al., "Analysis of protein-ligand interactions by fluorescence polarization." Nat Protoc, 2011, 6(3):365-387.
Sardi et al., "Augmenting CNS glucocerebrosidase activity as a therapeutic strategy for parkinsonism and other Gaucher-related synucleinopathies." Proceedings of the National Academy of Sciences of the United States of America, 2013, 110(9):3537-3542.
Schapira et al., "Slowing of neurodegeneration in Parkinson's disease and Huntington's disease: future therapeutic perspectives." Lancet, 2014, 384(9942):545-555.
Sidransky et al., "The link between the GBA gene and parkinsonism." Lancet Neurology, 2012, 11(11):986-998.
Sidransky et al., "Multicenter analysis of glucocerebrosidase mutations in Parkinson's disease." N Engl J Med, 2009, 361(17):1651-1661.
Souza et al., "Study of enzyme replacement therapy for Gaucher Disease: comparative analysis of clinical and laboratory parameters at diagnosis and after two, five and ten years of treatment." Rev Bras Hematol Hemoter, 2014, 36(5):345-350.
Sybertz et al., "Development of targeted therapies for Parkinson's disease and related synucleinopathies." J Lipid Res, 2014, 55(10):1996-2003.
Tamargo et al., "The role of saposin C in Gaucher disease." Mol Genet Metab, 2012, 106(3):257-263.
Tekoah et al., "Glycosylation and functionality of recombinant beta-glucocerebrosidase from various production systems." Bioscience Reports, 2013, 33:771-U272.
Toja et al., "Pyrrolopyridine Analogs of Nalidixic-Acid .1. Pyrrolo[2,3-B]Pyridines." Journal of Heterocyclic Chemistry, 1986, 23(5):1555-1560.
Valayannopoulos, "Enzyme replacement therapy and substrate reduction therapy in lysosomal storage disorders with neurological expression." Handb Clin Neurol, 2013, 113:1851-1857.
Vitner et al., "RIPK3 as a potential therapeutic target for Gaucher's disease." Nature Medicine, 2014, 20(2):204-208.
Weinreb et al., "Long-term clinical outcomes in type 1 Gaucher disease following 10 years of imiglucerase treatment." J Inherit Metab Dis, 2013, 36(3):543-553.
Zheng et al., "Three classes of glucocerebrosidase inhibitors identified by quantitative high-throughput screening are chaperone leads for Gaucher disease." Proc Natl Acad Sci USA, 2007, 104(32):13192-13197.
European Search Report for EP16818813 dated Nov. 22, 2018.
International Search Report for PCT/US2016/040471 dated Oct. 6, 2016.
Written Opinion for PCT/US2016/040471 dated Oct. 6, 2016.

\* cited by examiner

SUBSTITUTED 4-METHYL-PYRROLO[1,2-A]PYRIMIDINE-8-CARBOXAMIDE COMPOUNDS AND USES THEREOF FOR MODULATING GLUCOCEREBROSIDASE ACTIVITY

CROSS-REFERENCE TO RELATED PATENT APPLICATIONS

The present application is a continuation application of U.S. application Ser. No. 16/021,972, filed on Jun. 28, 2018, and published as U.S. Publication No. 2018/0305367, on Oct. 25, 2018, which is a continuation application of U.S. application Ser. No. 15/789,645, filed on Oct. 20, 2017, published as U.S. Publication No. 2018/0037586, on Feb. 8, 2018, and issued as U.S. Pat. No. 10,040,799, on Aug. 7, 2018, which application is a continuation application of U.S. application Ser. No. 15/199,220, filed on Jun. 30, 2016, published as U.S. Publication No. 2017/0002013, on Jan. 5, 2017, and issued as U.S. Pat. No. 9,802,942, on Oct. 31, 2017, which application claims the benefit of priority under 35 U.S.C. § 119(e) to U.S. Provisional Patent Application No. 62/187,463, filed on Jul. 1, 2015, the contents of which applications are incorporated herein by reference in their entireties.

BACKGROUND

The field of the invention relates to new small molecules and uses of the new small molecules for modulating glucocerebrosidase activity. The new small molecules have a substituted 4-methylpyrrrolo[1,2-a]pyrimidine-8-carboxamide core structure, such as a 2,4-dimethylpyrrrolo[1,2-a]pyrimidine-8-carboxamide core structure, and the small molecules may be administered to treat diseases and disorders associated with aberrant glucocerebrosidase acitivity including neurodegenerative diseases, such as Gaucher's disease and Parkinson's disease.

Glucocerebrosidase (EC 3.2.1.45), which also is called β-glucocerebrosidase, β-glucosidase, D-glucosyl-N-acylsphingosine glucohydrolase, or GCase, is an enzyme having glucosylceramidase activity. Glucocerebrosidase is required to cleave the beta-glucosidic linkage of the chemical glucocerebroside, which is an intermediate in glycolipid metabolism. Glucocerebrosidase is localized in the lysosome and disabling mutations in the gene for glucocerebrosidase (GBA1) are associated with abnormal accumulation of lipids in lysosomes.

Genetic diseases caused by mutations in GBA1 include neurodegenerative diseases such as Gaucher's disease and Parkinson's disease. Gaucher's disease is a rare genetic disease caused by GBA1 gene mutations. Currently, the treatment for Type 1 Gaucher's disease is enzyme replacement therapy (ERT) administered every two weeks. ERT is very expensive and not effective for neuronopathic forms of Gaucher's disease. Mutations in GBA1 also are linked to Parkinson's disease (PD) by increasing the risk of PD. The so-called "pharmacological chaperone strategy" has been previously attempted in order to activate GCase. However, none of the compounds used in the pharmacological chaperone strategy were successful in activating GCase presumably because they targeted the active site of GCase.

Here, we disclose novel substituted 4-methylpyrrrolo[1,2-a]pyrimidine-8-carboxamide compounds which modulate glucocerebrosidase activity. The substituted 4-methylpyrrolo[1,2-a]pyrimidine-8-carboxamide compounds disclosed herein have better chemical and physical properties than previous reported non-active site GCase inhibitors. (See Goldin et al., WO, "Substituted pyrazolopyrimidines as glucocerebrosidase activators." December 2010, WO2012078855; and Patnaik et al., "Discovery, structure-activity relationship, and biological evaluation of noninhibitory small molecule chaperones of glucocerbrosidase," J. Med. Chem. 2012 Jun. 28; 55(1'2):5734-48, the contents of which are incorporated herein by reference in their entireties). These better chemical and physical properties of the disclosed 4-methylpyrrrolo[1,2-a]pyrimidine-8-carboxamide compounds include polar surface area, solubility, increased number of rotatable bonds, and increased number of potential hydrogen bonding members. Some of the substituted 4-methylpyrrrolo[1,2-a]pyrimidine-8-carboxamide compounds in the present study are capably of highly activating GCase. For example, some of the substituted 4-methylpyrrrolo[1,2-a]pyrimidine-8-carboxamide compounds bind to GCase covalently and activate wild-type GCase up to 15-30 fold. GCase thus activated by the novel compounds is observed to be more stable in an acidic environment than non-activated GCase. Moreover, we found that the substituted 4-methylpyrrrolo[1,2-a]pyrimidine-8-carboxamide compounds can be conjugated to fluorophones to create pyrrolopyrimidine fluorescent probes which show strong binding affinity in fluorescence polarization assays. This suggests that these pyrrolopyrimidine fluorescent probes may be utilized in high throughput screening methods to identify further modulators of GCase activity.

SUMMARY

Disclosed are new small molecules having a substituted 4-methylpyrrrolo[1,2-a]pyrimidine-8-carboxamide core structure and uses of the small molecules for modulating glucocerebrosidase activity. The new small molecules preferably modulate glucocerebrosidase activity by binding to glucocerebrosidase, optionally covalently, and activating glucocerebrosidase. The new small molecules may be formulated as pharmaceutical compositions that comprise the small molecules or that comprise activated glucocerebrosidase conjugated to the small molecules, which compositions may be administered in methods of treating and/or preventing diseases or disorders associated with glucocerebrosidase activity, including neurological diseases and disorders such as Gaucher's disease and Parkinson's disease. The disclosed small molecules also may comprise fluorophores or may be conjugated to fluorophores to generate fluorescent probes. The fluorescent probes contemplated herein may exhibit fluorescence polarization and may be utilized in high throughput screening methods to identify novel modulators of glucocerebrosidase.

DETAILED DESCRIPTION

Figure 1:
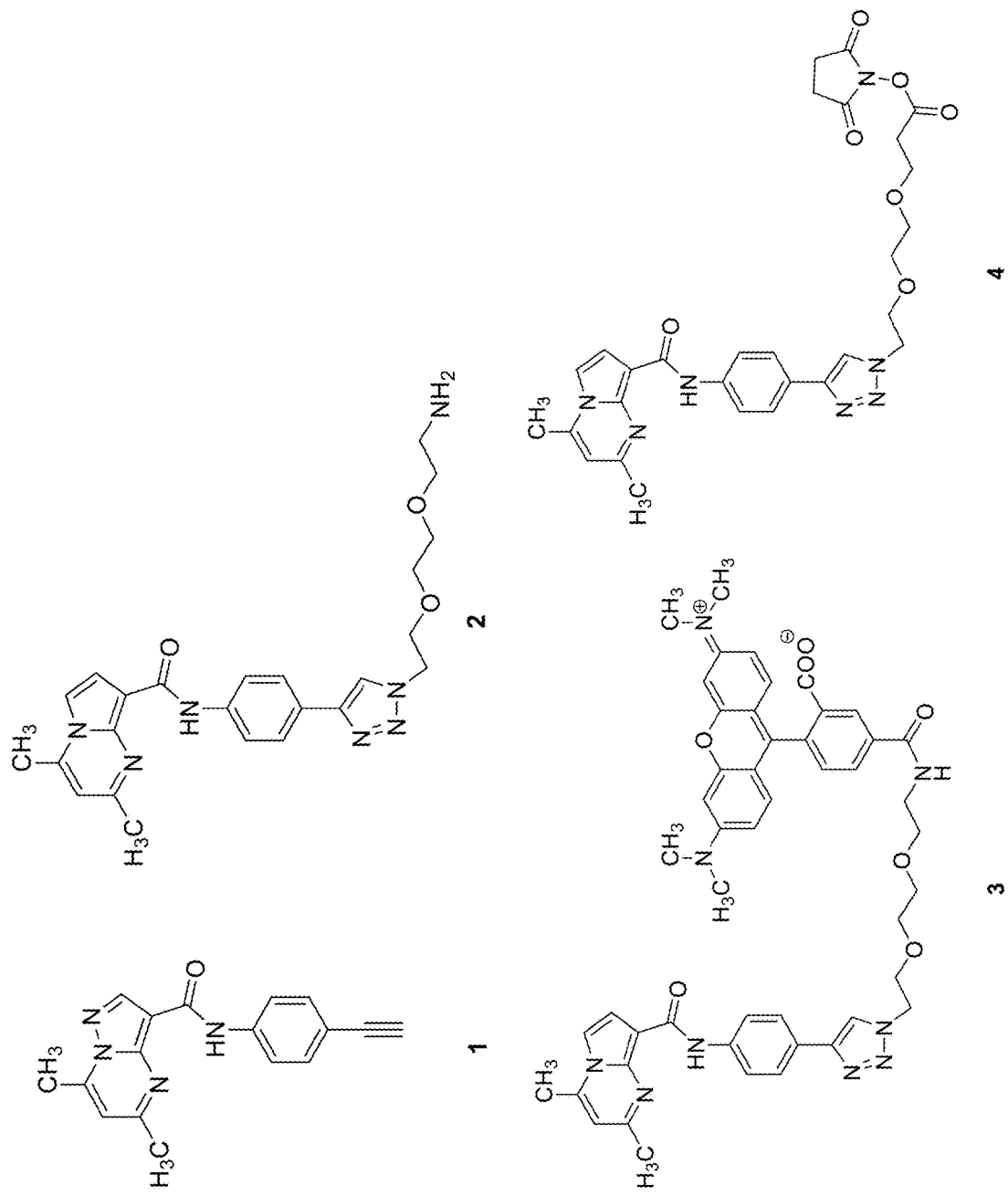
FIG. 1. Structures of GCase activators and probes.

The disclosed subject matter further may be described utilizing terms as defined below.

Unless otherwise specified or indicated by context, the terms "a", "an", and "the" mean "one or more." For example, "a modulator of glucocerebrosidase activity" should be interpreted to mean "one or more modulators of glucocerebrosidase activity."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

The terms "subject," "patient," and "individual" may be used interchangeably herein. A subject may be a human subject. A subject may refer to a human subject having or at risk for acquiring a disease or disorder that is associated with aberrant glucocerebrosidase activity. As used herein, the term "aberrant" means higher or lower activity relative to a normal healthy subject. In specific embodiments, a subject exhibiting aberrant glucocerebrosidase have or be at risk for acquiring a neurological disease or disorder, including degenerative neurological diseases or disorders such as Gaucher's disease and Parkinson's disease associated with aberrant glucocerebrosidase activity.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

The term "alkyl" as contemplated herein includes a straight-chain or branched alkyl radical in all of its isomeric forms. Similarly, the term "alkoxy" refers to any alkyl radical which is attached via an oxygen atom (i.e., a radical represented as "alkyl-O—*"). As used herein, an asterick "*" is used to designate the point of attachment for any radical group or substituent group.

As used herein, the term "modulate" means decreasing or inhibiting activity and/or increasing or augmenting activity. For example, modulating glucocerebrosidase activity means decreasing or inhibiting glucocerebrosidase activity and/or increasing or augmenting glucocerebrosidase activity. The compounds disclosed herein may be administered to modulate glucocerebrosidase activity for example, as a chaperone or activator.

The compounds disclosed herein may be referred to as "4-methylpyrrrolo[1,2-a]pyrimidine-8-carboxamide compounds." The compounds or salt or solvates thereof may be described as having a Formula I as follows:

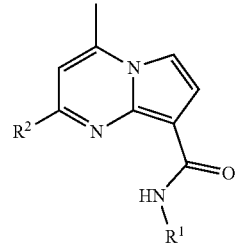

I wherein:

$R^1$ is hydrogen; a C1-C6 alkyl group; a C2-C6 alkenyl group; a C2-C6 alkynyl group; a saturated or unsaturated homocycle or heterocycle comprising one 5- or 6-membered ring; a saturated or unsaturated homocycle or heterocycle comprising two fused 5- or 6-membered rings, or an alkylthiophene (e.g., 2-methylthiophene); and $R^1$ optionally is substituted at one or more positions with a C1-C6 alkyl group; a C1-C6 alkoxy group; a halo group; a haloalkyl group; phenyl group (which optionally is substituted with halo); a benzyl group (which optionally is substituted with halo); a triazole group (optionally substituted with a carboxyl group); a 2,5-dioxopyrrolidinyl-1-yl-carboxylate group; an amino group; an alkyl-N,N-dialkyl amino group; an alkyl-alkyoxy-amino group; an alkyl-alkyoxy-alkoxy-amino group; an alkyl-alkyoxy-alkoxy-carboxamide-alkyl-morpholine group; an alkyl-alkyoxy-alkoxy-carboxamide-alkyl-1-alkylpyrrolidine group; an alkyl-alkyoxy-alkoxy-carboxamide-alkyl-cyclohexyl group; or an alkyl-alkyoxy-alkoxy-carboxamide-alkyl-cyclobutyl group); an imidazole group; a pyridyl group (e.g., 2-yl, 3-yl, or 4-yl, optionally substituted with phenoxy); a pyrrolidinyl group; a piperazinyl group; a 4-alkylpiperazine group; a 4-benzylpiperazine group; an alkyl-4-alkylpiperazine group; a piperidinyl group; a 4-alkylpiperidine group; a 4-N,N,diakylaminopiperidine group; a morpholinyl group; an alkylmorpholine group; an amino group; an alkylamino group; a dialkyl amino group; an alkyl-N,N, dialkylamino group; an azide group; a hydroxyl group; an alkylhydroxyl group; an alkynylphenyl group; a phenylmethanone group; an oxyphenyl group; an oxycarboxyl group; or $R^1$ has a formula selected from:

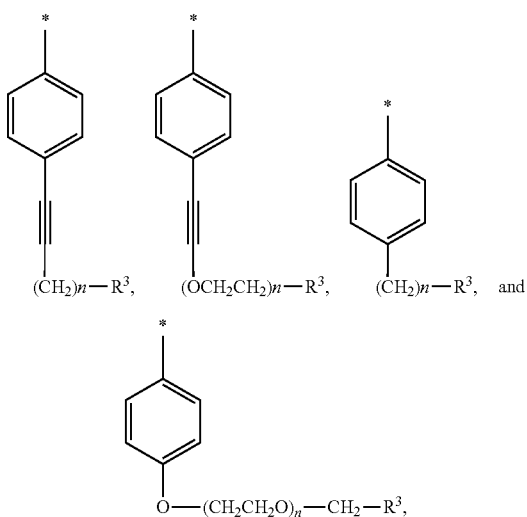

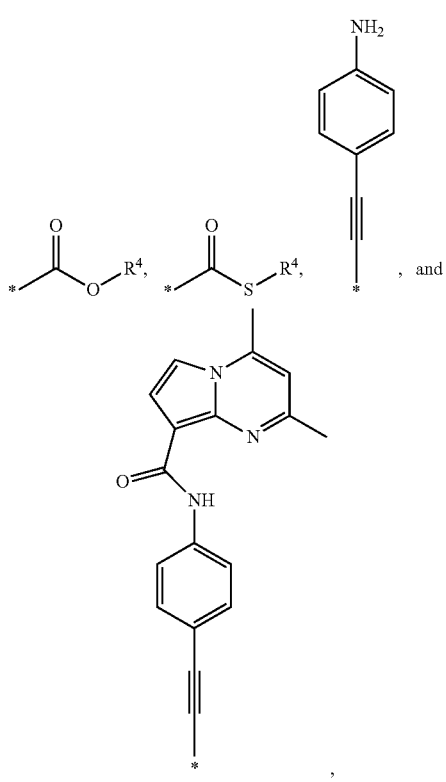

and $R^4$ is H, C1-C8 alkyl, phenyl, or succinimidyl (e.g., N-succinimidyl); and $R^2$ is C1-C6 alkyl or pyridinyl (e.g., 2-yl, 3-yl, or 4-yl). Compounds in which $R^2$ is methyl in particular are disclosed and may be referred to as 2,4-dimethylpyrrolo[1,2-a]pyrimidine-8-carboxamide compounds. Compounds in which $R^2$ is 3-yl-pyridine in particular are disclosed and may be referred to as 2-(pyridin-3-yl)-4-methylpyrrrolo[1,2-a]pyrimidine-8-carboxamide compounds.

In some embodiments, $R^1$ is selected from the group consisting of

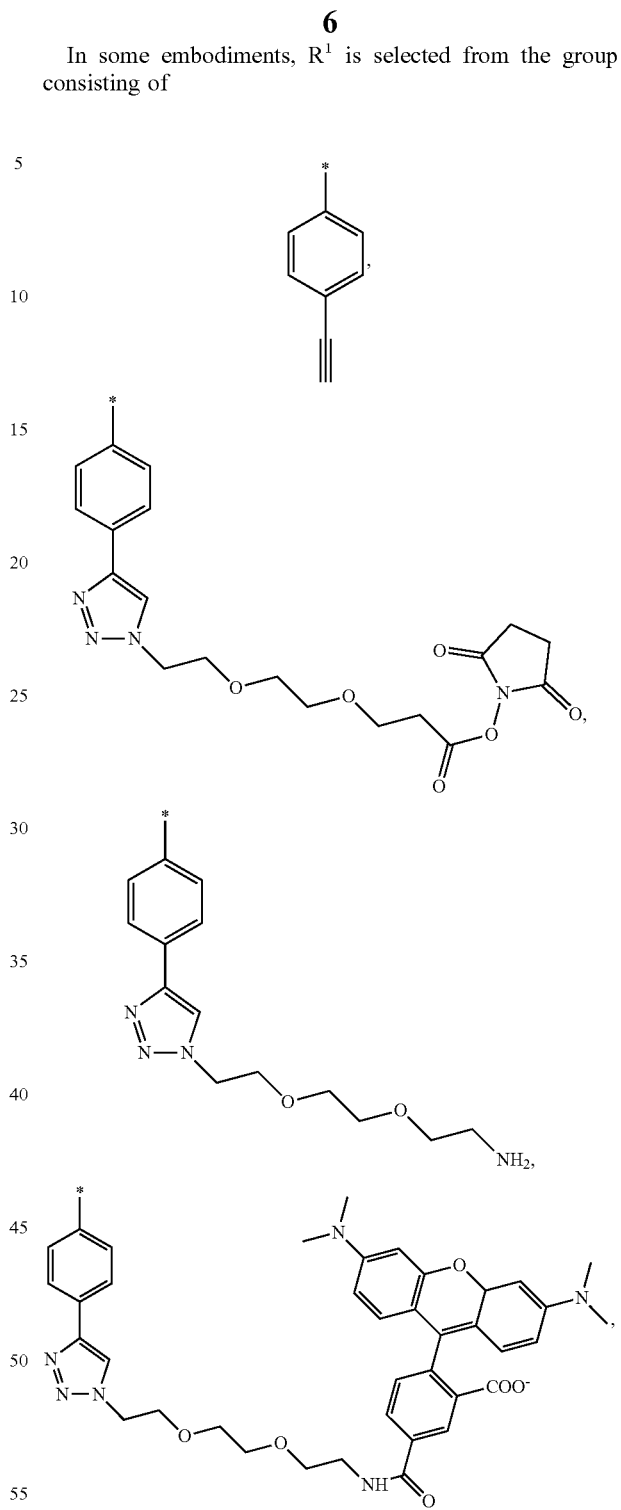

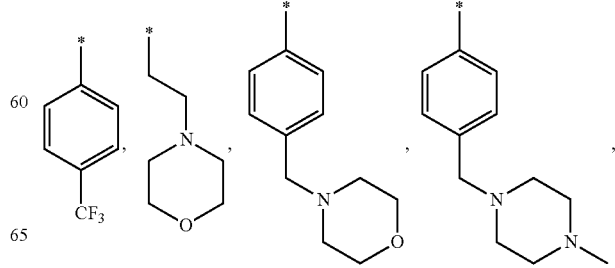

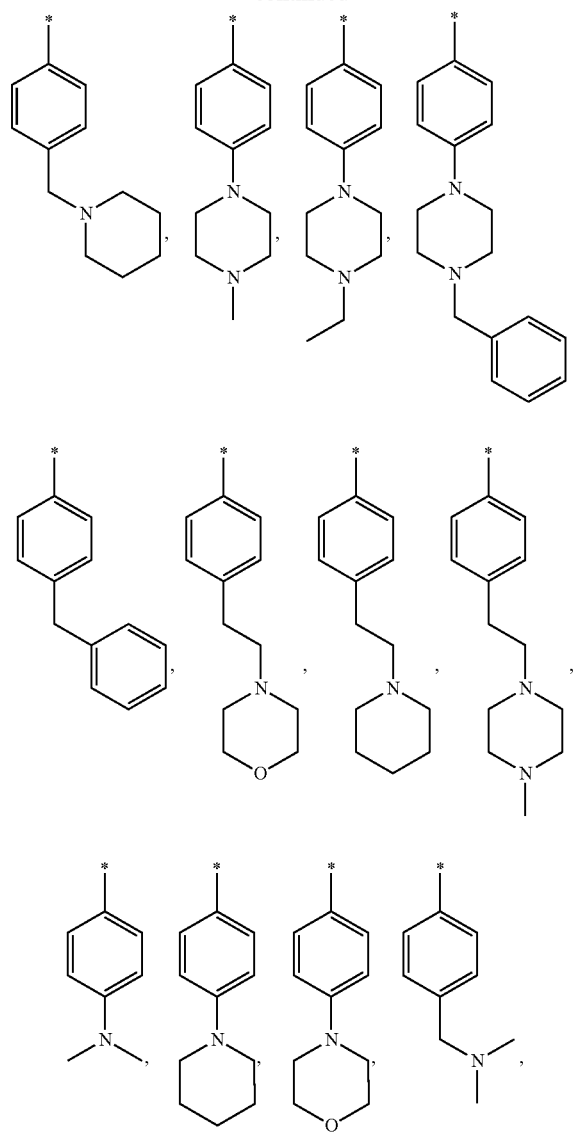
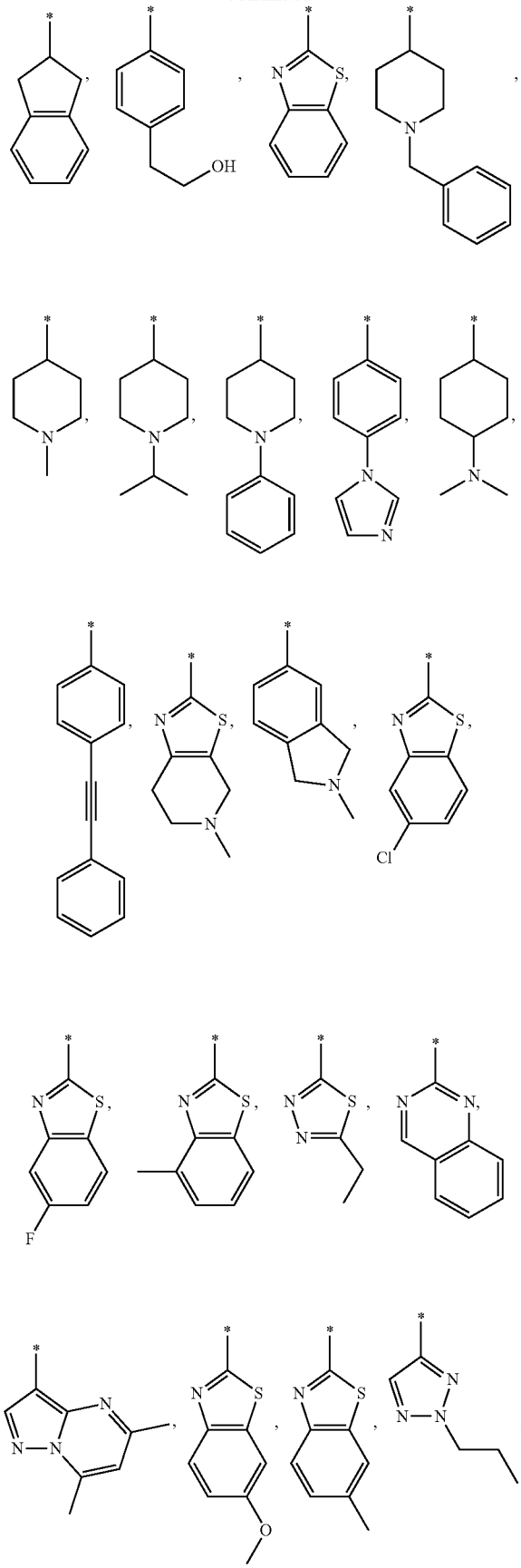

-continued
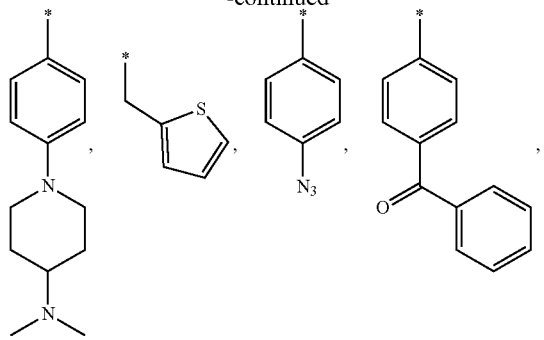
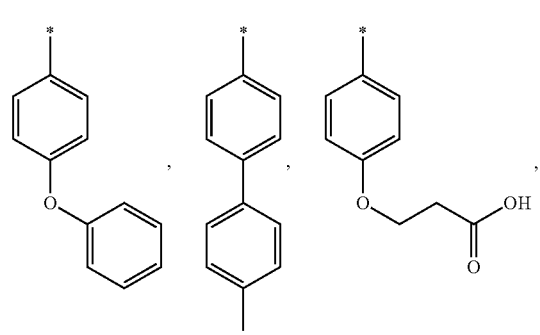
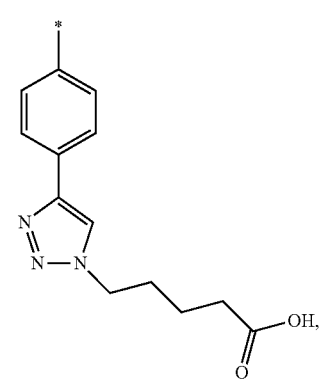
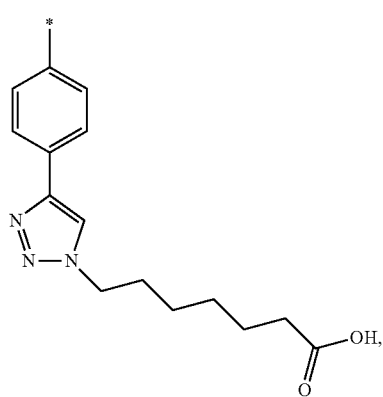
-continued
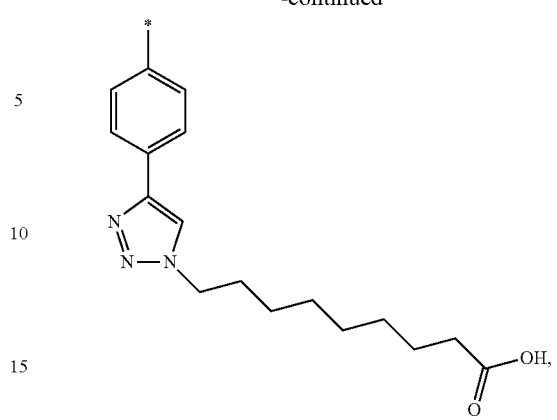
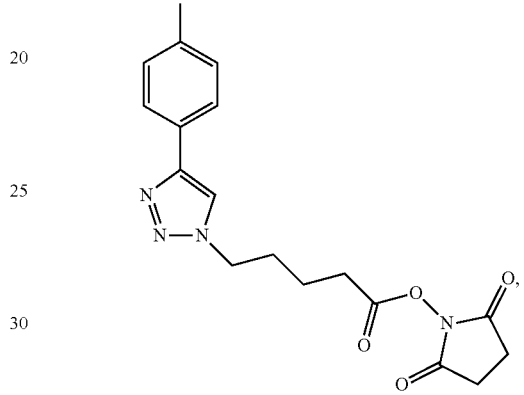
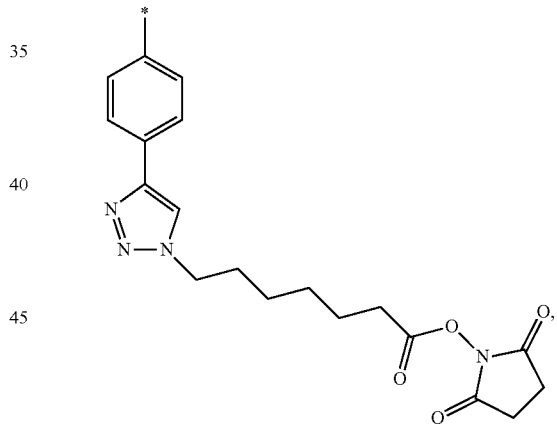
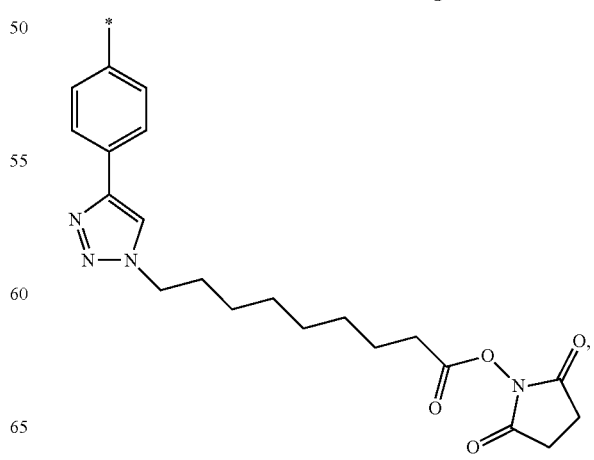

-continued
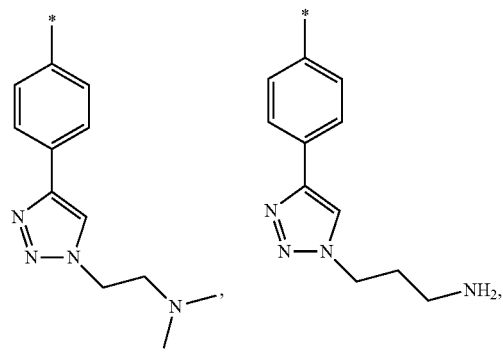
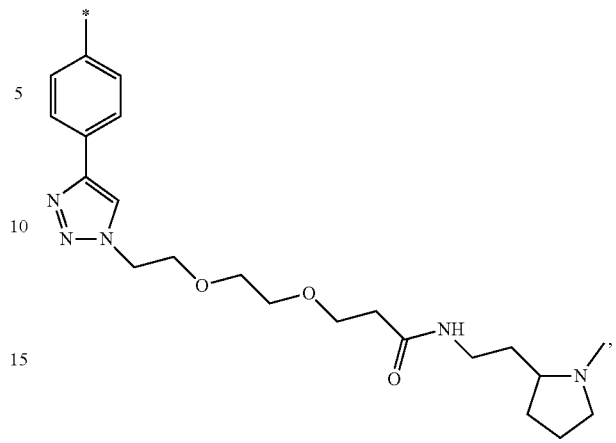
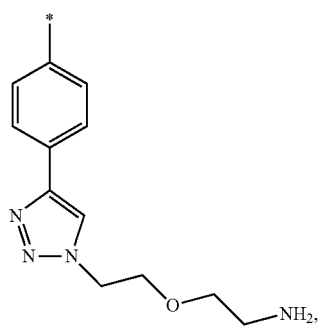
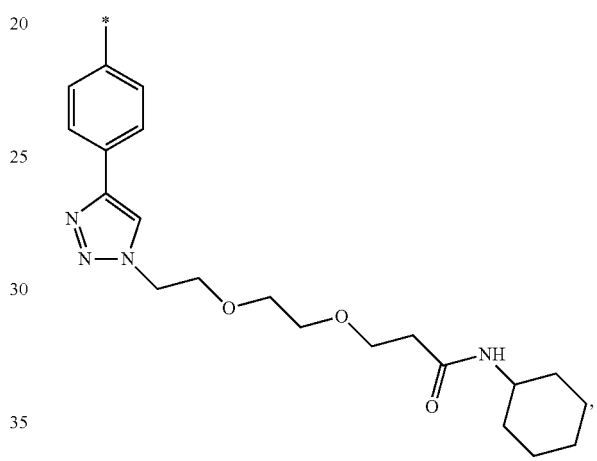
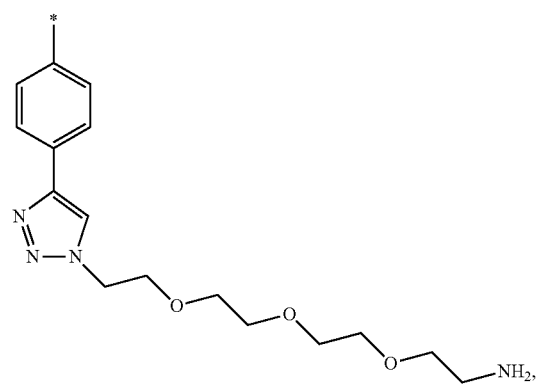
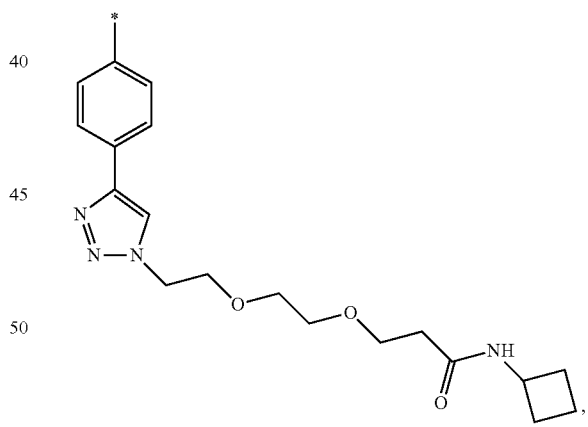
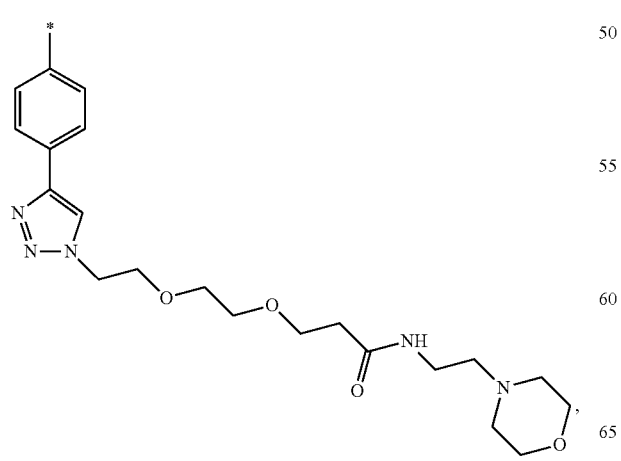
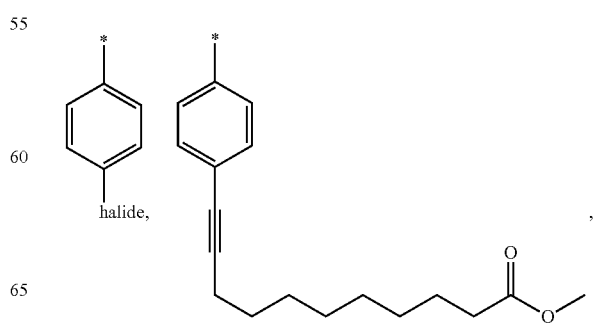

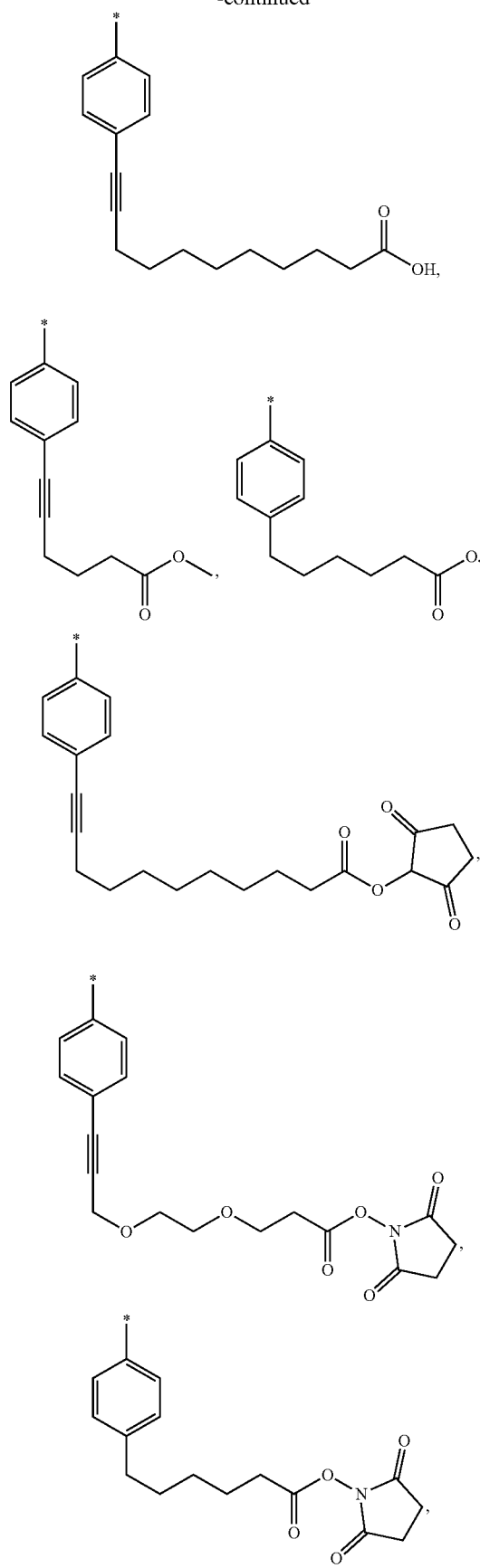
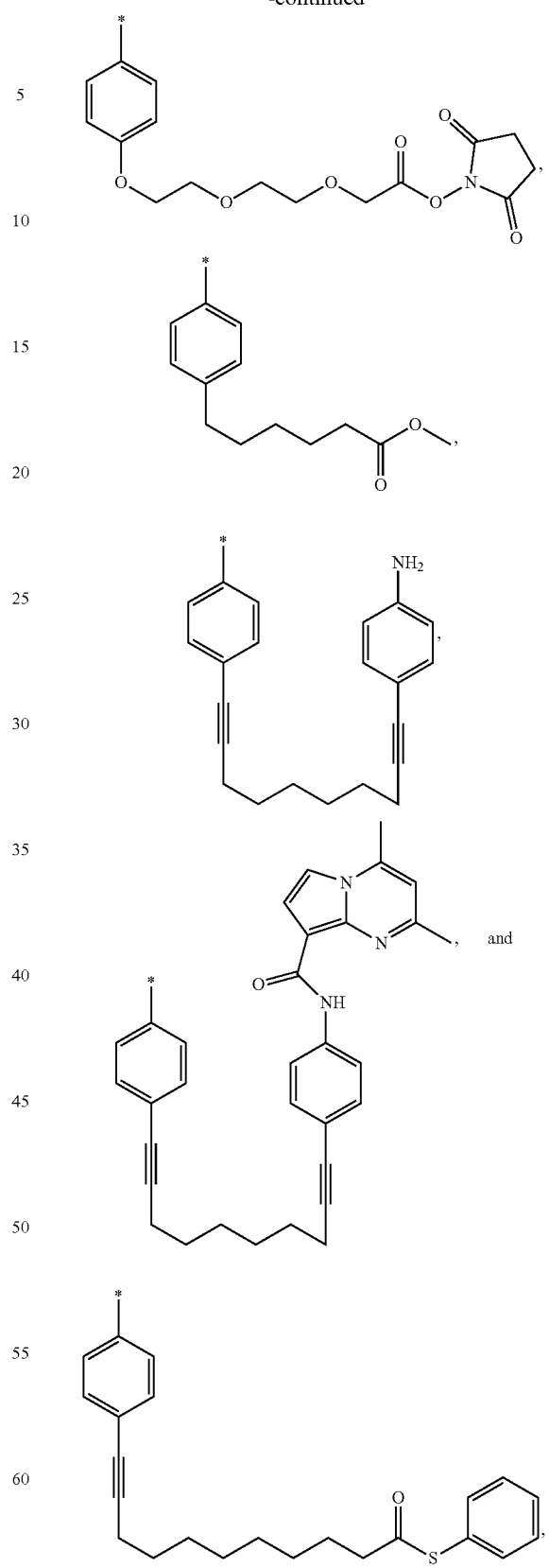
where the asterick (*) designates the point of attachment of $R^1$ to the 8-carboximide nitrogen atom.

In some embodiments, the disclosed compounds have a Formula IA:

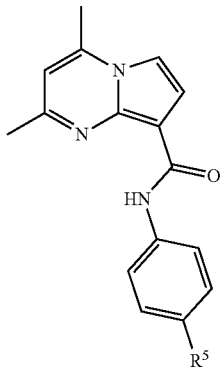

IA wherein:

R⁵ is hydrogen a C1-C6 alkyl group; a C2-C6 alkenyl group; a C2-C6 alkynyl group; a C1-C6 alkoxy group; a halo group; a haloalkyl group; a phenyl group; a benzyl group; a triazole group (optionally substituted with a carboxyl group, a 2,5-dioxopyrrolidinyl-1-yl-carboxylate group, an amino group, an alkyl-N,N-dialkyl amino group, an alkyl-alkyoxy-amino group, an alkyl-alkyoxy-alkoxy-amino group, an alkyl-alkyoxy-alkoxy-carboxamide-alkyl-morpholine group, an alkyl-alkyoxy-alkoxy-carboxamide-alkyl-1-alkylpyrrolidine group, an alkyl-alkyoxy-alkoxy-carboxamide-alkyl-cyclohexyl group, or an alkyl-alkyoxy-alkoxy-carboxamide-alkyl-cyclobutyl group); an imidazole group; a pyrrolidine group; a piperazine group; a 4-alkylpiperazine group; a 4-benzylpiperazine group; an alkyl-4-alkylpiperazine group; a piperidine group; a 4-alkylpiperidine group; a 4-N,N,diakylaminopiperidine group; a morpholine group; an alkylmorpholine group; an amino group; an alkylamino group; a dialkyl amino group; an alkyl-N,N-dialkylamino group; an azide group; a hydroxyl group; an alkylhydroxyl group; an alkynylphenyl group; a phenylmethanone group; an oxyphenyl group; or an oxycarboxyl acid group.

In some embodiments, the disclosed compounds have a Formula IB:

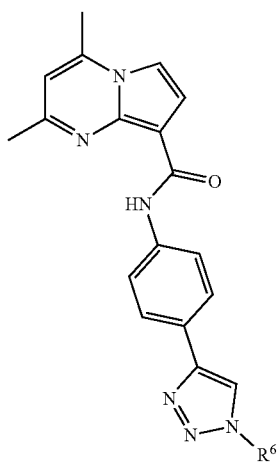

IB wherein:

R⁶ is a carboxyl group, a 2,5-dioxopyrrolidinyl-1-yl-carboxylate group; an alkylamino group; an alkyl-N,N-dialkyl amino group; an alkyl-alkyoxy-amino group; an alkyl-alkyoxy-alkoxy-amino group; an alkyl-alkyoxy-alkoxy-carboxamide-alkyl-morpholine group; an alkyl-alkyoxy-alkoxy-carboxamide-alkyl-1-alkylpyrrolidine group; an alkyl-alkyoxy-alkoxy-carboxamide-alkyl-cyclohexyl group; and an alkyl-alkyoxy-alkoxy-carboxamide-alkyl-cyclobutyl group.

The disclosed compounds may comprise or may be conjugated to a fluorophore. In some embodiments of the disclosed compounds, any of substituents R¹, R², R³, R⁴, R⁵, and R⁶, may comprise a fluorophone, including fluorophores suitable for use in fluorescence polarization assays. As used herein, a "fluorophore" is a chemical group that can be excited (e.g., by light or a chemical reaction) to emit fluorescence. Some suitable fluorophores may be excited by light to emit phosphorescence. As used herein, a "dye" may include a fluorophore. The dithio compounds described herein may include fluorophore selected from but not limited to: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Amino actinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP—Cyan Fluorescent Protein; CFP/ YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD—Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3. As used herein, a "fluorophore" may include a salt of the fluorophore.

In some embodiments, the disclosed compounds have a Formula ID:

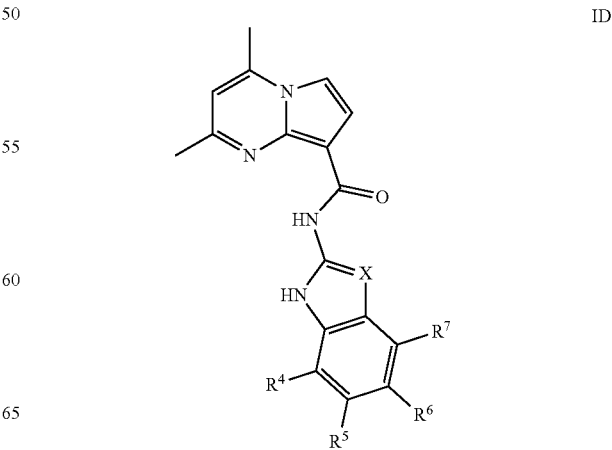

wherein:

X is N or S; and $R^4$, $R^5$, $R^6$, and $R^7$, are each independently selected from hydrogen, C1-C6 alkyl, C1-C6 alkoxy, and halogen.

The disclosed compounds may include two substituted 4-methylpyrrrolo[1,2-a]pyrimidine-8-carboxamide groups conjugated via a linker. Compounds that include two substituted 4-methylpyrrrolo[1,2-a]pyrimidine-8-carboxamide groups conjugated via a linker between the carboxamide groups may be illustrated as follows:

In some embodiments, the disclosed compounds having two substituted 4-methylpyrrrolo[1,2-a]pyrimidine-8-carboxamide groups conjugated via a linker may be described as having a Formula II as follows:

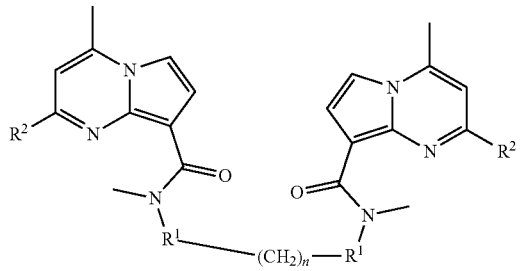

II

In some embodiments, the disclosed compounds having two substituted 4-methylpyrrrolo[1,2-a]pyrimidine-8-carboxamide groups conjugated via a linker may be described as having a Formula III as follows:

III

In some embodiments, the disclosed compounds having two substituted 4-methylpyrrrolo[1,2-a]pyrimidine-8-carboxamide groups conjugated via a linker may be described as having a Formula IV as follows:

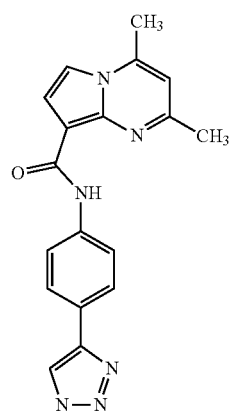

IV

The compounds disclosed herein preferably modulate activity of glucocerebrosidase. Modulation may include inhibiting or decreasing glucocerebrosidase activity. Modulation also may include activating or increasing glucocerebrosidase activity. Glucocerebrosidase activity may be assessed utilizing methods known in the art and the methods disclosed herein, including the methods disclosed in the Examples provided herein. In some embodiments, the compounds decrease or increase glucocerebrosidase activity relative to a control (e.g., by at least about 10%, 20%, 30%, 40%, 50%, 60%, 70%, 80%, 90%, or more). In other embodiments, an $AC_{50}$ value or $IC_{50}$ value for the compound in regard to inhibition or activation of glucocerebrosidase may be determined and preferably the compound has an $AC_{50}$ value or $IC_{50}$ value of less than about 10 μM, 5 μM, or 1 μM, 0.5 μM, 0.1 μM, 0.05 μM, 0.01 μM, 0.005 μM, or 0.001 μM.

The compounds disclosed herein (e.g., compounds of Formula I) may have several chiral centers, and stereoisomers, epimers, and enantiomers are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers, or analogs or derivatives thereof are contemplated herein (e.g., a composition comprising at least about 90%, 95%, or 99% pure stereoisomer, epimer, or enantiomer.) As used herein, formulae which do not specify the orientation at one or more chiral centers are meant to encompass all orientations and mixtures thereof.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that modulates glucocerebrosidase activity may be administered as a single compound or in combination with another compound that modulates glucocerebrosidase activity or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated glucocerebrosidase activity. For example, the pharmaceutical compositions may be utilized to treat patients having or at risk for acquiring a neurological disease or disorder, including degenerative neurological diseases or disorders such as Gaucher's disease and Parkinson's disease. Suitable patients include, for example mammals, such as humans and non-human primates (e.g., chimps) or other mammals (e.g., dogs, cats, horses, rats, and mice). Suitable human patients may include, for example, those who have previously been determined to be at risk of having or developing a neurological disease or disorder, including degenerative neurological diseases or disorders such as Gaucher's disease and Parkinson's disease.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with superoxide dismutase mutations, including administering an effective amount of a compound that inhibits expression of the mutated form of superoxide dismutase.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The compounds disclosed in the present application may function as activators of glucocerebrosidase. For example, a compound disclosed herein may be reacted with glucocerebrosidase to prepare an activated glucocerebrosidase that is covalent attached to the compound. The activated glucocerebrosidase thusly formed may be prepared as a pharmaceutical composition to treat and/or prevent a disease or disorder that is associated with glucocerebrosidase activity as in enzyme replacement therapy, which is known in the art.

The following list of formulations is illustrative. These illustrative formulations may be suitable for preparing pharmaceutical compositions that include the disclosed compounds as "active ingredients." The following list of formulations is illustrative and should not be interpreted as limiting the present disclosure or claims in any way:

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
| --- | --- |
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules, each containing 80 mg medicament, are made as follows:

| | |
|---|---|
| Active Ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| | |
|---|---|
| Active Ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl, cellulose and syrup to form a smooth paste. The benzoic acid solution, flavor, and color are diluted with some of the water and added with stirring. Sufficient water is then added to produce the required volume.

Formulation 8

An intravenous formulation containing 100 mg of medicament per 5 ml dose can be prepared as follows:

| | |
|---|---|
| Active Ingredient | 100 mg |
| Mannitol | 100 mg |
| 5 N Sodium hydroxide | 200 ml |
| Purified water to total | 5 ml |

EXAMPLES

The followings Examples are illustrative only and are not intended to limit the scope of the claimed subject matter.

Pyrrolopyrimidine Compounds as Glucocerebrosidase Modulators and Their Applications The compounds were prepared using Scheme I below:

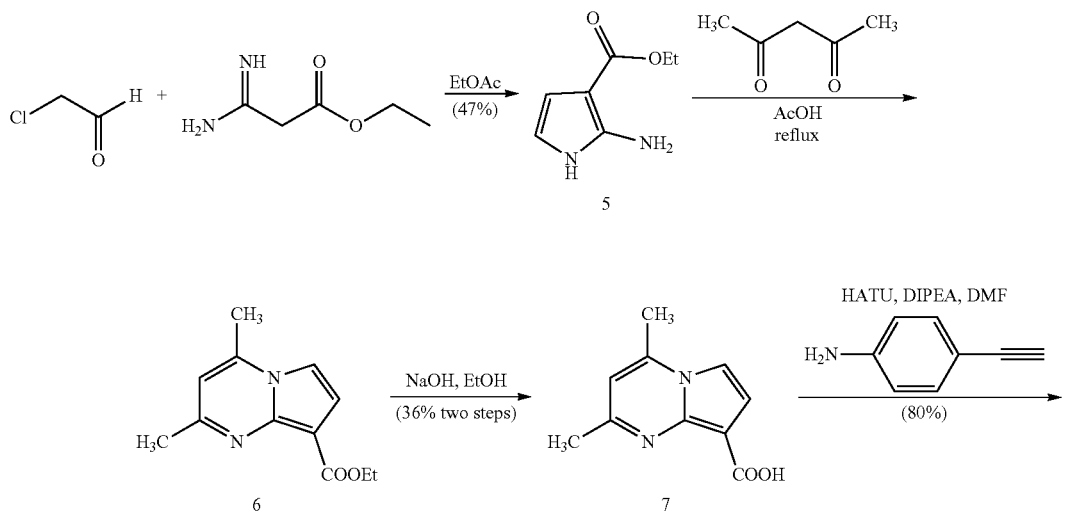

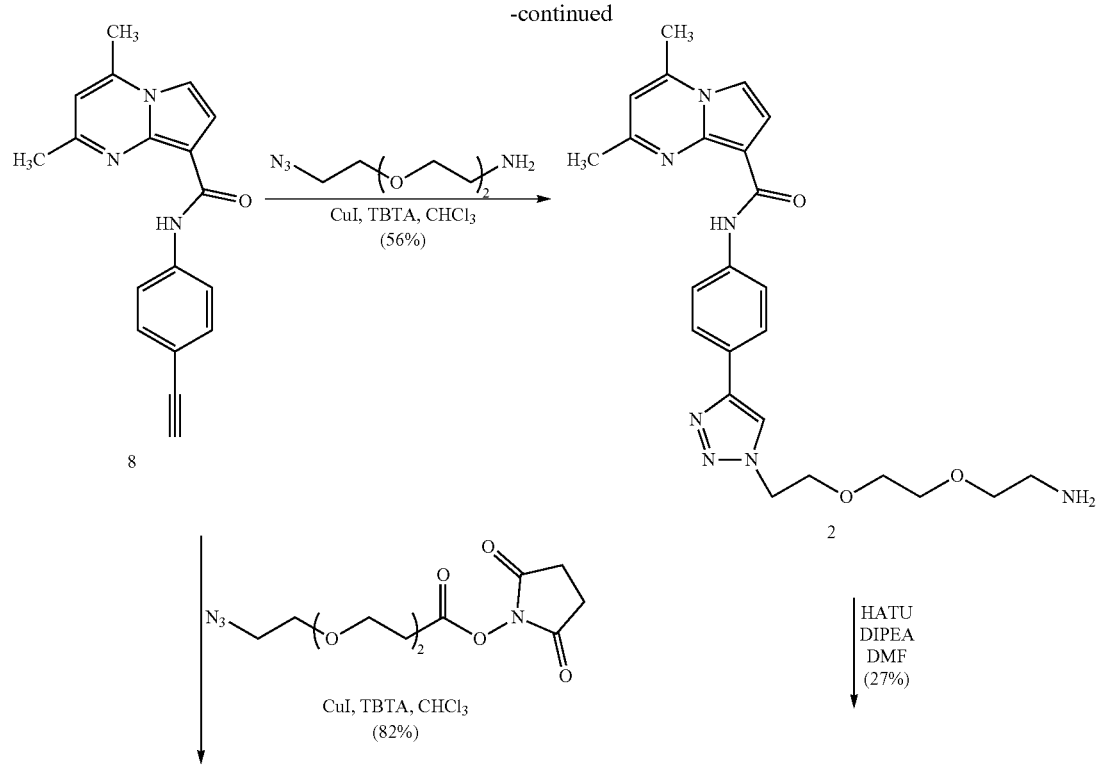
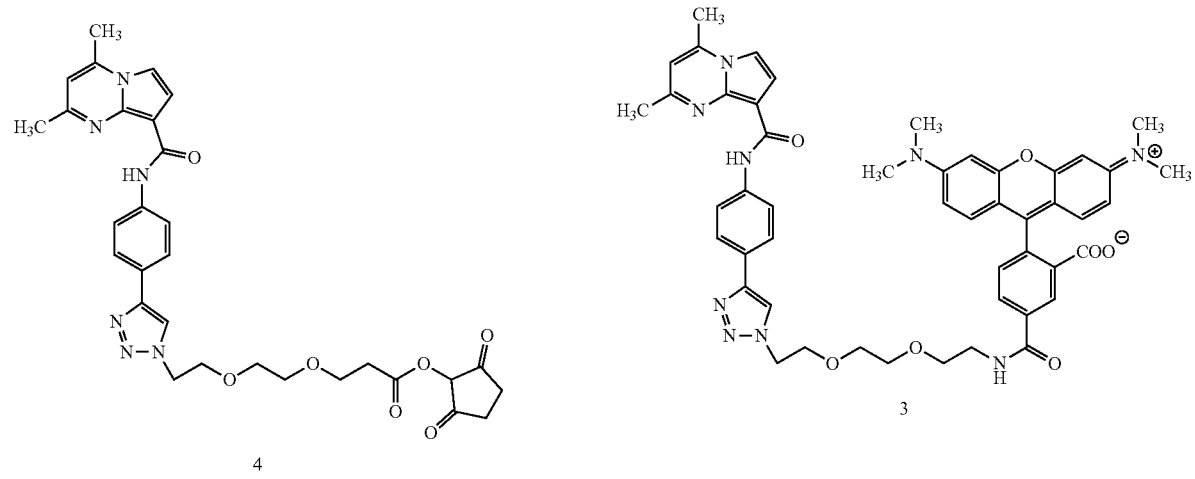

Example 1—Preparation of N-(4-ethynylphenyl)-2,4-dimethylpyrrolo[1,2-a]pyrimidine-8-carboxamide (1)

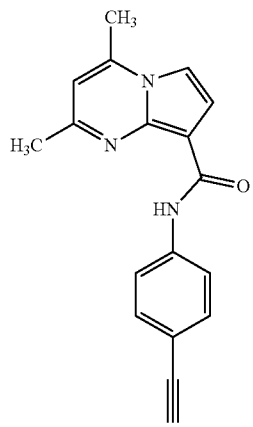

a. Preparation of ethyl 2-amino-1H-pyrrole-3-carboxylate. To a solution of carbethoxyacetamidine (390 mg, 3.0 mmol) in dried ethyl acetate (20 mL) under an argon atmosphere was rapidly added anhydrous chloroacetaldehyde under vigorous stirring at 22° C. The reaction was stirred for 10 min and heated at reflux for 20 min. The mixture was cooled to room temperature and filtered through silica gel (15 g). The residue in the reaction flask was extracted with ethyl acetate (20 mL×5), and filtered. The filtrate was collected and evaporated under reduced pressure to give 120 mg (47%) as a light yellow solid.

$^1$H NMR: (500 MHz, CDCl$_3$) δ (ppm): 7.92 (br, 1H), 6.28 (t, J=2.8 Hz, 1H), 6.15 (dd, J=2.0 Hz, 1H), 4.94 (br, 2H), 4.24 (q, J=7.1 Hz, 2H), 1.33 (t, J=7.1 Hz, 3H). $^{13}$C NMR: (125 MHz, CDCl$_3$) δ (ppm): 166.5, 145.4, 110.3, 107.5, 94.5, 59.3, 14.7.

b. Preparation of ethyl 2,4-dimethylpyrrolo[1,2-a]pyrimidine-8-carboxylate. Under a nitrogen atmosphere, pentane-2,4-dione (14.3 mL, 139 mmol) and ethyl 2-amino-1H-pyrazole-3-carboxylate (19.5 g, 127 mmol) were heated in a sealed tube with acetic acid (200 mL) at 110° C. overnight. The acetic acid was evaporated under reduced pressure to give the crude product, which was purified by flash chromatography to give 10.0 g (36%) as a light yellow powder.

$^1$H NMR: (500 MHz, CDCl$_3$) δ (ppm): 7.39 (d, J=3.4 Hz, 1H), 7.01 (d, J=3.4 Hz, 1H), 6.53 (s, 1H), 4.40 (q, J=7.1 Hz, 1H), 2.62 (s, 1H), 2.56 (s, 1H), 1.41 (t, J=7.1 Hz, 1H). $^{13}$C NMR: (125 MHz, CDCl$_3$) δ (ppm): 164.3, 157.6, 142.3, 141.8, 118.0, 109.0, 106.6, 102.3, 59.9, 29.8, 25.2, 18.3, 14.7. ESI-MS m/z: 241 (M+Na$^+$), 219 (M+H$^+$).

c. Preparation of 2,4-dimethylpyrrolo[1,2-a]pyrimidine-8-carboxylic acid. Ethyl 2,4-dimethylpyrrolo[1,2-a]pyrimidine-8-carboxylate (10.0 g, 45.9 mmol) was suspended in EtOH (200 mL) and treated with 3.4 M sodium hydroxide (80 mL, 275 mmol). The mixture was heated to 90° C. and then stirred for 1 h. The mixture was cooled to room temperature and neutralized with acetic acid (15.7 mL, 275 mmol) to pH 6-7. The slurry was filtered, and the solid residue was washed with water and dried in vacuum to obtain a yellow powder (7.0 g, 80%).

$^1$H NMR: (500 MHz, d6-DMSO) δ (ppm): 11.67 (s, 1H), 7.40 (d, J=3.3 Hz, 1H), 7.26 (d, J=3.3 Hz, 1H), 6.85 (s, 1H), 2.61 (s, 3H), 2.51 (s, 3H). $^{13}$C NMR: (125 MHz, d6-DMSO) δ (ppm): 164.1, 156.8, 143.6, 141.3, 117.0, 108.8, 108.5, 101.0, 24.1, 17.6. ESI-MS m/z: 213 (M+Na$^+$), 191 (M+H$^+$).

d. Preparation of N-(4-ethynylphenyl)-2,4-dimethylpyrrolo[1,2-a]pyrimidine-8-carboxamide (1). 2,4-Dimethylpyrrolo[1,2-a]pyrimidine-8-carboxylic acid (1.0 g, 5.2 mmol), 4-ethynylaniline (0.61 g, 5.2 mmol), and HATU (2.0 g, 5.2 mmol) were dissolved in DMF (10 mL) and then treated with diisopropylethylamine (2.75 mL, 15.8 mmol). The mixture was stirred at 60° C. overnight. The mixture was diluted with water and filtered. The residue was washed with water (×2) and dried in vacuum to obtain a yellow solid (1.0 g, 66%).

$^1$H NMR: (500 MHz, CDCl$_3$) δ (ppm): 10.87 (s, 1H), 7.74 (d, J=8.6 Hz, 2H), 7.56 (d, J=3.3 Hz, 1H), 7.48 (d, J=8.6 Hz, 2H), 7.07 (d, J=3.3 Hz, 1H), 6.53 (s, 1H), 3.04 (s, 1H), 2.63 (s, 3H), 2.58 (s, 3H). $^{13}$C NMR: (125 MHz, CDCl$_3$) δ (ppm): 162.5, 155.7, 142.7, 140.3, 139.6, 133.0, 119.0, 117.3, 116.0, 108.5, 107.2, 105.6, 84.1, 76.2, 24.8, 18.3. ESI-MS m/z: 312 (M+Na$^+$).

Example 2—Preparation of N-(4-(1-(2-(2-(2-aminoethoxy)ethoxy)ethyl)-1H-1,2,3-triazol-4-yl)phenyl)-2,4-dimethylpyrrolo[1,2-a]pyrimidine-8-carboxamide (2)

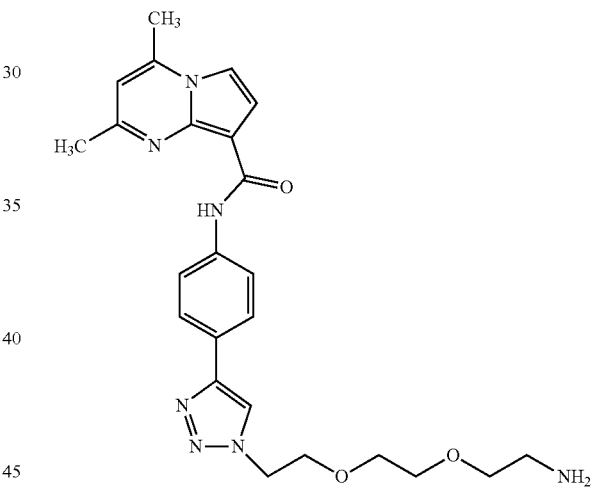

A mixture of N-(4-ethynylphenyl)-2,4-dimethylpyrrolo[1,2-a]pyrimidine-8-carboxamide (145 mg, 0.5 mmol), 2-(2-(2-azidoethoxy)ethoxy)ethanamine (87 mg, 0.5 mmol) and copper (I) iodide (20 mg) in chloroform (5 mL) was stirred at room temperature for 3 h. The mixture was filtered, and the filtrate was concentrated and purified by flash chromatography to give a yellow foam (130 mg, 56%). The product is a mixture of 1,4-disubstituted and 1,5-disubstituted regioisomers (4:1).

The data of the 1,4-disubstituted regioisomers is reported here. $^1$H NMR: (500 MHz, CDCl$_3$) δ (ppm): 10.82 (s, 1H), 7.92 (s, 1H), 7.83 (d, J=8.6 Hz, 2H), 7.80 (d, J=8.6 Hz, 2H), 7.55 (d, J=3.2 Hz, 1H), 7.05 (d, J=3.2 Hz, 1H), 6.51 (s, 1H), 4.57 (t, J=5.0 Hz, 2H), 3.90 (t, J=5.1 Hz, 2H), 3.63-3.54 (m, 4H), 3.45 (t, J=5.2 Hz, 2H), 2.82 (t, J=5.2 Hz, 2H), 2.63 (s, 3H), 2.56 (s, 3H), 2.15 (br, 2H). $^{13}$C NMR: (125 MHz, CDCl$_3$) δ (ppm): 162.5, 155.6, 147.8, 142.6, 139.6, 139.5, 128.2, 126.4, 125.5, 120.4, 119.6, 119.3, 117.3, 108.4, 107.1, 105.9, 73.5, 70.8, 70.3, 69.7, 50.4, 41.8, 24.8, 18.3. ESI-MS m/z: 464 (M+H$^+$).

Example 3—Preparation of 2-(3,6-Bis(dimethyl-amino)xanthylium-9-yl)-5-((2-(2-(2-(4-(4-(2,4-dimethylpyrrolo[1,2-a]pyrimidine-8-carboxamido)phenyl)-1H-1,2,3-triazol-1-yl)ethoxy)ethoxy)ethyl)carbamoyl)benzoate (3)

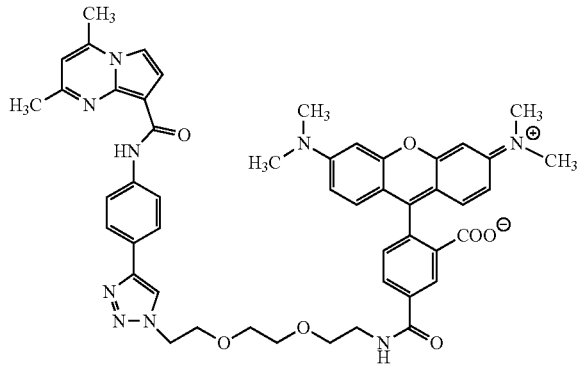

N-(4-(1-(2-(2-(2-aminoethoxy)ethoxy)ethyl)-1H-1,2,3-triazol-4-yl)phenyl)-2,4-dimethylpyrrolo[1,2-a]pyrimidine-8-carboxamide (88 mg, 0.19 mmol), 3,6-bis(dimethylamino)xanthylium-9-yl) (82 mg, 0.19 mmol), and HATU (73 mg, 0.19 mmol) were dissolved in DMF (3 mL) and then treated with diisopropylethylamine (100 µL, 0.57 mmol). The mixture was stirred at room temperature overnight. The mixture was diluted with water and filtered. The residue was washed with water (×2), and dried. The solid obtained was purified by flash chromatography to give a dark-red solid (45 mg, 27%).

$^1$H NMR: (500 MHz, CDCl$_3$) δ (ppm): 10.84 (s, 1H), 8.35 (s, 1H), 8.19 (dd, J=8.0, 1.2 Hz, 1H), 7.92 (s, 1H), 7.84 (d, J=8.6 Hz, 2H), 7.79 (d, J=8.6 Hz, 2H), 7.57 (d, J=3.3 Hz, 1H), 7.24 (d, J=8.0 Hz, 1H), 7.10 (t, J=4.9 Hz, 1H), 7.07 (d, J=3.3 Hz, 1H), 6.55 (d, J=8.0 Hz, 2H), 6.53 (s, 1H), 6.46 (d, J=2.4 Hz, 2H), 6.35 (dd, J=8.9, 2.5 Hz, 2H), 4.64 (t, J=5.1 Hz, 2H), 4.02 (t, J=5.1 Hz, 2H), 3.71-3.61 (m, 8H), 2.96 (s, 12H), 2.64 (s, 3H), 2.59 (s, 3H). $^{13}$C NMR: (125 MHz, CDCl$_3$) δ (ppm): 169.2, 166.2, 162.5, 155.7, 153.1, 152.3, 147.8, 142.6, 139.7, 139.5, 136.3, 134.4, 128.8, 128.2, 126.4, 125.3, 124.8, 123.0, 120.5, 119.7, 117.3, 108.9, 108.5, 107.1, 106.3, 105.8, 98.5, 70.6, 70.5, 69.6, 50.4, 40.3, 40.1, 24.8, 18.3. ESI-MS m/z: 876 (M+H$^+$), 898 (M+Na$^+$).

Example 4—Preparation of 2,5-Dioxopyrrolidin-1-yl 3-(2-(2-(4-(4-(2,4-dimethylpyrrolo[1,2-a]pyrimidine-8-carboxamido)phenyl)-1H-1,2,3-triazol-1-yl)ethoxy)ethoxy)propanoate (4)

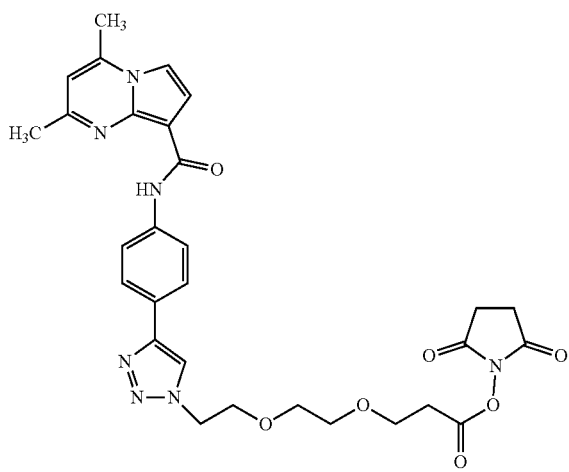

A mixture of N-(4-ethynylphenyl)-2,4-dimethylpyrrolo[1,2-a]pyrimidine-8-carboxamide (290 mg, 1.0 mmol), 2,5-dioxopyrrolidin-1-yl 3-(2-(2-azidoethoxy)ethoxy)propanoate (300 mg, 1.0 mmol), copper (I) iodide (50 mg) and tris[(1-benzyl-1H-1,2,3-triazol-4-yl)methyl]amine (5.0 mg) in chloroform (15 mL) was stirred at room temperature overnight. The solvent was evaporated and purified by flash chromatography to give a yellow powder (480 mg, 82%).

$^1$H NMR: (500 MHz, CDCl$_3$) δ (ppm): 10.82 (s, 1H), 7.95 (s, 1H), 7.83 (s, 4H), 7.56 (d, J=3.3 Hz, 1H), 7.06 (d, J=3.4 Hz, 1H), 6.52 (s, 1H), 4.59 (t, J=5.0 Hz, 2H), 3.91 (t, J=5.1 Hz, 2H), 3.83 (t, J=6.0 Hz, 2H), 3.64 (s, 4H), 2.86 (t, J=6.0 Hz, 2H), 2.78 (s, 4H), 2.64 (s, 3H), 2.57 (s, 3H). $^{13}$C NMR: (125 MHz, CDCl$_3$) δ (ppm): 169.1, 166.9, 162.4, 155.7, 147.7, 142.6, 139.6, 139.5, 126.4, 125.6, 120.6, 119.6, 117.2, 108.4, 107.0, 105.8, 70.9, 70.6, 69.8, 65.9, 50.5, 32.4, 25.7, 24.8, 18.3. ESI-MS m/z: 590 (M+H$^+$), 612 (M+Na$^+$).

Example 5—Glucocerebrosidase Activity Assay with Blue Substrate and Red Substrate The compounds in DMSO solution 0.5 µL/well were transferred to a black 96-well plate (the final titration was 24 nM to 50 µM, 12 concentrations, 2 times dilution). 33.5 µL enzyme solution (7.5 nM final concentration) was transferred to the wells. After 5 min of incubation at room temperature, the enzyme reaction was initiated by the addition of 33 µL/well blue substrate or 66.5 µL/well red substrate. Final concentrations of the blue substrate (4MU-Glc) and red substrate (Res-Glc) were 1.5 mM and 30 µM, respectively. The red substrate reaction was measured in the Biotek Synergy H1 multi-mode plate reader with Ex=573 nm and Em=610 nm at 37° C. every 20 sec for 30 min. The blue substrate reaction was terminated by the addition of 33 µL/well stop solution (1 M NaOH and 1 M glycine mixture, pH 10) after 30 min of incubation at 37° C. The fluorescence was then measured in the plate reader at Ex=365 nm and Em=440 nm.

Example 6—Glucocerebrosidase Activity Assay with Natural Substrate

The compounds in DMSO solution (0.5 µL/well) were transferred to a black 96-well plate. The final titration was 24 nM to 50 µM, 12 concentrations, 2 times dilution. 33.5 µL enzyme solution was transferred to the wells (7.5 nM final concentration). After 5 min of incubation at room temperature, the enzyme reaction was initiated by the addition of 16 µL/well natural substrate. Final concentration of the natural substrate (glucosylceramide) was 100 µM. The plate was incubated for 30 min at 37° C. and the Amplex Red Glucose/Glucose Oxidase Assay buffer (50 µL/well) was added. The plate was measured in the Biotek Synergy H1 multi-mode plate reader with Ex=573 nm and Em=610 nm at 37° C. every 20 sec for 30 min.

Example 7—Fluorescence Polarization Assay

The fluorescent probe 3 (25 nL/well, 50 nM final concentration) was transferred to a 384-well black plate using a Labcyte Echo 550 Liquid Handler system. The 25 µL/well enzyme dilutions with GCase enzyme activity buffer were added to the plate, which was shaken at room temperature in dark for 20 min. The final titration was 5 nM to 10 µM, 10 concentrations, 2 times dilution. The fluorescence polarization was measured in Molecular Devices Analyst GT with Ex=535 nm and Em=580 nm, G Factor=1.05.

Example 8—Compound High Throughput Screening (HTS) by Fluorescence Polarization

The enzyme in GCase enzyme activity buffer (25 µL/well) was added to a 384-well black plate. The fluorescent probe 3 (25 nL/well, 50 nM final concentration) was transferred to a 384-well black plate using a Labcyte Echo 550 Liquid Handler system. Compounds in DMSO stock solution (50 nL) were transferred to the plate. The plate was shaken at room temperature in dark for 20 min. The final concentration was 19.5 nM to 10 µM, 10 concentrations, 2 times dilution. The fluorescence polarization was measured in a Molecular Devices Analyst GT with Ex=535 nm and Em=580 nm, G Factor=1.05.

Example 9—Preparation of the Compound-Activated Glucocerebrosidase

To the recombinant wild type enzyme (22 µM, 95 µL, 1 equiv) in 0.1 M phosphate buffer (pH 7.2) was added 2,5-dioxopyrrolidin-1-yl 3-(2-(2-(4-(4-(2,4-dimethylpyrrolo[1,2-a]pyrimidine-8-carboxamido)phenyl)-1H-1,2,3-triazol-1-yl)ethoxy)ethoxy)propanoate (4) in DMSO (0.89 mM, 5 µL, 2 equiv) in one portion, and was vortexed for 5 sec immediately. At indicated time points, the reaction solution (2 µL) was sampled and diluted (1:3125 dilution) into the assay buffer (50 mM citric acid, 176 mM $K_2HPO_4$, and 0.01% Tween-20 at pH 5.9). After 2 h the reaction solution was dialyzed three times with 0.1 M phosphate buffer (pH 7.2). The enzyme was adjusted to the same concentration and sampled for activity. The dilution solutions were assayed with three substrates, resorufin substrate, 4-MU substrate, and natural substrate using the method in Example 5 and Example 6 without adding compounds.

Example 10—Synthesis and Testing of Additional Compounds

Additional compounds were prepared and tested according to the procedures provided in the examples above. Dose-response curves were prepared to determine $IC_{50}$ or $AC_{50}$. Results are shown in Table 1.

TABLE 1

| No. | Structures |
|---|---|
| 1 | 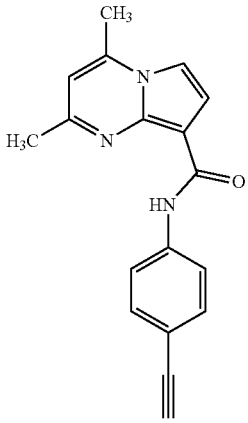 [SMILES: C#Cc1ccc(NC(=O)c2ccn3c(C)cc(C)nc23)cc1] |
| 2 | 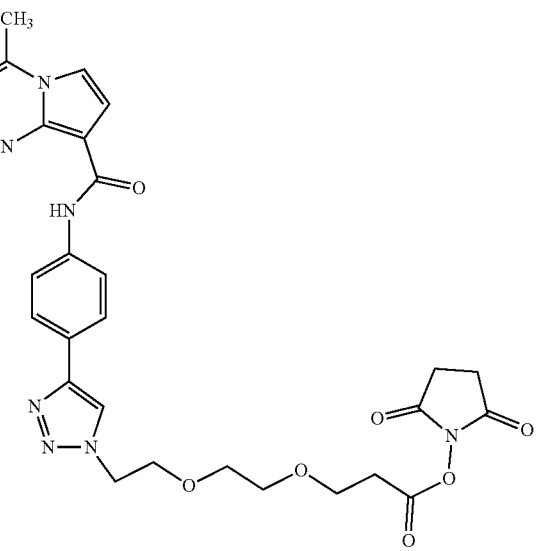 |

TABLE 1-continued
| | |
|---|---|
| 3 | 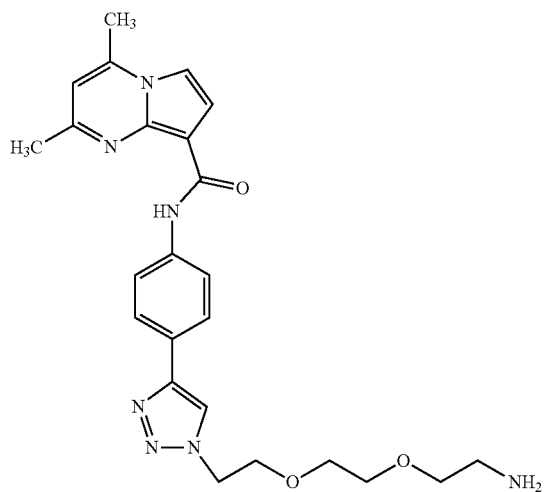 [SMILES: Cc1cc(C)n2ccc(C(=O)Nc3ccc(-c4cn(CCOCCOCCN)nn4)cc3)c2n1] |
| 4 | 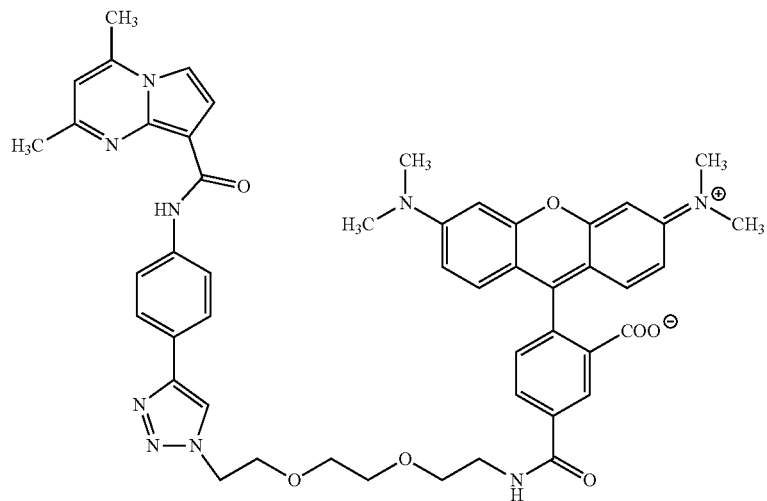 |
| 5 | 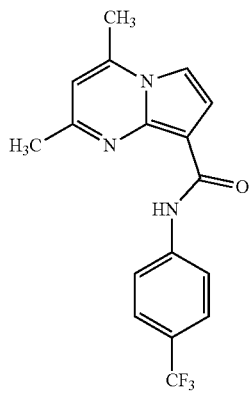 [SMILES: Cc1cc(C)n2ccc(C(=O)Nc3ccc(C(F)(F)F)cc3)c2n1] |
| 6 | 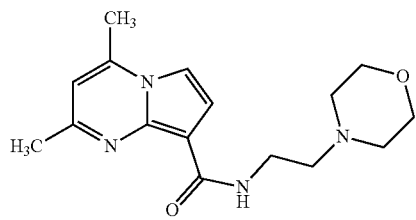 [SMILES: Cc1cc(C)n2ccc(C(=O)NCCN3CCOCC3)c2n1] |

TABLE 1-continued
7
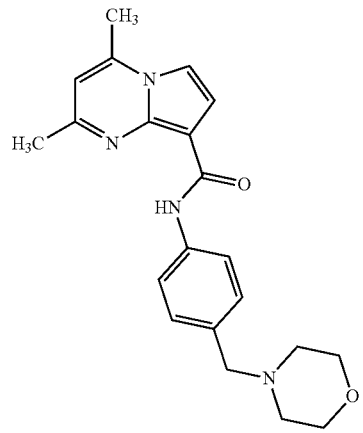 [SMILES: Cc1cc(C)n2ccc(C(=O)Nc3ccc(CN4CCOCC4)cc3)c2n1]
8
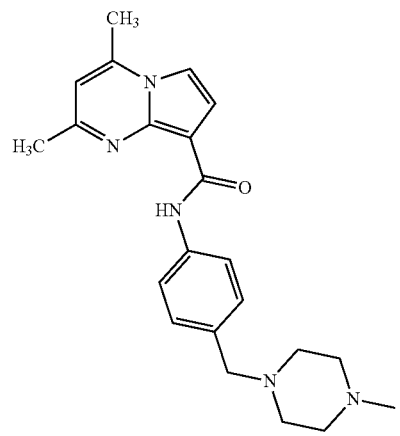
9
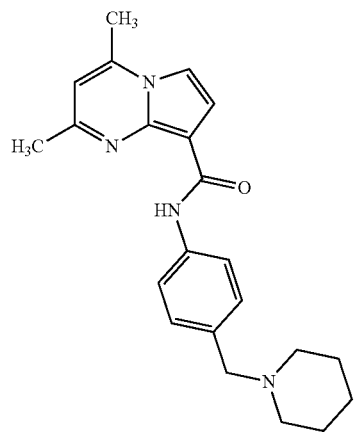 [SMILES: Cc1cc(C)n2ccc(C(=O)Nc3ccc(CN4CCCCC4)cc3)c2n1]
10
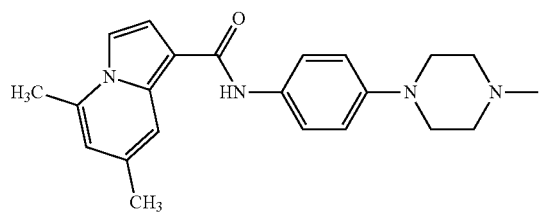

TABLE 1-continued
| 11 | 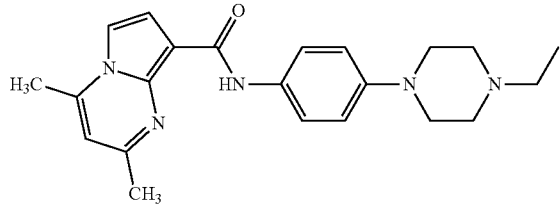 [SMILES: CCN1CCN(c2ccc(NC(=O)c3ccn4c(C)cc(C)nc34)cc2)CC1] |
| --- | --- |
| 12 | 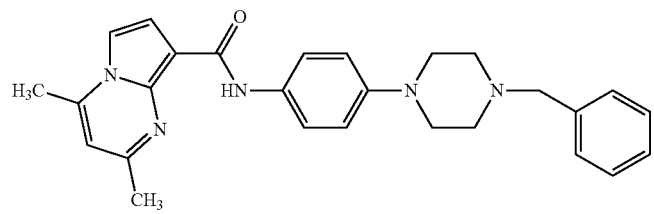 [SMILES: Cc1cc(C)n2ccc(C(=O)Nc3ccc(N4CCN(Cc5ccccc5)CC4)cc3)c2n1] |
| 13 | 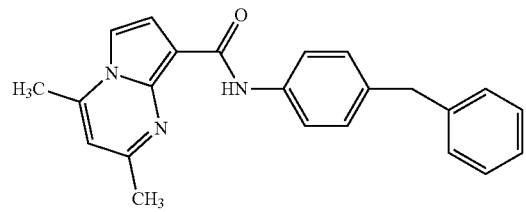 [SMILES: Cc1cc(C)n2ccc(C(=O)Nc3ccc(Cc4ccccc4)cc3)c2n1] |
| 14 | 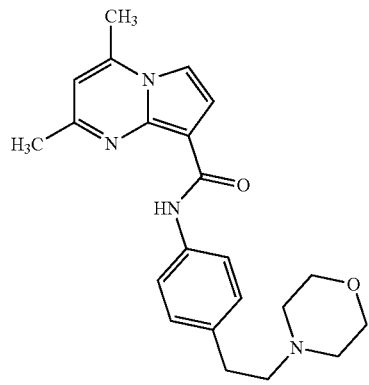 |
| 15 | 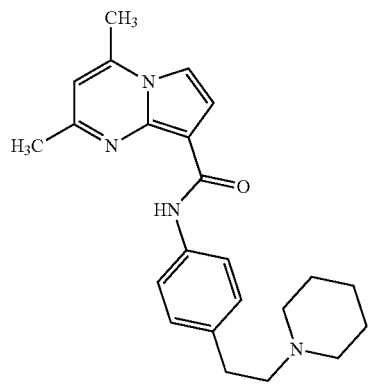 [SMILES: Cc1cc(C)n2ccc(C(=O)Nc3ccc(CCN4CCCCC4)cc3)c2n1] |

TABLE 1-continued
| | |
|---|---|
| 16 | 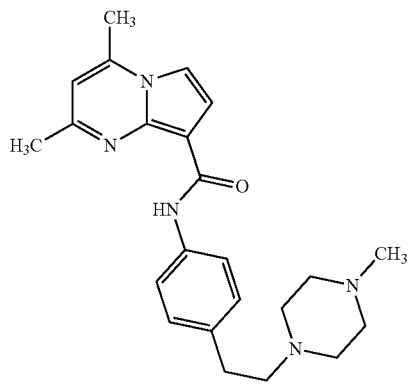 |
| 17 | 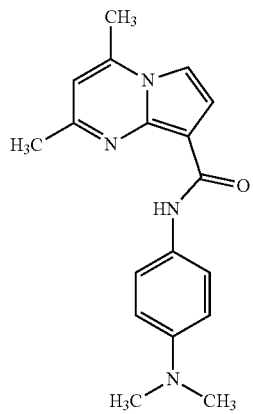 [SMILES: Cc1cc(C)n2ccc(C(=O)Nc3ccc(N(C)C)cc3)c2n1] |
| 18 | 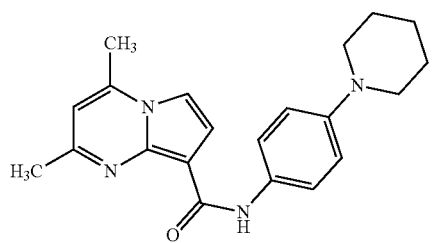 [SMILES: Cc1cc(C)n2ccc(C(=O)Nc3ccc(N4CCCCC4)cc3)c2n1] |
| 19 | 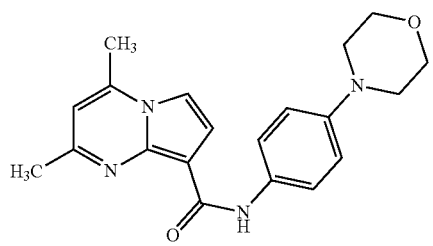 [SMILES: Cc1cc(C)n2ccc(C(=O)Nc3ccc(N4CCOCC4)cc3)c2n1] |
| 20 | 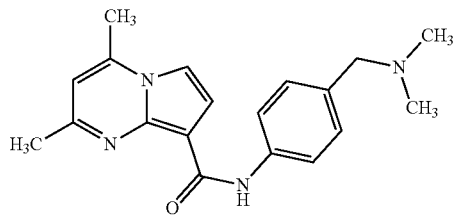 |

TABLE 1-continued
21
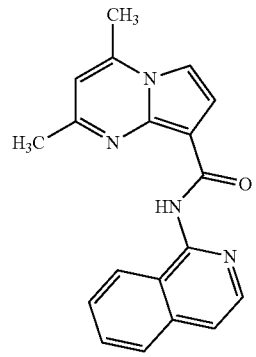 [SMILES: Cc1cc(C)n2ccc(C(=O)Nc3nccc4ccccc34)c2n1]
22
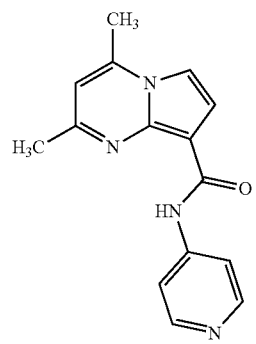 [SMILES: Cc1cc(C)n2ccc(C(=O)Nc3ccncc3)c2n1]
23
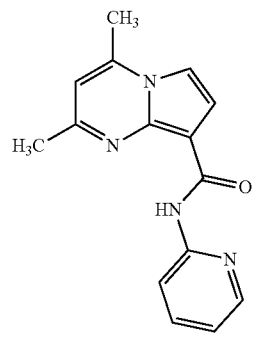 [SMILES: Cc1cc(C)n2ccc(C(=O)Nc3ccccn3)c2n1]
24
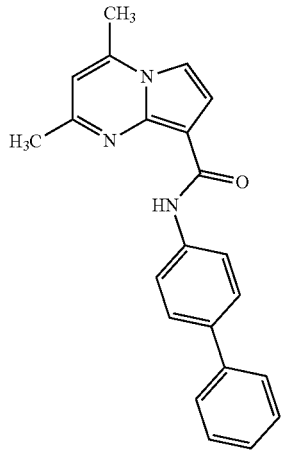 [SMILES: Cc1cc(C)n2ccc(C(=O)Nc3ccc(-c4ccccc4)cc3)c2n1]

TABLE 1-continued
25
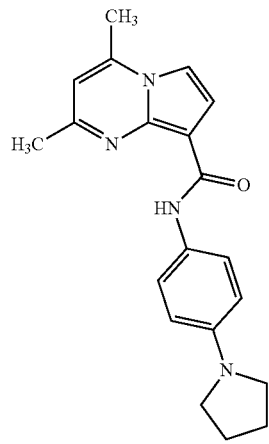 [SMILES: Cc1cc(C)n2ccc(C(=O)Nc3ccc(N4CCCC4)cc3)c2n1]
26
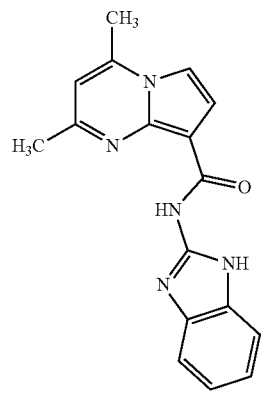 [SMILES: Cc1cc(C)n2ccc(C(=O)Nc3nc4ccccc4[nH]3)c2n1]
27
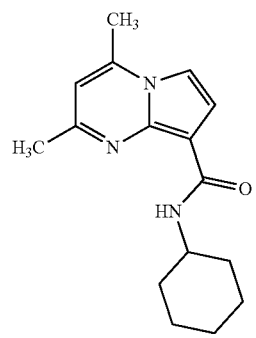 [SMILES: Cc1cc(C)n2ccc(C(=O)NC3CCCCC3)c2n1]
28
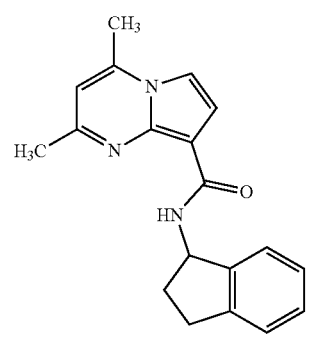 [SMILES: Cc1cc(C)n2ccc(C(=O)NC3CCc4ccccc43)c2n1]

TABLE 1-continued
| | |
|---|---|
| 29 | 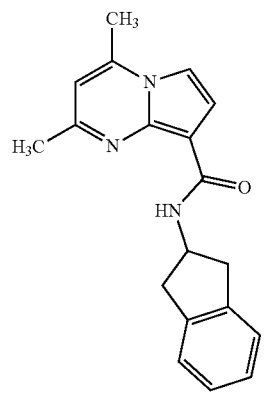 [SMILES: Cc1cc(C)n2ccc(C(=O)NC3Cc4ccccc4C3)c2n1] |
| 30 | 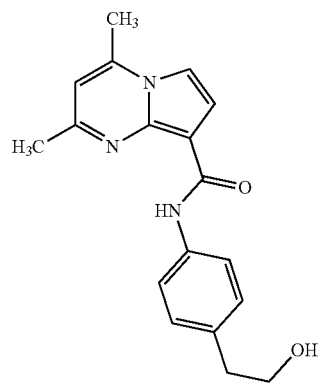 [SMILES: Cc1cc(C)n2ccc(C(=O)Nc3ccc(CCO)cc3)c2n1] |
| 31 | 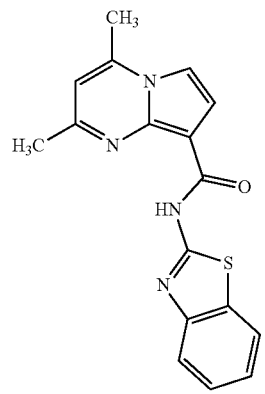 [SMILES: Cc1cc(C)n2ccc(C(=O)Nc3nc4ccccc4s3)c2n1] |
| 32 | 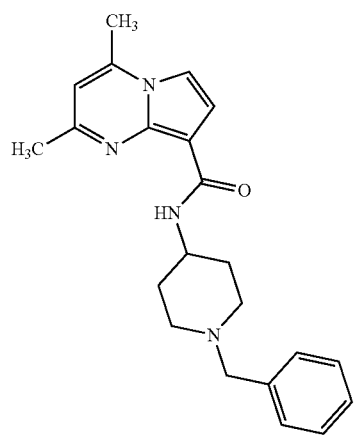 [SMILES: Cc1cc(C)n2ccc(C(=O)NC3CCN(Cc4ccccc4)CC3)c2n1] |

TABLE 1-continued
33
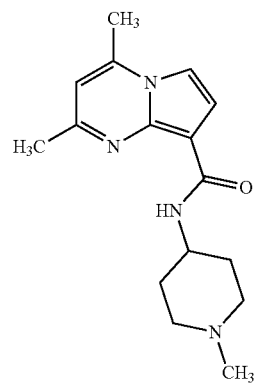 [SMILES: Cc1cc(C)n2ccc(C(=O)NC3CCN(C)CC3)c2n1]
34
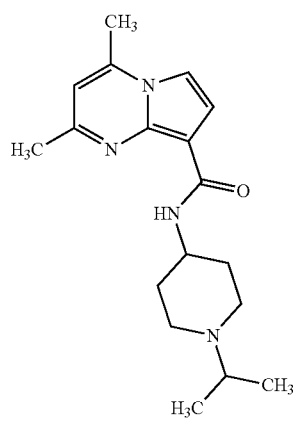 [SMILES: Cc1cc(C)n2ccc(C(=O)NC3CCN(C(C)C)CC3)c2n1]
35
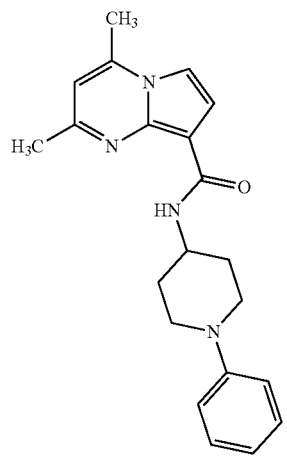 [SMILES: Cc1cc(C)n2ccc(C(=O)NC3CCN(c4ccccc4)CC3)c2n1]

TABLE 1-continued
36 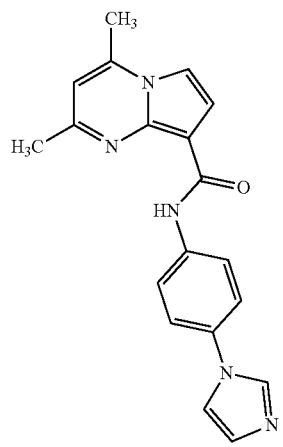 [SMILES: Cc1cc(C)n2ccc(C(=O)Nc3ccc(-n4ccnc4)cc3)c2n1]
37 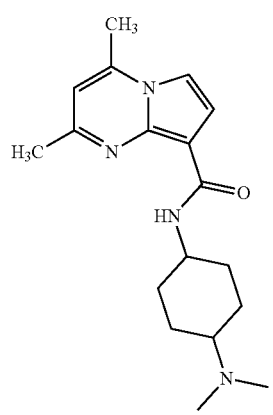
38 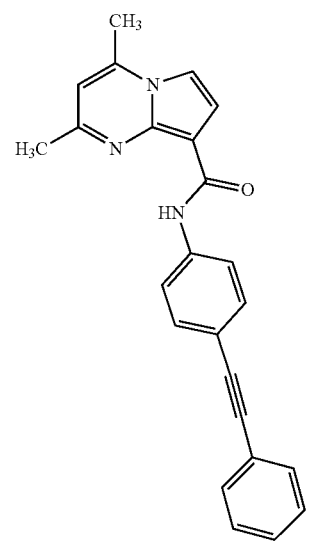 [SMILES: Cc1cc(C)n2ccc(C(=O)Nc3ccc(C#Cc4ccccc4)cc3)c2n1]

TABLE 1-continued
| 39 | 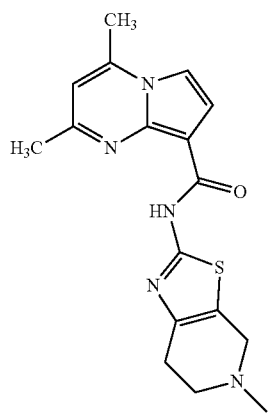 |
| --- | --- |
| 40 | 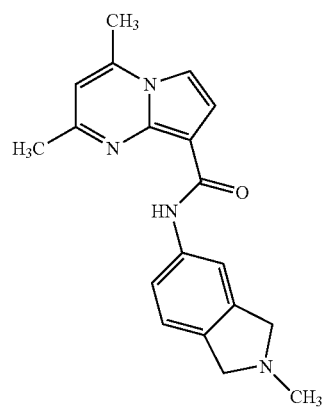 |
| 41 | 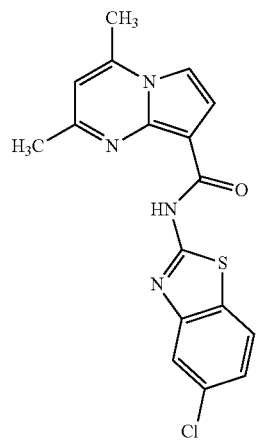 [SMILES: Cc1cc(C)n2ccc(C(=O)Nc3nc4cc(Cl)ccc4s3)c2n1] |

TABLE 1-continued
| 42 | 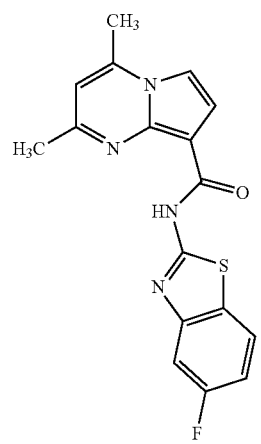 [SMILES: Cc1cc(C)n2ccc(C(=O)Nc3nc4cc(F)ccc4s3)c2n1] |
| --- | --- |
| 43 | 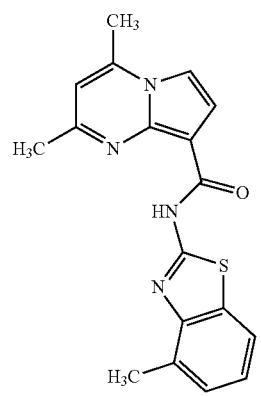 [SMILES: Cc1cc(C)n2ccc(C(=O)Nc3nc4c(C)cccc4s3)c2n1] |
| 44 | 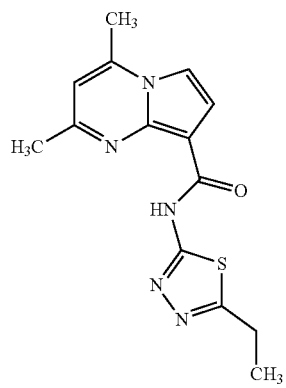 [SMILES: CCc1nnc(NC(=O)c2ccn3c(C)cc(C)nc23)s1] |
| 45 | 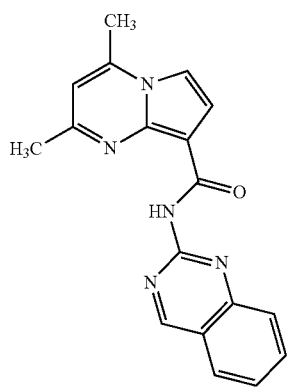 [SMILES: Cc1cc(C)n2ccc(C(=O)Nc3ncc4ccccc4n3)c2n1] |

TABLE 1-continued
46
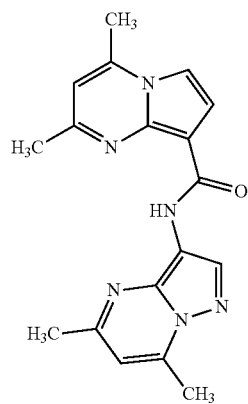
47
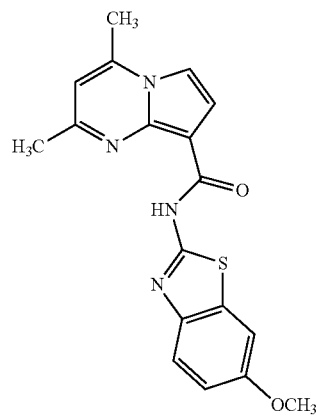 [SMILES: COc1ccc2nc(NC(=O)c3ccn4c(C)cc(C)nc34)sc2c1]
48
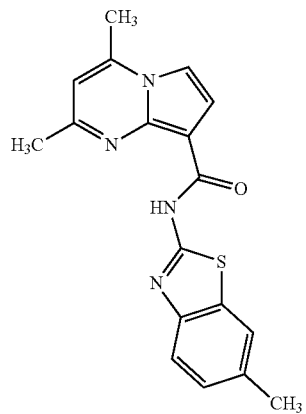
49
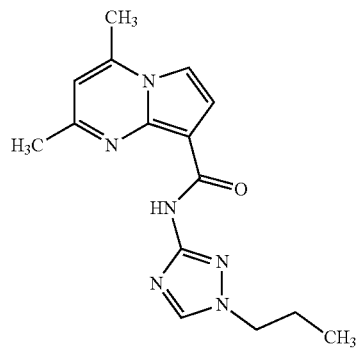 [SMILES: CCCn1cnc(NC(=O)c2ccn3c(C)cc(C)nc23)n1]

TABLE 1-continued
| | |
|---|---|
| 50 | 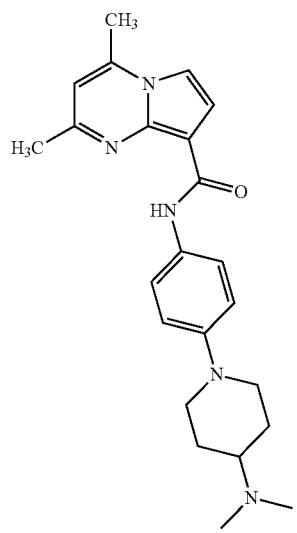 |
| 51 | 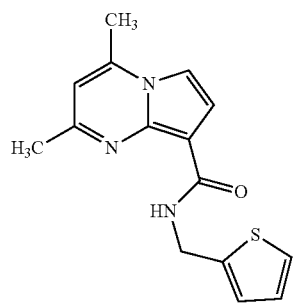 [SMILES: Cc1cc(C)n2ccc(C(=O)NCc3cccs3)c2n1] |
| 52 | 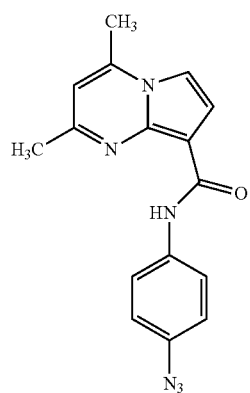 [SMILES: Cc1cc(C)n2ccc(C(=O)Nc3ccc(N=[N+]=[N-])cc3)c2n1] |

TABLE 1-continued
| 53 | 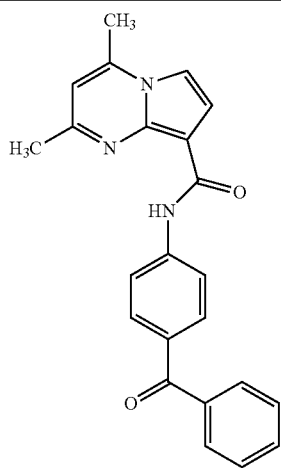 |
| --- | --- |
| 54 | 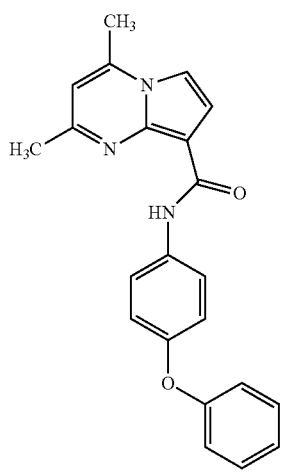 [SMILES: Cc1cc(C)n2ccc(C(=O)Nc3ccc(Oc4ccccc4)cc3)c2n1] |
| 55 | 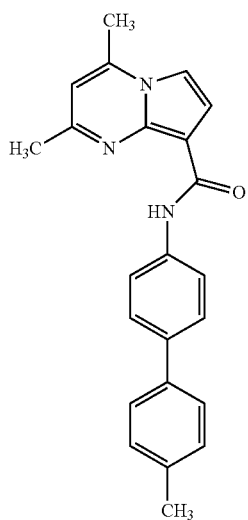 [SMILES: Cc1ccc(-c2ccc(NC(=O)c3ccn4c(C)cc(C)nc34)cc2)cc1] |

TABLE 1-continued
| | |
|---|---|
| 56 | 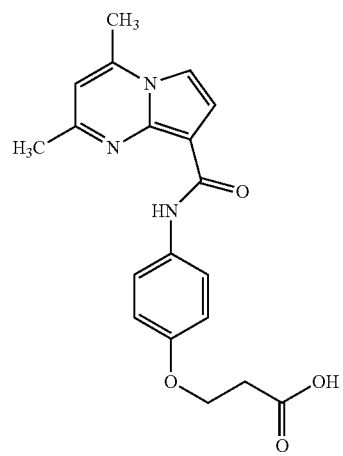 [SMILES: Cc1cc(C)n2ccc(C(=O)Nc3ccc(OCCC(=O)O)cc3)c2n1] |
| 57 | 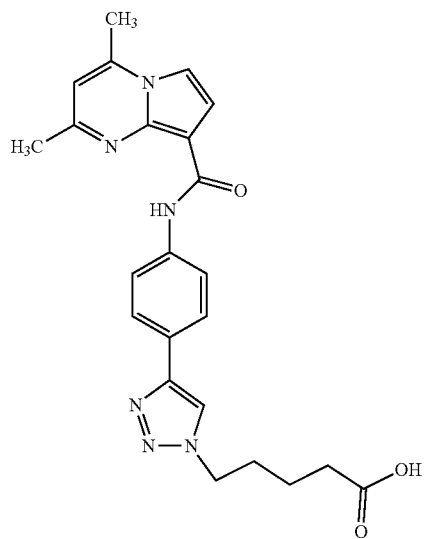 [SMILES: Cc1cc(C)n2ccc(C(=O)Nc3ccc(-c4cn(CCCCC(=O)O)nn4)cc3)c2n1] |
| 58 | 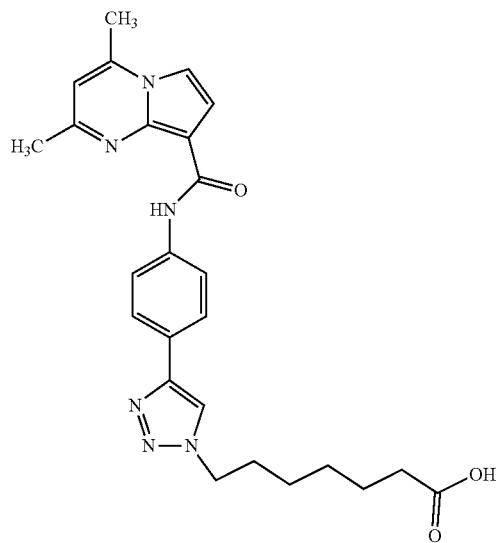 [SMILES: Cc1cc(C)n2ccc(C(=O)Nc3ccc(-c4cn(CCCCCCC(=O)O)nn4)cc3)c2n1] |

TABLE 1-continued
59 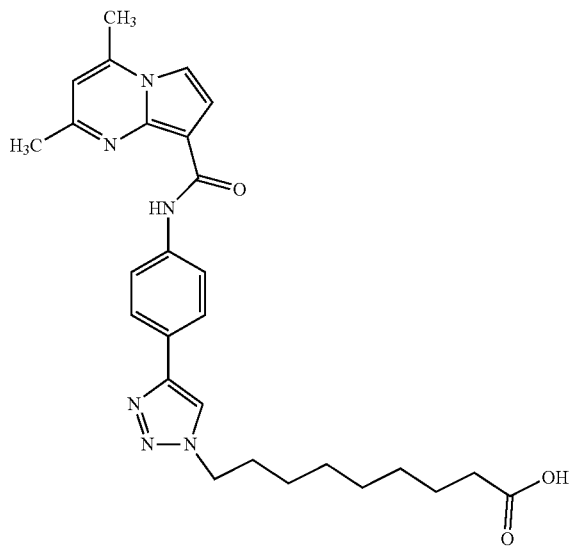 [SMILES: Cc1cc(C)n2ccc(C(=O)Nc3ccc(-c4cn(CCCCCCCCC(=O)O)nn4)cc3)c2n1]
60 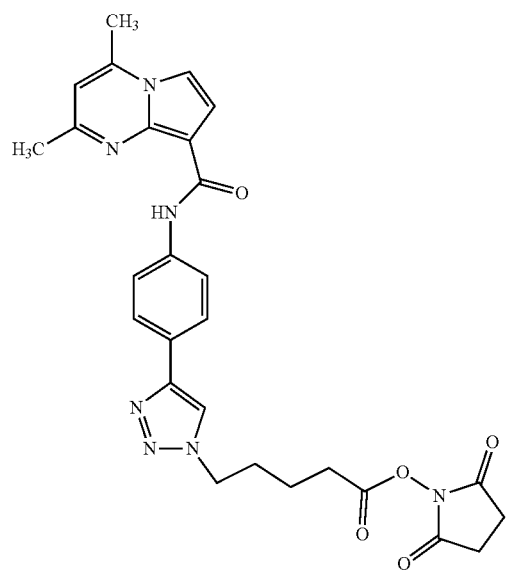 [SMILES: Cc1cc(C)n2ccc(C(=O)Nc3ccc(-c4cn(CCCCC(=O)ON5C(=O)CCC5=O)nn4)cc3)c2n1]

TABLE 1-continued
61
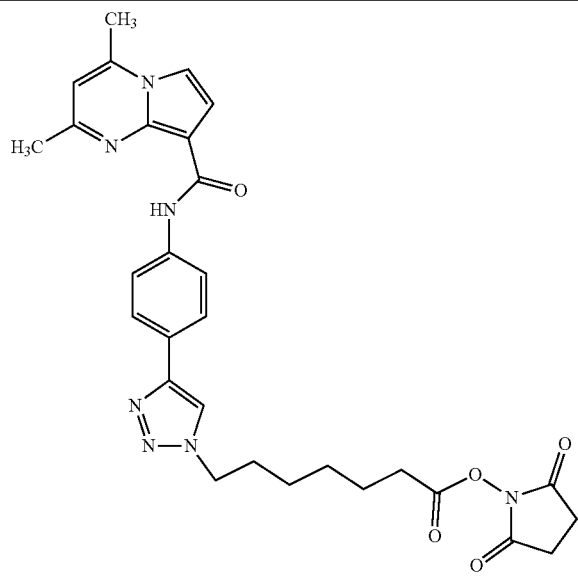
(6:1 isomer mixture)
62
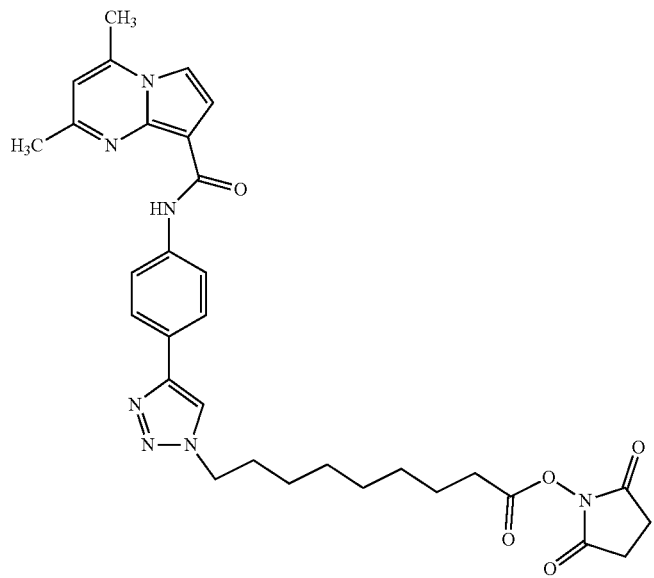 [SMILES: Cc1cc(C)n2ccc(C(=O)Nc3ccc(-c4cn(CCCCCCCCC(=O)ON5C(=O)CCC5=O)nn4)cc3)c2n1]

TABLE 1-continued
63 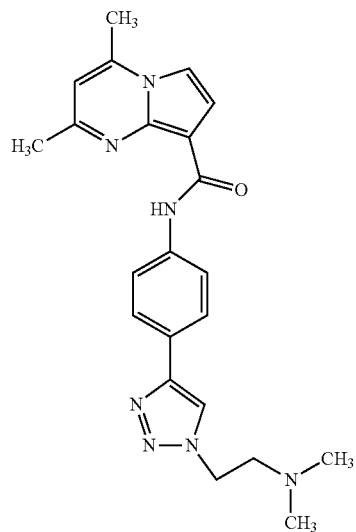
64 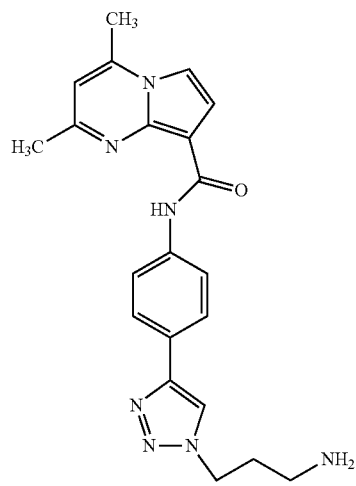 [SMILES: Cc1cc(C)n2ccc(C(=O)Nc3ccc(-c4cn(CCCN)nn4)cc3)c2n1]
65 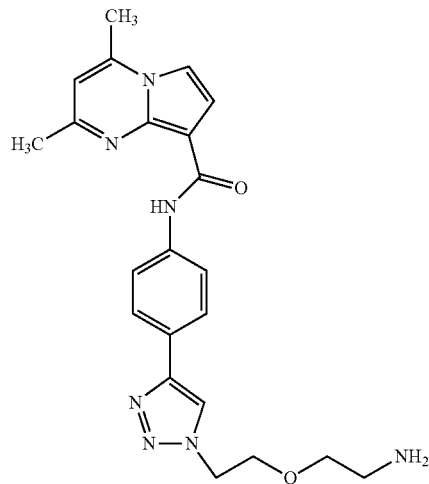
(4:1 isomer mixture)

TABLE 1-continued
66 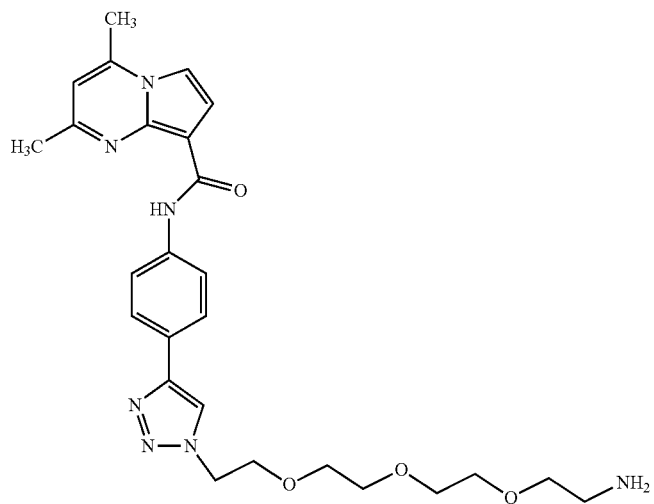 [SMILES: Cc1cc(C)n2ccc(C(=O)Nc3ccc(-c4cn(CCOCCOCCOCCN)nn4)cc3)c2n1]
67 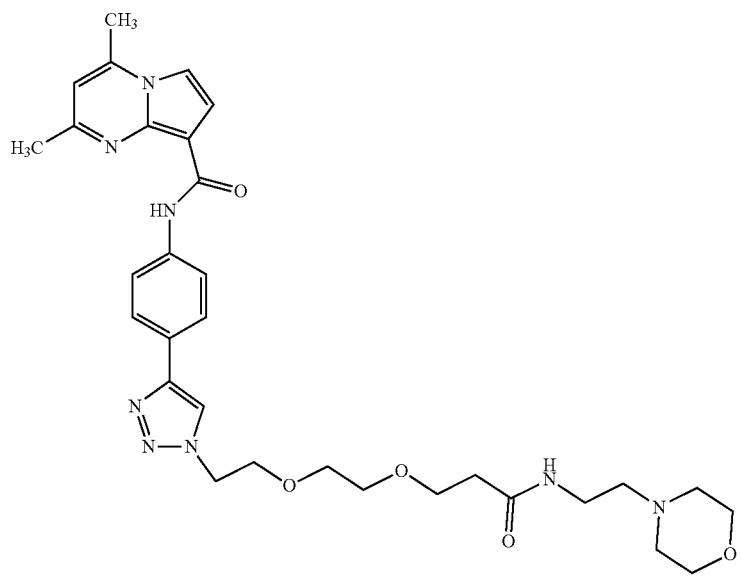 [SMILES: Cc1cc(C)n2ccc(C(=O)Nc3ccc(-c4cn(CCOCCOCCC(=O)NCCN5CCOCC5)nn4)cc3)c2n1]
68 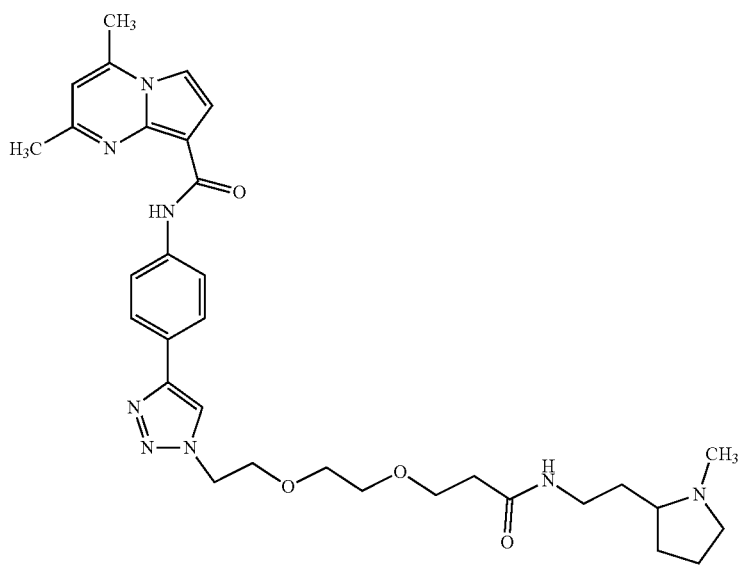 [SMILES: Cc1cc(C)n2ccc(C(=O)Nc3ccc(-c4cn(CCOCCOCCC(=O)NCCC5CCCN5C)nn4)cc3)c2n1]

TABLE 1-continued

| No. | MW | AC$_{50}$ (μM) | $^1$H NMR | $^{13}$C NMR | Mass |
|---|---|---|---|---|---|
| 1 | 289 | 0.14 | $^1$H NMR: (500 MHz, CDCl$_3$) δ (ppm): 10.87 (s, 1H), 7.74 (d, J = 8.6 Hz, 2H), 7.56 (d, J = 3.3 Hz, 1H), 7.48 (d, J = 8.6 Hz, 2H), 7.07 (d, J = 3.3 Hz, 1H), 6.53 (s, 1H), 3.04 (s, 1H), 2.63 (s, 3H), 2.58 (s, 3H). | $^{13}$C NMR: (125 MHz, CDCl$_3$) δ (ppm): 162.5, 155.7, 142.7, 140.3, 139.6, 133.0, 119.0, 117.3, 116.0, 108.5, 107.2, 105.6, 84.1, 76.2, 24.8, 18.3. | ESI-MS m/z: 312 (M + Na)$^+$. |
| 2 | 589 | 3.98 | $^1$H NMR: (500 MHz, CDCl$_3$) δ (ppm): 10.82 (s, 1H), 7.95 (s, 1H), 7.83 (s, 4H), 7.56 (d, J = 3.3 Hz, 1H), 7.06 (d, J = 3.4 Hz, 1H), 6.52 (s, 1H), 4.59 (t, J = 5.0 Hz, 2H), 3.91 (t, J = 5.1 Hz, 2H), 3.83 (t, J = 6.0 Hz, 2H), 3.64 (s, 4H), 2.86 (t, J = 6.0 Hz, 2H), 2.78 (s, 4H), 2.64 (s, 3H), 2.57 (s, 3H). | $^{13}$C NMR: (125 MHz, CDCl$_3$) δ (ppm): 169.1, 166.9, 162.4, 155.7, 147.7, 142.6, 139.6, 139.5, 126.4, 125.6, 120.6, 119.6, 117.2, 108.4, 107.0, 105.8, 70.9, 70.6, 32.4, 25.7, 24.8, 18.3. | ESI-MS m/z: 590 (M + H)$^+$ |

TABLE 1-continued

| | | | ¹H NMR | ¹³C NMR | MS |
|---|---|---|---|---|---|
| 3 | 463 | 6.31 | ¹H NMR: (500 MHz, CDCl₃) δ (ppm): 10.82 (s, 1H), 7.92 (s, 1H), 7.83 (d, J = 8.6 Hz, 2H), 7.80 (d, J = 8.6 Hz, 2H), 7.55 (d, J = 3.2 Hz, 1H), 7.05 (d, J = 3.2 Hz, 1H), 6.51 (s, 1H), 4.57 (t, J = 5.0 Hz, 2H), 3.90 (t, J = 5.1 Hz, 2H), 3.63-3.54 (m, 4H), 3.45 (t, J = 5.2 Hz, 2H), 2.82 (t, J = 5.2 Hz, 2H), 2.63 (s, 3H), 2.56 (s, 3H), 2.15 (br, 2H) | ¹³C NMR: (125 MHz, CDCl₃) δ (ppm): 162.5, 155.6, 147.8, 142.6, 139.6, 139.5, 128.2, 126.4, 125.5, 120.4, 119.6, 119.3, 117.3, 108.4, 107.1, 105.9, 73.5, 70.8, 70.3, 69.7, 50.4, 41.8, 24.8, 18.3. | ESI-MS m/z: 464 (M + H)⁺ |
| 4 | 875 | Kd = 0.79 | ¹H NMR: (500 MHz, CDCl₃) δ (ppm): 10.84 (s, 1H), 8.35 (s, 1H), 8.19 (dd, J = 8.0, 1.2 Hz, 1H), 7.92 (s, 1H), 7.84 (d, J = 8.6 Hz, 2H), 7.79 (d, J = 8.6 Hz, 2H), 7.57 (d, J = 3.3 Hz, 1H), 7.24 (d, J = 8.0 Hz, 1H), 7.10 (t, J = 4.9 Hz, 1H), 7.07 (d, J = 3.3 Hz, 1H), 6.55 (d, J = 8.0 Hz, 2H), 6.53 (s, 1H), 6.46 (d, J = 2.4 Hz, 2H), 6.35 (dd, J = 8.9, 2.5 Hz, 2H), 4.64 (t, J = 5.1 Hz, 2H), 4.02 (t, J = 5.1 Hz, 2H), 3.71-3.61 (m, 8H), 2.96 (s, 12H), 2.64 (s, 3H), 2.59 (s, 3H). | ¹³C NMR: (125 MHz, CDCl₃) δ (ppm): 169.2, 166.2, 162.5, 155.7, 153.1, 152.3, 147.8, 142.6, 139.7, 139.5, 136.3, 134.4, 128.8, 128.2, 126.4, 125.3, 124.8, 123.0, 120.5, 119.7, 117.3, 108.9, 108.5, 107.1, 106.3, 105.8, 98.5, 70.6, 70.5, 69.6, 50.4, 40.3, 40.1, 24.8, 18.3. | ESI-MS m/z: 898 (M + Na)⁺, 876 (M + H)⁺. |
| 5 | 333 | 0.8 | ¹H NMR (500 MHz, CDCl₃) δ 10.99 (s, 1H), 7.87 (d, J = 8.5 Hz, 2H), 7.59 (d, J = 8.5 Hz, 2H), 7.56 (d, J = 3.3 Hz, 1H), 7.08 (d, J = 3.3 Hz, 1H), 6.55 (s, 1H), 2.64 (s, 3H), 2.59 (s, 3H). | ¹³C NMR: (125 MHz, CDCl₃) 162.6, 155.9, 142.8, 142.8, 139.7, 126.2 (q, $J_{C\text{-}F}$ = 3.6 Hz), 124.6 (q, $J_{C\text{-}F}$ = 33.7 Hz), 124.5 (q, $J_{C\text{-}F}$ = 270 Hz), 118.9, 117.3, 108.6, 107.3, 105.4, 77.4, 77.1, 76.9, 24.8, 18.3, | ESI-MS m/z: 356 (M + Na)⁺, 334 (M + H)⁺ |
| 6 | 302 | NA | ¹H NMR (500 MHz, CDCl₃) δ 8.80 (s, 1H), 7.51 (d, J = 3.2 Hz, 1H), 7.02 (d, J = 3.3 Hz, 1H), 6.47 (s, 1H), 3.77 (s, 4H), 3.67 (d, J = 5.7 Hz, 2H), 2.65 (s, 2H), 2.57 (d, J = 10.9 Hz, 10H). | ¹³C NMR: (125 MHz, CDCl₃) δ 164.6, 155.1, 142.2, 139.5, 117.3, 108.1, 106.5, 105.9, 67.3, 57.9, 53.7, 35.9, 24.9, 18.3. | ESI-MS m/z: 303 (M + H)⁺ |
| 7 | 364 | 112.2 | ¹H NMR (500 MHz, CDCl₃) δ 10.75 (s, 1H), 7.73 (d, J = 8.4 Hz, 2H), 7.55 (d, J = 3.2 Hz, 1H), 7.30 (d, J = 8.3 Hz, 2H), 7.05 (d, J = 3.2 Hz, 1H), 6.51 (s, 1H), 3.71 (t, J = 4.6 Hz, 4H), 3.48 (s, 2H), 2.61 (s, 3H), 2.57 (s, 3H), 2.46 (s, 4H). | ¹³C NMR: (125 MHz, CDCl₃) δ 162.3, 155.4, 142.5, 139.3, 138.6, 132.0, 129.8, 119.3, 117.1, 108.3, 106.9, 105.7, 67.0, 63.1, 53.5, 24.7, 18.2. | ESI-MS m/z: 387 (M + Na)⁺, 365 (M + H)⁺ |
| 8 | 377 | 39.81 | ¹H NMR (500 MHz, CDCl₃) δ 10.74 (s, 1H), 7.72 (d, J = 8.4 Hz, 2H), 7.58 (d, J = 3.2 Hz, 1H), 7.30 (d, J = 8.4 Hz, 2H), 7.07 (d, J = 3.3 Hz, 1H), 6.52 (s, 1H), 3.49 (s, 2H), 2.62 (s, 3H), 2.59 (s, 3H), 2.45 (brs, 5H), 2.28 (s, 3H), 1.73 (m, 3H). | ¹³C NMR: (125 MHz, CDCl₃) 162.3, 155.4, 142.5, 139.2, 138.5, 132.5, 129.8, 119.2, 117.0, 108.2, 106.8, 105.6, 62.7, 55.1, 53.0, 46.0, 24.6, 18.1, | ESI-MS m/z: 400 (M + Na)⁺, 378 (M + H)⁺ |

TABLE 1-continued

| | | | | | |
|---|---|---|---|---|---|
| 9 | 362 | 70.79 | ¹H NMR (500 MHz, CDCl₃) δ 10.71 (s, 1H), 7.71 (d, J = 8.3 Hz, 2H), 7.53 (dd, J = 3.1, 0.8 Hz, 1H), 7.29 (d, J = 8.3 Hz, 2H), 7.02 (d, J = 2.4 Hz, 1H), 6.48 (s, 1H), 3.46 (s, 2H), 2.59 (s, 3H), 2.54 (s, 3H), 2.38 (s, 4H), 1.57 (p, J = 5.6 Hz, 4H), 1.42 (s, 2H). | ¹³C NMR: (125 MHz, CDCl₃) 162.3, 155.3, 142.4, 139.2, 138.3, 132.8, 129.9, 119.1, 117.1, 108.2, 106.8, 105.7, 63.5, 54.3, 25.9, 24.6, 24.4, 18.1 | ESI-MS m/z: 363 (M + H)⁺ |
| 10 | 363 | 7.08 | ¹H NMR (500 MHz, CDCl₃) δ 10.59 (s, 1H), 7.68 (d, J = 8.8 Hz, 2H), 7.57 (d, J = 3.2 Hz, 1H), 7.06 (d, J = 3.2 Hz, 1H), 6.96 (d, J = 8.9 Hz, 2H), 6.50 (s, 1H), 3.22-3.14 (m, 4H), 2.64-2.55 (m, 10H), 2.36 (s, 3H). | ¹³C NMR: (125 MHz, CDCl₃) 162.2, 155.3, 147.4, 142.4, 139.3, 132.6, 120.7, 117.3, 117.0, 108.2, 106.8, 106.1, 55.3, 50.0, 46.3, 24.8, 18.3 | ESI-MS m/z: 364 (M + H)⁺ |
| 11 | 377 | 31.62 | ¹H NMR (500 MHz, CDCl₃) δ 10.57 (s, 1H), 7.67 (d, J = 7.6 Hz, 2H), 7.54 (s, 1H), 7.03 (s, 1H), 6.96 (d, J = 7.6 Hz, 2H), 6.48 (s, 1H), 3.19 (s, 4H), 2.76-2.39 (m, 12H), 1.13 (s, 3H). | ¹³C NMR: (125 MHz, CDCl₃) 162.2, 155.3, 147.5, 142.4, 139.2, 132.5, 120.7, 117.2, 117.0, 108.2, 106.8, 106.0, 53.0, 52.5, 50.0, 24.7, 18.2, 12.1, | ESI-MS m/z: 378 (M + H)⁺ |
| 12 | 439 | 5.01 | ¹H NMR (500 MHz, CDCl₃) δ 10.58 (s, 1H), 7.67 (d, J = 8.9 Hz, 2H), 7.55 (d, J = 2.9 Hz, 1H), 7.38-7.31 (m, 4H), 7.28 (d, J = 7.0 Hz, 1H), 7.04 (t, J = 3.1 Hz, 1H), 6.95 (d, J = 9.0 Hz, 2H), 6.49 (s, 1H), 3.58 (s, 2H), 3.24-3.10 (m, 4H), 2.66-2.61 (m, 4H), 2.59 (s, 3H), 2.56 (s, 3H). | ¹³C NMR: (125 MHz, CDCl₃) 162.2, 155.2, 147.5, 142.4, 139.2, 138.1, 132.5, 129.3, 128.3, 127.2, 120.7, 117.2, 117.0, 108.2, 106.8, 106.0, 63.2, 53.2, 50.0, 24.7, 18.3 | ESI-MS m/z: 440 (M + H)⁺ |
| 13 | 355 | 0.79 | ¹H NMR (500 MHz, CDCl₃) δ 10.71 (s, 1H), 7.70 (d, J = 8.3 Hz, 2H), 7.56 (d, J = 3.2 Hz, 1H), 7.31-7.26 (m, 2H), 7.24-7.13 (m, 5H), 7.04 (d, J = 3.2 Hz, 1H), 6.50 (s, 1H), 3.98 (s, 2H), 2.59 (s, 3H), 2.56 (s, 3H). | ¹³C NMR: (125 MHz, CDCl₃) 162.4, 155.4, 142.5, 141.6, 139.4, 137.7, 135.7, 129.5, 129.0, 128.5, 126.0, 119.7, 117.2, 108.3, 106.9, 105.9, 41.5, 24.7, 18.2 | ESI-MS m/z: 378 (M + Na)⁺, 356 (M + H)⁺ |
| 14 | 378 | 31.62 | ¹H NMR (500 MHz, CDCl₃) δ 10.71 (s, 1H), 7.70 (d, J = 8.2 Hz, 2H), 7.59-7.53 (m, 1H), 7.19 (d, J = 8.2 Hz, 2H), 7.08-7.02 (m, 1H), 6.51 (s, 1H), 3.75 (t, J = 4.4 Hz, 4H), 2.83-2.76 (m, 2H), 2.61 (s, 3H), 2.60 (s, 2H), 2.57 (s, 3H), 2.53 (s, 4H). | ¹³C NMR: (125 MHz, CDCl₃) 162.4, 155.4, 142.5, 139.4, 137.8, 134.7, 129.1, 119.7, 117.3, 108.3, 106.9, 105.9, 67.1, 61.1, 53.8, 32.9, 24.8, 18.3 | ESI-MS m/z: 379 (M + H)⁺ |
| 15 | 376 | 39.81 | ¹H NMR (500 MHz, CDCl₃) δ 10.70 (s, 1H), 7.69 (d, J = 8.2 Hz, 2H), 7.57 (d, J = 3.2 Hz, 1H), 7.19 (d, J = 8.2 Hz, 2H), 7.06 (d, J = 3.2 Hz, 1H), 6.51 (s, 1H), 2.83-2.76 (m, 2H), 2.61 (s, 3H), 2.58 (s, 3H), 2.56-2.39 (m, 6H), 1.68-1.57 (m, 4H), 1.46 (brs, 2H). | ¹³C NMR: (125 MHz, CDCl₃) 162.4, 155.4, 142.5, 139.4, 137.6, 135.3, 129.2, 119.6, 117.3, 108.3, 106.9, 106.0, 61.7, 54.7, 33.2, 26.1, 24.8, 24.6, 18.3 | ESI-MS m/z: 377 (M + H)⁺ |

TABLE 1-continued

| 16 | 391 | 44.67 | ¹H NMR (500 MHz, CDCl₃) δ 10.72 (s, 1H), 7.64 (d, J = 8.1 Hz, 2H), 7.48 (d, J = 2.9 Hz, 1H), 7.16 (d, J = 8.1 Hz, 2H), 7.05 (d, J = 3.1 Hz, 1H), 6.51 (s, 1H), 2.98-2.64 (m, 12H), 2.59 (s, 3H), 2.55 (s, 6H). | ¹³C NMR: (125 MHz, CDCl₃) 162.5, 155.8, 142.7, 139.5, 137.8, 133.9, 129.1, 119.9, 117.0, 108.5, 107.1, 105.4, 59.4, 53.9, 51.1, 44.6, 32.3, 24.7, 18.2, | ESI-MS m/z: 392 (M + H)⁺ |
|---|---|---|---|---|---|
| 17 | 308 | 3.55 | ¹H NMR (500 MHz, CD₃OD) δ 7.55 (d, J = 8.9 Hz, 2H), 7.44 (d, J = 3.2 Hz, 1H), 7.34 (d, J = 3.2 Hz, 1H), 6.85 (d, J = 8.9, Hz, 2H), 6.77 (s, 1H), 2.94 (s, 6H), 2.66 (s, 3H), 2.65 (s, 3H). | ¹³C NMR: (125 MHz, CD₃OD) 164.6, 158.0, 149.2, 145.2, 141.0, 130.5, 122.3, 117.0, 114.9, 109.5, 109.0, 105.3, 41.5, 24.6, 18.0, | ESI-MS m/z: 309 (M + H)⁺ |
| 18 | 348 | 1.58 | ¹H NMR (500 MHz, CDCl₃) δ 10.58 (s, 1H), 7.66 (d, J = 8.9 Hz, 2H), 7.58 (d, J = 3.2 Hz, 1H), 7.07 (d, J = 3.2 Hz, 1H), 6.97 (d, J = 8.9 Hz, 2H), 6.51 (s, 1H), 3.11 (t, J = 5.5 Hz, 4H), 2.61 (s, 3H), 2.58 (s, 3H), 1.77-1.69 (m, 4H), 1.64-1.53 (m, 2H). | ¹³C NMR: (125 MHz, CDCl₃) 162.2, 155.2, 148.6, 142.4, 139.3, 132.2, 120.7, 117.6, 117.3, 108.2, 106.8, 106.1, 51.7, 26.1, 24.8, 24.4, 18.3, | ESI-MS m/z: 349 (M + H)⁺ |
| 19 | 350 | 1.41 | ¹H NMR (500 MHz, CDCl₃) δ 10.62 (s, 1H), 7.70 (d, J = 8.9 Hz, 2H), 7.58 (d, J = 3.2 Hz, 1H), 7.07 (d, J = 3.2 Hz, 1H), 6.94 (d, J = 8.9 Hz, 2H), 6.52 (s, 1H), 3.88 (t, J = 4.7 Hz, 4H), 3.13 (t, J = 4.7 Hz, 4H), 2.62 (s, 3H), 2.59 (s, 3H). | ¹³C NMR: (125 MHz, CDCl₃) 162.1, 155.2, 147.2, 142.4, 139.2, 132.8, 120.7, 117.2, 116.6, 108.2, 106.7, 105.9, 67.0, 50.2, 24.7, 18.2, | ESI-MS m/z: 373 (M + Na)⁺, 351 (M + H)⁺ |
| 20 | 322 | 14.13 | ¹H NMR (500 MHz, CDCl₃) δ 10.84 (s, 1H), 7.75 (d, J = 8.3 Hz, 2H), 7.54 (d, J = 3.2 Hz, 1H), 7.35 (d, J = 8.3 Hz, 2H), 7.09 (d, J = 3.3 Hz, 1H), 6.55 (s, 1H), 3.64 (s, 2H), 2.63 (s, 3H), 2.60 (s, 3H), 2.42 (s, 6H). | ¹³C NMR: (125 MHz, CDCl₃) 162.7, 155.8, 142.7, 139.6, 139.3, 130.5, 119.7, 117.2, 108.5, 107.2, 105.5, 63.3, 44.5, 24.8, 18.3, | ESI-MS m/z: 323 (M + H)⁺ |
| 21 | 316 | 39.8 | ¹H NMR (500 MHz, CDCl₃) δ 11.57 (s, 1H), 8.46 (d, J = 8.5 Hz, 1H), 8.43 (d, J = 5.7 Hz, 1H), 7.81 (d, J = 8.1 Hz, 1H), 7.68 (t, J = 7.1 Hz, 1H), 7.63 (d, J = 3.3 Hz, 1H), 7.59 (t, J = 7.2 Hz, 1H), 7.44 (d, J = 5.7 Hz, 1H), 7.08 (d, J = 3.3 Hz, 1H), 6.54 (s, 1H), 2.65 (s, 3H), 2.58 (s, 3H). . | ¹³C NMR: (125 MHz, CDCl₃) 161.9, 155.9, 150.5, 142.9, 141.5, 140.0, 137.8, 130.2, 127.1, 126.8, 124.6, 122.1, 117.7, 117.5, 108.6, 107.3, 106.0, 24.5, 18.3, | ESI-MS m/z: 317 (M + H)⁺ |
| 22 | 266 | 25.12 | ¹H NMR (500 MHz, CDCl₃) δ 10.97 (s, 1H), 8.47 (dd, J = 5.0, 1.3 Hz, 2H), 7.64 (dd, J = 4.9, 1.4 Hz, 2H), 7.51 (d, J = 3.3 Hz, 1H), 7.05 (d, J = 3.3 Hz, 1H), 6.53 (s, 1H), 2.62 (s, 3H), 2.57 (s, 3H). | ¹³C NMR: (125 MHz, CDCl₃) 218.4, 162.9, 156.2, 150.5, 146.4, 143.0, 139.9, 117.2, 113.4, 108.7, 107.5, 105.1, 24.8, 18.3, | ESI-MS m/z: 267 (M + H)⁺ |
| 23 | 266 | 22.39 | ¹H NMR (500 MHz, CDCl₃) δ 11.16 (s, 1H), 8.44 (d, J = 8.4 Hz, 1H), 8.34 (d, J = 4.7 Hz, 1H), 7.70 (s, 1H), 7.55 (d, J = 3.2 Hz, 1H), 7.06 (d, J = 3.2 Hz, 1H), 7.02-6.92 (m, 1H), 6.51 (s, 1H), 2.66 (s, 3H), 2.56 (s, 3H). | ¹³C NMR: (125 MHz, CDCl₃) 162.7, 156.3, 152.9, 148.0, 142.5, 139.9, 138.0, 118.7, 117.2, 114.4, 108.7, 107.2, 105.2, 24.9, 18.2, | ESI-MS m/z: 289 (M + Na)⁺, 267 (M + H)⁺ |

TABLE 1-continued

| | | | ¹H NMR | ¹³C NMR | MS |
|---|---|---|---|---|---|
| 24 | 341 | 1.41 | ¹H NMR (500 MHz, CDCl₃) δ 10.84 (s, 1H), 7.87 (d, J = 8.6 Hz, 2H), 7.67-7.54 (m, 5H), 7.47-7.39 (m, 2H), 7.32 (t, J = 7.4 Hz, 1H), 7.09 (d, J = 3.2 Hz, 1H), 6.54 (s, 1H), 2.65 (s, 3H), 2.60 (s, 3H) | ¹³C NMR: (125 MHz, CDCl₃) 162.5, 155.6, 142.6, 141.0, 139.4, 139.1, 135.6, 128.8, 127.6, 126.8, 119.7, 117.2, 117.2, 108.4, 107.0, 105.8, 24.8, 18.2, | ESI-MS m/z: 364 (M + Na)⁺, 342 (M + H)⁺ |
| 25 | 334 | 0.51 | ¹H NMR (500 MHz, CDCl₃) δ 10.47 (s, 1H), 7.63 (d, J = 8.9 Hz, 2H), 7.57 (d, J = 3.2 Hz, 1H), 7.05 (d, J = 3.3 Hz, 1H), 6.59 (d, J = 8.9 Hz, 2H), 6.49 (s, 1H), 3.29 (t, J = 6.5 Hz, 4H), 2.60 (s, 3H), 2.57 (s, 3H), 2.03-1.98 (m, 4H). | ¹³C NMR: (125 MHz, CDCl₃) 162.0, 155.1, 144.8, 142.3, 139.1, 128.7, 121.5, 117.3, 111.9, 108.1, 106.6, 106.3, 77.4, 77.1, 76.9, 48.0, 25.5, 24.7, 18.3, | ESI-MS m/z: 335 (M + H)⁺ |
| 26 | 305 | 1.26 | ¹H NMR (500 MHz, d6-DMSO) δ 12.17 (s, 1H), 11.52 (s, 1H), 7.57-7.50 (m, 2H), 7.49-7.39 (m, 2H), 7.10 (m, 2H), 6.96 (s, 1H), 2.67 (s, 3H), 2.65 (s, 3H). | ¹³C NMR: (125 MHz, d6-DMSO) 161.5, 157.9, 147.1, 145.2, 141.1, 140.3, 133.3, 121.6, 120.9, 117.1, 116.1, 111.9, 110.1, 109.5, 102.6, 24.8, 18.1, | ESI-MS m/z: 306 (M + H)⁺ |
| 27 | 271 | 15.85 | ¹H NMR (500 MHz, CDCl₃) δ 8.65 (d, J = 7.0 Hz, 1H), 7.52 (d, J = 3.2 Hz, 1H), 7.01 (d, J = 3.2 Hz, 1H), 6.45 (s, 1H), 4.14-4.01 (m, 1H), 2.55 (s, 6H), 2.10-1.97 (m, 2H), 1.81-1.70 (m, 2H), 1.66-1.53 (m, 1H), 1.53-1.26 (m, 5H). | ¹³C NMR: (125 MHz, CDCl₃) 163.6, 154.9, 142.1, 139.3, 117.2, 107.9, 106.3, 106.0, 47.1, 33.3, 26.0, 24.8, 24.6, 18.2, | ESI-MS m/z: 294 (M + Na)⁺, 272 (M + H)⁺ |
| 28 | 305 | 3.98 | ¹H NMR (500 MHz, CDCl₃) δ 8.94 (d, J = 7.8 Hz, 1H), 7.55 (d, J = 3.3 Hz, 1H), 7.45 (d, J = 6.9 Hz, 1H), 7.30-7.19 (m, 3H), 7.04 (d, J = 3.3 Hz, 1H), 6.44 (s, 1H), 5.74 (q, J = 8.0 Hz, 1H), 3.04 (ddd, J = 15.7, 8.7, 2.5 Hz, 1H), 2.98-2.89 (m, 1H), 2.80-2.70 (m, 1H), 2.56 (s, 3H), 2.44 (s, 3H), 2.04-1.92 (m, 1H). | ¹³C NMR: (125 MHz, CDCl₃) 164.6, 155.2, 144.8, 143.3, 142.1, 139.6, 127.4, 126.6, 124.7, 124.2, 117.2, 108.1, 106.5, 105.5, 54.5, 34.9, 30.5, 24.7, 18.2, | ESI-MS m/z: 328 (M + Na)⁺, 306 (M + H)⁺ |
| 29 | 305 | 2.51 | ¹H NMR (500 MHz, CDCl₃) δ 8.94 (d, J = 7.2 Hz, 1H), 7.52 (d, J = 3.3 Hz, 1H), 7.27 (m, 2H), 7.20-7.16 (m, 2H), 7.01 (d, J = 3.3 Hz, 1H), 6.42 (s, 1H), 5.08-4.93 (m, 1H), 3.45 (dd, J = 15.8, 7.3 Hz, 2H), 3.00 (dd, J = 15.8, 6.0 Hz, 2H), 2.54 (s, 3H), 2.42 (s, 3H). | ¹³C NMR: (125 MHz, CDCl₃) 164.3, 155.1, 142.1, 141.7, 139.4, 126.6, 124.8, 117.1, 108.0, 106.4, 105.7, 50.4, 40.6, 24.6, 18.2, | ESI-MS m/z: 328 (M + Na)⁺, 306 (M + H)⁺ |
| 30 | 309 | 2.82 | ¹H NMR (500 MHz, CDCl₃) δ 10.73 (s, 1H), 7.72 (d, J = 8.3 Hz, 2H), 7.55 (d, J = 3.2 Hz, 1H), 7.21 (d, J = 8.3 Hz, 2H), 7.05 (d, J = 3.2 Hz, 1H), 6.51 (s, 1H), 3.85 (t, J = 6.6 Hz, 2H), 2.86 (t, J = 6.6 Hz, 2H), 2.61 (s, 3H), 2.57 (s, 3H). | ¹³C NMR: (125 MHz, CDCl₃) 162.4, 155.5, 142.6, 139.4, 138.1, 132.9, 129.5, 119.8, 117.2, 108.4, 107.0, 105.8, 63.9, 38.8, 24.8, 18.3, | ESI-MS m/z: 332 (M + Na)⁺, 310 (M + H)⁺ |

TABLE 1-continued

| | | | | | |
|---|---|---|---|---|---|
| 31 | 322 | 0.40 | $^1$H NMR (500 MHz, d6-DMSO) δ 12.14 (s, 1H), 8.00 (d, J = 7.5 Hz, 1H), 7.79 (d, J = 7.6 Hz, 1H), 7.58 (s, 1H), 7.49-7.40 (m, 2H), 7.31 (t, J = 6.9 Hz, 1H), 7.01 (s, 1H), 2.68 (s, 3H), 2.67 (s, 3H). | $^{13}$C NMR: (125 MHz, d6-DMSO) 161.1, 158.3, 158.0, 149.1, 145.4, 140.7, 132.1, 126.5, 123.7, 122.1, 120.7, 116.1, 110.6, 109.8, 101.8, 24.8, 18.1, | ESI-MS m/z: 345 (M + Na)$^+$, 323 (M + H)$^+$ |
| 32 | 362 | 50 | $^1$H NMR (500 MHz, CDCl$_3$) δ 8.67 (d, J = 6.1 Hz, 1H), 7.50 (d, J = 3.2 Hz, 1H), 7.37-7.30 (m, 4H), 7.29-7.24 (m, 1H), 7.01 (d, J = 3.2 Hz, 1H), 6.46 (s, 1H), 4.20-4.09 (m, 1H), 3.56 (s, 2H), 2.90-2.82 (m, 2H), 2.55 (s, 3H), 2.54 (s, 3H), 2.25-2.35 (m, 2H), 2.11-2.03 (m, 2H), 1.75-1.66 (m, 2H). | $^{13}$C NMR: (125 MHz, CDCl$_3$) 163.8, 155.1, 142.1, 139.4, 129.4, 128.3, 127.2, 117.2, 108.0, 106.4, 105.8, 63.4, 52.3, 45.3, 32.4, 24.7, 18.2, | ESI-MS m/z: 363 (M + H)$^+$ |
| 33 | 286 | NA | $^1$H NMR (500 MHz, d6-DMSO) δ 7.36 (d, J = 3.2 Hz, 1H), 7.22 (d, J = 3.2 Hz, 1H), 6.79 (s, 1H), 3.99 (m, 1H), 3.43 (m, 2H), 3.10 (m, 2H), 2.76 (s, 3H), 2.58 (s, 3H), 2.50 (s, 3H), 2.24-2.06 (m, 2H), 1.76-1.59 (m, 2H). | $^{13}$C NMR: (125 MHz, d6-DMSO) 162.8, 155.8, 143.7, 138.7, 115.6, 108.1, 104.1, 52.8, 43.1, 42.5, 29.6, 24.3, 17.6, | ESI-MS m/z: 287 (M + H)$^+$ |
| 34 | 314 | 30 | $^1$H NMR (500 MHz, CD$_3$OD) δ 7.40 (d, J = 3.3 Hz, 1H), 7.34 (d, J = 3.3 Hz, 1H), 6.79 (s, 1H), 4.22 (brs, 1H), 3.59 (m, 2H), 3.28 (m, 1H), 2.67 (s, 3H), 2.60 (s, 3H), 2.43 (brs, 2H), 1.90 (brs, 2H), 1.42 (d, J = 6.7 Hz, 6H). | $^{13}$C NMR: (125 MHz, CD$_3$OD) 166.6, 158.1, 145.3, 141.4, 116.9, 109.5, 109.0, 104.5, 59.5, 45.5, 31.1, 24.6, 17.9, 17.0, | ESI-MS m/z: 315 (M + H)$^+$ |
| 35 | 348 | 22.39 | $^1$H NMR (500 MHz, CDCl$_3$) δ 8.75 (d, J = 7.8 Hz, 1H), 7.51 (d, J = 3.2 Hz, 1H), 7.30-7.25 (m, 2H), 7.02 (d, J = 3.2 Hz, 1H), 6.99 (d, J = 8.0 Hz, 2H), 6.85 (t, J = 7.3 Hz, 1H), 6.46 (s, 1H), 4.36-4.19 (m, 1H), 3.67-3.52 (m, 2H), 3.13-3.00 (m, 2H), 2.55 (s, 3H), 2.52 (s, 3H), 2.29-2.14 (m, 2H), 1.87-1.74 (m, 2H). | $^{13}$C NMR: (125 MHz, CDCl$_3$) 163.8, 155.2, 151.7, 142.2, 139.4, 129.2, 119.6, 117.1, 116.7, 108.0, 106.4, 105.7, 48.5, 45.3, 32.2, 24.8, 18.2, | ESI-MS m/z: 371 (M + Na)$^+$, 349 (M + H)$^+$ |
| 36 | 331 | 10? | $^1$H NMR (500 MHz, CDCl$_3$) δ 10.90 (s, 1H), 7.89 (d, J = 8.7 Hz, 2H), 7.82 (s, 1H), 7.56 (d, J = 3.2 Hz, 1H), 7.36 (d, J = 8.7 Hz, 2H), 7.19 (s, 1H), 7.08 (d, J = 3.2 Hz, 1H), 6.54 (s, 1H), 2.64 (s, 3H), 2.59 (s, 3H). | $^{13}$C NMR: (125 MHz, CDCl$_3$) 162.5, 155.8, 142.8, 139.6, 139.2, 135.7, 132.2, 130.2, 122.3, 120.4, 118.6, 117.2, 108.5, 107.2, 105.5, 24.8, 18.3, | ESI-MS m/z: 332 (M + H)$^+$ |
| 37 | 314 | 40 | $^1$H NMR (500 MHz, CD$_3$OD) δ 7.39 (d, J = 3.3 Hz, 1H), 7.33 (d, J = 3.3 Hz, 1H), 6.78 (s, 1H), 4.31 (t, J = 2.7 Hz, 1H), 3.42-3.35 (m, 1H), 2.92 (s, 6H), 2.67 (s, 3H), 2.63 (s, 3H), 2.19 (d, J = 10.4 Hz, 2H), 2.10 (d, J = 9.1 Hz, 2H), 1.92-1.79 (m, 4H). | $^{13}$C NMR: (125 MHz, CD$_3$OD) 166.4, 158.1, 145.3, 141.3, 116.8, 109.4, 108.9, 105.0, 65.8, 44.3, 40.3, 29.6, 24.9, 23.0, 17.9, | ESI-MS m/z: 315 (M + H)$^+$ |

TABLE 1-continued

| | | | ¹H NMR | ¹³C NMR | ESI-MS |
|---|---|---|---|---|---|
| 38 | 365 | 0.79 (TC) | ¹H NMR (500 MHz, CDCl₃) δ 10.87 (s, 1H), 7.77 (d, J = 8.6 Hz, 2H), 7.58-7.49 (m, 5H), 7.39-7.28 (m, 3H), 7.06 (d, J = 3.3 Hz, 1H), 6.52 (s, 1H), 2.63 (s, 3H), 2.57 (s, 3H). | ¹³C NMR: (125 MHz, CDCl₃) 162.5, 155.8, 142.8, 140.0, 139.6, 132.6, 131.7, 128.5, 128.1, 123.8, 119.1, 117.3, 108.6, 107.2, 105.7, 90.0, 88.6, 24.9, 18.4, | ESI-MS m/z: 388 (M + Na)⁺, 366 (M + H)⁺ |
| 39 | 341 | 39.81 | ¹H NMR (400 MHz, d6-DMSO) δ 11.80 (s, 1H), 7.51 (d, J = 3.4 Hz, 1H), 7.37 (d, J = 3.4 Hz, 1H), 6.92 (s, 1H), 3.80 (s, 2H), 2.98 (t, J = 5.5 Hz, 2H), 2.77 (t, J = 5.5 Hz, 2H), 2.64 (s, 3H), 2.60 (s, 3H), 2.56 (s, 3H). | ¹³C NMR: (100 MHz, d6-DMSO) 160.0, 157.4, 144.7, 142.0, 139.8, 117.2, 115.5, 109.7, 109.0, 101.5, 51.6, 51.0, 43.9, 25.4, 24.3, 17.6 | ESI-MS m/z: 342 (M + H)⁺ |
| 40 | 320 | | ¹H NMR (400 MHz, d6-DMSO) δ 10.86 (s, 1H), 7.91 (s, 1H), 7.62 (dd, J = 8.2, 1.7 Hz, 1H), 7.46 (d, J = 3.3 Hz, 1H), 7.38-7.34 (m, 2H), 6.89 (s, 1H), 4.52 (s, 2H), 4.46 (s, 2H), 2.96 (s, 3H), 2.64 (s, 3H), 2.63 (s, 3H). | ¹³C NMR: (100 MHz, d6-DMSO) 161.4, 156.5, 144.2, 139.4, 138.9, 136.4, 129.4, 123.2, 118.5, 115.7, 112.8, 108.7, 108.5, 103.9, 59.8, 59.4, 40.7, 24.2, 17.6, | ESI-MS m/z: 321 (M + H)⁺ |
| 41 | 356 | 39.91 | ¹H NMR (500 MHz, CDCl₃) δ 12.14 (s, 1H), 7.80 (d, J = 1.9 Hz, 1H), 7.73 (d, J = 8.4 Hz, 1H), 7.60 (d, J = 3.4 Hz, 1H), 7.24 (d, J = 2.0 Hz, 1H), 7.14 (d, J = 3.4 Hz, 1H), 6.63 (d, J = 1.2 Hz, 1H), 2.73 (s, 3H), 2.64 (s, 3H). | ¹³C NMR: (125 MHz, CDCl₃) 161.8, 160.3, 157.6, 150.3, 143.1, 140.9, 131.8, 131.0, 123.6, 122.0, 120.5, 117.2, 109.4, 108.2, 103.1, 24.9, 18.3, | ESI-MS m/z: 379 (M + Na)⁺, 357 (M + H)⁺ |
| 42 | 340 | 50.18 | ¹H NMR (500 MHz, CDCl₃) δ 12.12 (s, 1H), 7.77-7.70 (m, 1H), 7.58 (s, 1H), 7.50 (d, J = 9.8 Hz, 1H), 7.12 (s, 1H), 7.03 (t, J = 8.8 Hz, 1H), 6.61 (s, 1H), 2.72 (s, 3H), 2.62 (s, 3H). | ¹³C NMR: (125 MHz, CDCl₃) 163.0, 161.7, 161.1, 160.9, 157.5, 150.4, 143.1, 140.9, 128.0, 121.9, 121.9, 117.2, 111.6, 111.4, 109.4, 108.2, 107.2, 107.0, 103.2, 24.9, 18.3, | ESI-MS m/z: 363 (M + Na)⁺, 341 (M + H)⁺ |
| 43 | 336 | 0.20 | ¹H NMR (500 MHz, CDCl₃) δ 12.06 (s, 1H), 7.67 (d, J = 7.7 Hz, 1H), 7.58 (d, J = 3.3 Hz, 1H), 7.23 (d, J = 7.2 Hz, 1H), 7.18 (t, J = 7.5 Hz, 1H), 7.11 (d, J = 3.3 Hz, 1H), 6.58 (s, 1H), 2.73 (s, 3H), 2.72 (s, 3H), 2.60 (s, 3H). | ¹³C NMR: (125 MHz, CDCl₃) 161.8, 157.8, 157.2, 143.0, 140.7, 132.4, 130.5, 126.6, 123.2, 118.7, 117.2, 109.2, 108.0, 103.4, 24.9, 18.3, 18.1, | ESI-MS m/z: 359 (M + Na)⁺, 337 (M + H)⁺ |
| 44 | 301 | 22.39 | ¹H NMR (500 MHz, CDCl₃) δ 12.09 (s, 1H), 7.56 (d, J = 3.4 Hz, 1H), 7.12 (d, J = 3.4 Hz, 1H), 6.61 (s, 1H), 3.08 (q, J = 7.6 Hz, 2H), 2.68 (s, 3H), 2.62 (s, 3H), 1.43 (t, J = 7.6 Hz, 3H). | ¹³C NMR: (125 MHz, CDCl₃) 166.5, 161.0, 158.9, 157.5, 143.1, 141.0, 117.2, 109.3, 108.1, 102.9, 24.7, 23.7, 18.3, 14.3, | ESI-MS m/z: 324 (M + Na)⁺, 302 (M + H)⁺ |

TABLE 1-continued

| | | | 1H NMR | 13C NMR | ESI-MS |
|---|---|---|---|---|---|
| 45 | 317 | 35.48 | 1H NMR (500 MHz, CDCl3) δ 11.64 (s, 1H), 9.33 (s, 1H), 8.01 (d, J = 8.4 Hz, 1H), 7.86-7.80 (m, 2H), 7.68 (d, J = 3.3 Hz, 1H), 7.48 (t, J = 7.1 Hz, 1H), 7.11 (d, J = 3.3 Hz, 1H), 6.57 (s, 1H), 2.72 (s, 3H), 2.62 (s, 3H). | 13C NMR: (125 MHz, CDCl3) 162.1, 161.5, 156.3, 155.5, 151.5, 142.7, 140.1, 134.3, 127.7, 127.3, 125.5, 122.2, 117.8, 108.7, 107.4, 105.7, 24.9, 18.3, | ESI-MS m/z: 340 (M + Na)+, 318 (M + H)+ |
| 46 | 334 | 0.45 | 1H NMR (500 MHz, CDCl3) δ 11.14 (s, 1H), 8.95 (s, 1H), 7.60 (s, 1H), 7.09 (s, 1H), 6.54 (s, 1H), 6.52 (s, 1H), 2.73 (s, 6H), 2.60 (s, 6H). | 13C NMR: (125 MHz, CDCl3) 161.7, 156.2, 155.6, 144.6, 142.4, 139.8, 138.4, 136.4, 117.1, 111.7, 108.3, 108.2, 106.9, 105.8, 24.8, 24.6, 18.3, 16.7, | ESI-MS m/z: 357 (M + Na)+, 335 (M + H)+ |
| 47 | 352 | Inhibitor | 1H NMR (500 MHz, CDCl3) δ 11.96 (s, 1H), 7.71 (d, J = 8.8 Hz, 1H), 7.55 (d, J = 3.2 Hz, 1H), 7.32 (d, J = 2.3 Hz, 1H), 7.09 (d, J = 3.2 Hz, 1H), 7.02 (dd, J = 8.8, 2.4 Hz, 1H), 6.56 (s, 1H), 3.88 (s, 3H), 2.69 (s, 3H), 2.58 (s, 3H). | 13C NMR: (125 MHz, CDCl3) 161.7, 157.3, 156.9, 156.4, 143.4, 143.0, 140.7, 133.8, 121.2, 117.1, 114.8, 109.2, 108.0, 104.4, 103.3, 55.9, 24.8, 18.2, | ESI-MS m/z: 375 (M + Na)+, 353 (M + H)+ |
| 48 | 336 | 0.20 | 1H NMR (500 MHz, CDCl3) δ 12.02 (s, 1H), 7.71 (d, J = 8.2 Hz, 1H), 7.64 (s, 1H), 7.60 (d, J = 3.3 Hz, 1H), 7.23 (dd, J = 8.2, 1.1 Hz, 1H), 7.13 (d, J = 3.4 Hz, 1H), 6.61 (s, 1H), 2.72 (s, 3H), 2.62 (s, 3H), 2.48 (s, 3H). | 13C NMR: (125 MHz, CDCl3) 161.7, 158.2, 157.3, 147.1, 143.0, 140.8, 133.2, 132.7, 127.4, 121.2, 120.2, 117.2, 109.3, 108.0, 103.4, 24.9, 21.5, 18.3, | ESI-MS m/z: 359 (M + Na)+, 337 (M + H)+ |
| 49 | 298 | 39.81 | 1H NMR (500 MHz, CDCl3) δ 11.05 (s, 1H), 7.91 (s, 1H), 7.61 (d, J = 3.3 Hz, 1H), 7.07 (d, J = 3.3 Hz, 1H), 6.52 (s, 1H), 4.12 (t, J = 7.1 Hz, 2H), 2.62 (s, 3H), 2.58 (s, 3H), 1.97 (m, 2H), 0.96 (t, J = 7.4 Hz, 3H). | 13C NMR: (125 MHz, CDCl3) 161.0, 157.4, 156.0, 142.5, 141.7, 139.9, 117.7, 108.6, 107.1, 105.2, 51.7, 24.7, 23.1, 18.3, 11.1, | ESI-MS m/z: 299 (M + H)+ |
| 50 | 391 | 10 | 1H NMR (500 MHz, CDCl3) δ 10.57 (s, 1H), 7.66 (d, J = 8.9 Hz, 2H), 7.57 (d, J = 3.2 Hz, 1H), 7.05 (d, J = 3.2 Hz, 1H), 6.96 (d, J = 8.9 Hz, 2H), 6.50 (s, 1H), 3.73-3.61 (m, 2H), 2.74-2.64 (m, 2H), 2.60 (s, 3H), 2.57 (s, 3H), 2.33 (s, 6H), 2.30-2.22 (m, 1H), 1.93 (d, J = 12.4 Hz, 2H), 1.68 (m, 2H). | 13C NMR: (125 MHz, CDCl3) 162.2, 155.3, 147.7, 142.4, 139.3, 132.4, 120.7, 117.6, 117.3, 108.2, 106.8, 106.1, 62.2, 50.2, 41.8, 28.4, 24.7, 18.3, | ESI-MS m/z: 392 (M + H)+ |
| 51 | 285 | 15.85 | 1H NMR (500 MHz, CDCl3) δ 9.00 (s, 1H), 7.53 (d, J = 3.3 Hz, 1H), 7.20 (dd, J = 5.1, 1.2 Hz, 1H), 7.10-7.04 (m, 1H), 7.00 (d, J = 3.3 Hz, 1H), 6.95 (dd, J = 5.1, 3.5 Hz, 1H), 6.43 (s, 1H), 4.90 (d, J = 5.7 Hz, 2H), 2.53 (s, 3H), 2.50 (s, 3H). | 13C NMR: (125 MHz, CDCl3) 164.3, 155.4, 143.0, 142.2, 139.6, 126.8, 125.2, 124.5, 117.2, 108.1, 106.5, 105.3, 38.0, 24.6, 18.2, | ESI-MS m/z: 308 (M + Na)+, 286 (M + H)+ |
| 52 | 306 | 0.20 | 1H NMR (500 MHz, CDCl3) δ 10.77 (s, 1H), 7.78 (d, J = 8.8 Hz, 2H), 7.56 (d, J = 3.3 Hz, 1H), 7.06 (d, J = 3.3 Hz, 1H), 7.01 (d, J = 8.8 Hz, 2H), 6.52 (s, 1H), 2.62 (s, 3H), 2.58 (s, 3H). | 13C NMR: (125 MHz, CDCl3) 162.4, 155.6, 142.7, 139.5, 136.9, 134.2, 120.8, 119.5, 117.3, 108.4, 107.1, 105.7, 24.8, 18.3, | ESI-MS m/z: 329 (M + Na)+, 307 (M + H)+ |

TABLE 1-continued

| | | | | | |
|---|---|---|---|---|---|
| 53 | 369 | 0.14 | ¹H NMR (500 MHz, CDCl₃) δ 11.07 (s, 1H), 7.89 (d, J = 9.0 Hz, 2H), 7.87 (d, J = 9.0 Hz, 2H), 7.80 (d, J = 7.1 Hz, 2H), 7.60-7.53 (m, 2H), 7.49 (t, J = 7.6 Hz, 2H), 7.09 (d, J = 3.3 Hz, 1H), 6.56 (s, 1H), 2.65 (s, 3H), 2.60 (s, 3H). | ¹³C NMR: (125 MHz, CDCl₃) 218.4, 195.8, 162.6, 156.0, 143.9, 142.9, 139.8, 138.4, 132.0, 131.9, 131.7, 129.9, 128.3, 118.5, 117.3, 108.6, 107.4, 105.6, 24.8, 18.3, | ESI-MS m/z: 392 (M + Na)⁺, 370 (M + H)⁺ |
| 54 | 357 | 0.56 | ¹H NMR (500 MHz, CDCl₃) δ 10.73 (s, 1H), 7.76 (d, J = 8.9 Hz, 2H), 7.58 (d, J = 3.2 Hz, 1H), 7.35-7.28 (m, 2H), 7.09-7.03 (m, 4H), 7.01 (d, J = 7.9 Hz, 2H), 6.52 (s, 1H), 2.62 (s, 3H), 2.59 (s, 3H). | ¹³C NMR: (125 MHz, CDCl₃) 162.4, 158.3, 155.5, 152.2, 142.6, 139.4, 135.6, 129.7, 122.7, 121.0, 120.1, 118.1, 117.3, 108.4, 107.0, 105.9, 24.8, 18.3, | ESI-MS m/z: 380 (M + Na)⁺, 358 (M + H)⁺ |
| 55 | 355 | NA | ¹H NMR (500 MHz, CDCl₃) δ 10.82 (s, 1H), 7.85 (d, J = 8.5 Hz, 2H), 7.60 (s, 2H), 7.58 (s, 1H), 7.51 (d, J = 8.0 Hz, 2H), 7.24 (d, J = 7.9 Hz, 2H), 7.08 (d, J = 3.2 Hz, 1H), 6.53 (s, 1H), 2.64 (s, 3H), 2.59 (s, 3H), 2.40 (s, 3H). | ¹³C NMR: (125 MHz, CDCl₃) 162.4, 155.5, 142.6, 139.5, 138.8, 138.2, 136.6, 135.7, 129.5, 127.4, 126.7, 119.8, 117.4, 108.4, 107.0, 106.0, 24.8, 21.2, 18.3, | ESI-MS m/z: 378 (M + Na)⁺. |
| 56 | 353 | 15.85 | ¹H NMR (500 MHz, d6-DMSO) δ 12.40 (s, 1H), 10.60 (s, 1H), 7.65 (d, J = 9.0 Hz, 2H), 7.43 (d, J = 3.2 Hz, 1H), 7.34 (d, J = 3.2 Hz, 1H), 6.94 (d, J = 9.0 Hz, 2H), 6.84 (s, 1H), 4.17 (t, J = 6.0 Hz, 2H), 2.70 (t, J = 6.0 Hz, 2H), 2.63 (s, 3H), 2.61 (s, 3H). | ¹³C NMR: (125 MHz, d6-DMSO) 172.3, 161.0, 156.1, 153.9, 143.9, 138.6, 132.7, 120.1, 115.7, 114.7, 108.4, 108.3, 104.2, 63.8, 34.2, 24.2, 17.5, | ESI-MS m/z: 352 (M − H)⁻ |
| 57 | 432 | 7.08 Activator | ¹H-NMR (500 MHz, d6-DMSO) δ 12.10 (brs, 1H), 10.86 (s, 1H), 8.53 (s, 1H), 7.84 (s, 4H), 7.49 (d, J = 3.2 Hz, 1H), 7.38 (d, J = 3.3 Hz, 1H), 6.91 (s, 1H), 4.42 (t, J = 6.9 Hz, 2H), 2.66 (s, 6H), 2.29 (s, 2H), 1.96-1.83 (m, 2H), 1.58-1.45 (m, 2H). | ¹³C NMR: (125 MHz, d6-DMSO) 161.3, 156.4, 146.2, 144.1, 138.9, 138.9, 125.8, 125.3, 120.6, 118.9, 115.8, 108.7, 108.5, 104.1, 49.2, 32.9, 29.1, 24.3, 21.4, 17.6, | ESI-MS m/z: 455 (M + Na)⁺, 433 (M + H)⁺ |
| 58 | 460 | 1.78 Activator | ¹H NMR (500 MHz, d6-DMSO) δ 12.00 (s, 1H), 10.84 (s, 1H), 8.52 (s, 1H), 7.83 (s, 4H), 7.46 (d, J = 3.3 Hz, 1H), 7.37 (d, J = 3.3 Hz, 1H), 6.87 (s, 1H), 4.39 (t, J = 7.1 Hz, 2H), 2.65 (s, 3H), 2.64 (s 3H), 2.22 (s, 2H), 1.91-1.84 (m, 2H), 1.55-1.46 (m, 2H), 1.37-1.25 (m, 4H). | ¹³C NMR: (125 MHz, d6-DMSO) 161.3, 156.4, 146.2, 144.1, 138.9, 138.8, 125.8, 125.3, 120.5, 118.9, 115.7, 108.6, 108.4, 104.1, 49.4, 29.5, 27.9, 25.6, 24.2, 17.5, | ESI-MS m/z: 483 (M + Na)⁺, 461 (M + H)⁺ |
| 59 | 488 | 1.78 Activator | ¹H NMR (500 MHz, d6-DMSO) δ 11.97 (s, 1H), 10.85 (s, 1H), 8.52 (s, 1H), 7.83 (s, 4H), 7.47 (d, J = 3.3 Hz, 1H), 7.38 (d, J = 3.3 Hz, 1H), 6.89 (s, 1H), 4.39 (t, J = 7.1 Hz, 2H), 2.66 (s, 6H), 2.20 (brs, 2H), 1.87 (t, J = 6.7 Hz, 2H), 1.49 (m, 2H), 1.36-1.19 (m, 8H). | ¹³C NMR: (125 MHz, d6-DMSO) 161.3, 156.4, 146.2, 144.1, 138.9, 138.8, 125.8, 125.4, 120.5, 118.9, 115.8, 108.7, 108.5, 104.1, 49.4, 29.6, 28.5, 28.4, 28.2, 25.8, 24.4, 24.3, 17.6, | ESI-MS m/z: 487 (M − H)⁻ |

TABLE 1-continued

| | | | | | |
|---|---|---|---|---|---|
| 60 | 529 | 0.63 Activator | ¹H NMR (500 MHz, CDCl₃) δ 10.83 (s, 1H), 7.84 (d, J = 8.7 Hz, 2H), 7.80 (d, J = 8.8 Hz, 2H), 7.79 (s, 1H), 7.56 (d, J = 3.3 Hz, 1H), 7.06 (d, J = 3.3 Hz, 1H), 6.52 (s, 1H), 4.44 (t, J = 6.9 Hz, 2H), 2.82 (s, 4H), 2.67 (t, J = 7.0 Hz, 2H), 2.63 (s, 3H), 2.57 (s, 3H), 2.14-2.06 (m, 2H), 1.86-1.78 (m, 2H). | ¹³C NMR: (125 MHz, CDCl₃) 169.1, 168.1, 162.5, 155.7, 148.1, 142.6, 139.7, 139.5, 126.4, 125.2, 119.7, 119.1, 117.3, 108.5, 107.1, 105.9, 49.7, 30.5, 29.1, 25.7, 24.8, 21.7, 18.3, | ESI-MS m/z: 552 (M + Na)⁺, 530 (M + H)⁺ |
| 61 | 557 | 0.40 | ¹H NMR (500 MHz, CDCl₃) δ 10.84 (s, 1H), 7.85 (d, J = 8.6 Hz, 2H), 7.82 (d, J = 8.6 Hz, 2H), 7.75 (s, 1H), 7.57 (d, J = 3.2 Hz, 1H), 7.07 (d, J = 3.2 Hz, 1H), 6.53 (s, 1H), 4.40 (t, J = 7.0 Hz, 2H), 2.82 (s, 4H), 2.64 (s, 3H), 2.61 (t, J = 7.2 Hz, 2H), 2.58 (s, 3H), 2.02-1.92 (m, 2H), 1.81-1.70 (m, 2H), 1.54-1.45 (m, 2H), 1.45-1.36 (m, 2H). | ¹³C NMR: (125 MHz, CDCl₃) 169.2, 168.6, 162.5, 155.7, 147.8, 142.6, 139.7, 139.5, 126.4, 125.4, 119.6, 119.2, 117.3, 108.5, 107.1, 105.9, 50.2, 30.9, 30.1, 28.0, 25.9, 25.7, 24.8, 24.4, 18.3, | ESI-MS m/z: 580 (M + Na)⁺, 558 (M + H)⁺ |
| 62 | 585 | 0.45 Activator | ¹H NMR (500 MHz, CDCl₃) δ 10.84 (s, 1H), 7.85 (d, J = 8.7 Hz, 2H), 7.82 (d, J = 8.7 Hz, 2H), 7.73 (s, 1H), 7.57 (d, J = 3.2 Hz, 1H), 7.07 (d, J = 3.2 Hz, 1H), 6.53 (s, 1H), 4.39 (t, J = 7.2 Hz, 2H), 2.82 (s, 4H), 2.64 (s, 3H), 2.59 (t, J = 7.3 Hz, 2H), 2.58 (s, 3H), 2.01-1.89 (m, 2H), 1.81-1.68 (m, 2H), 1.50-1.21 (m, 8H). | ¹³C NMR: (125 MHz, CDCl₃) 169.3, 168.7, 162.5, 155.7, 147.8, 142.6, 139.7, 139.5, 126.4, 125.4, 119.6, 119.0, 117.3, 108.4, 107.1, 105.8, 50.5, 31.0, 30.4, 28.8, 28.8, 28.6, 26.4, 25.7, 24.8, 24.6, 18.3, | ESI-MS m/z: 608 (M + Na)⁺, 586 (M + H)⁺ |
| 63 | 403 | 39.81 | ¹H NMR (500 MHz, CDCl₃) δ 10.83 (s, 1H), 7.88 (s, 1H), 7.84 (d, J = 8.9 Hz, 2H), 7.81 (d, J = 8.8 Hz, 2H), 7.56 (d, J = 3.3 Hz, 1H), 7.06 (d, J = 3.3 Hz, 1H), 6.52 (s, 1H), 4.49 (t, J = 6.3 Hz, 2H), 2.82 (t, J = 6.3 Hz, 2H), 2.64 (s, 3H), 2.57 (s, 3H), 2.32 (s, 6H) | ¹³C NMR: (125 MHz, CDCl₃) 162.5, 155.7, 147.8, 142.6, 139.6, 139.5, 126.4, 125.5, 119.8, 119.6, 117.2, 108.4, 107.1, 105.8, 58.9, 48.3, 45.5, 24.8, 18.3, | ESI-MS m/z: 404 (M + H)⁺ |
| 64 | 389 | 7.07 | ¹H NMR (500 MHz, d6-DMSO) δ 10.86 (s, 1H), 8.60 (s, 1H), 8.14 (brs, 2H), 7.84 (s, 4H), 7.48 (d, J = 3.2 Hz, 1H), 7.37 (d, J = 3.2 Hz, 1H), 6.90 (s, 1H), 4.55 (t, J = 6.7 Hz, 2H), 2.85 (s, 2H), 2.65 (s, 6H), 2.31-2.11 (m, 2H). | ¹³C NMR: (125 MHz, d6-DMSO) 161.4, 156.5, 146.3, 144.1, 139.1, 138.9, 125.8, 125.2, 120.9, 118.9, 115.8, 108.7, 108.5, 104.0, 46.7, 36.2, 27.7, 24.3, 17.6, | ESI-MS m/z: 390 (M + H)⁺ |
| 65 | 419 | 7.08 | ¹H NMR (500 MHz, CDCl₃) δ 10.84 (s, 1H), 7.90 (s, 1H), 7.85 (d, J = 8.7 Hz, 2H), 7.82 (d, J = 8.6 Hz, 1H), 7.57 (t, J = 3.4 Hz, 1H), 7.07 (d, J = 3.1 Hz, 1H), 6.53 (s, 1H), 4.59 (t, J = 5.1 Hz, 2H), 3.89 (t, J = 5.1 Hz, 2H), 3.55-3.48 (t, J = 4.8 Hz, 2H), 2.95-2.83 (m, 2H), 2.64 (s, 3H), 2.58 (s, 3H). | ¹³C NMR: (125 MHz, CDCl₃) 162.5, 155.6, 147.9, 142.6, 139.7, 139.5, 126.4, 125.4, 120.2, 119.7, 117.3, 108.4, 107.1, 105.8, 73.3, 69.4, 50.4, 41.6, 24.8, 18.3 | ESI-MS m/z: 420 (M + H)⁺ |

TABLE 1-continued

| 66 | 507 | 7.94 | ¹H NMR (500 MHz, CDCl₃) δ 10.83 (s, 1H), 7.95 (s, 1H), 7.84 (d, J = 8.8 Hz, 2H), 7.81 (d, J = 8.7 Hz, 2H), 7.57 (d, J = 3.3 Hz, 1H), 7.07 (d, J = 3.2 Hz, 1H), 6.52 (s, 1H), 4.58 (t, J = 5.0 Hz, 2H), 3.90 (t, J = 5.0 Hz, 2H), 3.62 (s, 4H), 3.61-3.54 (m, 4H), 3.45 (t, J = 5.2 Hz, 2H), 2.82 (s, 2H), 2.64 (s, 3H), 2.58 (s, 3H). | ¹³C NMR: (125 MHz, CDCl₃) 155.6, 147.8, 142.6, 139.6, 139.5, 126.4, 125.5, 120.5, 119.7, 117.4, 108.4, 107.1, 105.9, 73.3, 70.8, 70.7, 70.6, 70.4, 69.7, 50.4, 41.8, 24.8, 18.3, | ESI-MS m/z: 508 (M + H)⁺ |
|---|---|---|---|---|---|
| 67 | 604 | 8.91 | ¹H NMR (500 MHz, CDCl₃) δ 10.80 (s, 1H), 7.95 (s, 1H), 7.80 (s, 4H), 7.51 (d, J = 3.2 Hz, 1H), 7.03 (d, J = 3.2 Hz, 1H), 6.54 (brs, 1H), 6.49 (s, 1H), 4.56 (t, J = 4.9 Hz, 2H), 3.89 (t, J = 4.9 Hz, 2H), 3.75-3.64 (m, 6H), 3.60 (m, 4H), 3.33 (q, J = 5.7 Hz, 2H), 2.61 (s, 3H), 2.53 (s, 3H), 2.47 (d, J = 4.7 Hz, 6H), 2.41 (t, J = 6.0 Hz, 2H). | ¹³C NMR: (125 MHz, CDCl₃) 171.1, 162.4, 155.7, 147.7, 142.7, 139.6, 139.5, 126.3, 125.4, 120.5, 119.6, 117.0, 108.4, 107.1, 105.5, 70.5, 70.3, 69.5, 67.3, 66.6, 57.2, 53.3, 50.3, 36.9, 35.6, 24.8, 18.2, | ESI-MS m/z: 605 (M + H)⁺ |
| 68 | 602 | 10 | ¹H NMR (500 MHz, CDCl₃) δ 10.82 (s, 1H), 7.93 (s, 1H), 7.82 (d, J = 8.6 Hz, 2H), 7.79 (d, J = 8.6 Hz, 2H), 7.53 (d, J = 3.0 Hz, 1H), 7.04 (d, J = 3.0 Hz, 1H), 6.72 (s, 1H), 6.50 (s, 1H), 4.61-4.46 (m, 2H), 3.96-3.79 (m, 2H), 3.67 (t, J = 6.0 Hz, 2H), 3.58 (d, J = 5.5 Hz, 4H), 3.38-3.25 (m, 1H), 3.24-3.11 (m, 1H), 3.09-2.95 (m, 1H), 2.62 (s, 3H), 2.55 (s, 3H), 2.36 (t, J = 6.0 Hz, 2H), 2.26 (s, 3H), 2.21-2.06 (m, 2H), 1.96-1.83 (m, 1H), 1.81-1.59 (m, 3H), 1.55-1.45 (m J = 13.3, 7.3 Hz, 2H). | ¹³C NMR: (125 MHz, CDCl₃) 170.9, 162.5, 155.7, 147.8, 142.7, 139.6, 139.5, 126.4, 125.4, 120.5, 119.7, 117.2, 108.5, 107.1, 105.7, 70.5, 70.3, 69.6, 67.4, 64.7, 57.1, 50.3, 40.5, 37.1, 36.9, 32.0, 29.9, 24.8, 22.2, 18.2, | ESI-MS m/z: 603 (M + H)⁺ |
| 69 | 573 | 2.00 | ¹H NMR (500 MHz, CDCl₃) δ 10.83 (s, 1H), 7.93 (s, 1H), 7.85 (d, J = 8.8 Hz, 2H), 7.81 (d, J = 8.8 Hz, 2H), 7.55 (d, J = 3.2 Hz, 1H), 7.06 (d, J = 3.3 Hz, 1H), 6.51 (s, 1H), 5.94 (d, J = 7.1 Hz, 1H), 4.57 (t, J = 5.0 Hz, 2H), 3.91 (t, J = 5.0 Hz, 2H), 3.77-3.70 (m, 1H), 3.68 (t, J = 6.0 Hz, 2H), 3.63-3.54 (m, 4H), 2.63 (s, 3H), 2.57 (s, 3H), 2.36 (t, J = 6.0 Hz, 2H), 1.89-1.81 (m, 2H), 1.68-1.52 (m, 3H), 1.36-1.04 (m, 5H). | ¹³C NMR: (125 MHz, CDCl₃) 170.2, 162.4, 155.7, 147.8, 142.7, 139.7, 139.5, 126.4, 125.4, 120.5, 119.6, 117.2, 108.4, 107.1, 105.7, 70.5, 70.3, 69.6, 67.5, 50.3, 48.1, 37.3, 33.1, 25.6, 24.9, 24.8, 18.2, | ESI-MS m/z: 596 (M + Na)⁺, 574 (M + H)⁺ |

TABLE 1-continued

| | | | | | |
|---|---|---|---|---|---|
| 70 | 545 | 3.55 | $^1$H NMR (500 MHz, CDCl$_3$) δ 10.88 (s, 1H), 7.96 (s, 1H), 7.88 (d, J = 8.7 Hz, 2H), 7.84 (d, J = 8.7 Hz, 2H), 7.60 (d, J = 3.3 Hz, 1H), 7.10 (d, J = 3.3 Hz, 1H), 6.55 (s, 1H), 6.19 (d, J = 6.0 Hz, 1H), 4.59 (t, J = 5.0 Hz, 2H), 4.40-4.30 (m, 1H), 3.97-3.89 (m, 2H), 3.68 (t, J = 6.1 Hz, 2H), 3.65-3.57 (m, 4H), 2.66 (s, 3H), 2.61 (s, 3H), 2.35 (t, J = 6.1 Hz, 2H), 2.32-2.24 (m, 2H), 1.87-1.77 (m, 2H), 1.70-1.61 (m, 2H). | $^{13}$C NMR: (125 MHz, CDCl$_3$) 170.2, 162.5, 155.7, 147.8, 142.7, 139.7, 139.5, 126.4, 125.4, 120.6, 119.7, 117.2, 108.5, 107.1, 105.7, 70.5, 70.3, 69.6, 67.4, 50.4, 44.6, 37.0, 31.2, 24.8, 18.3, 15.2, | ESI-MS m/z: 568 (M + Na)$^+$, 546 (M + H)$^+$ |

Example 11—An Activator Modified Glucocerebrosidase for Enzyme Replacement Therapy Introduction Gaucher's disease (GD) is a rare genetic lysosomal storage disorder caused by the functional deficiency of glucocerebrosidase (acid β-glucosidase, GCase) that results in multiple organ malfunction (Futerman and van Meer 2004). Heterozygous mutations in GCase is found as a major risk factor for Parkinson's disease (PD) (Sidransky, Nalls et al. 2009, Sidransky and Lopez 2012, Lin and Farrer 2014, Schapira, Olanow et al. 2014). Accumulation of glucocerebroside, the substrate of GCase, in neurons that promotes formation of toxic α-synuclein oligomers, which cause PD (Mazzulli, Xu et al. 2011). Enhance of GCase activity is thought to be a potential therapeutic strategy for GCase-associated synucleinopathies, including PD (Sardi, Clarke et al. 2013, Sybertz and Krainc 2014).

Treatments for GD include enzyme replacement therapy (ERT) or substrate reduction therapy by inhibition of glucosylceramide synthase (Bennett and Mohan 2013). Receptor-interacting protein kinase-3 (RIP3) had recently discovered as an emerging therapeutic target of GD (Vitner, Salomon et al. 2014). ERT has proved to be safe and effective over 20 years, and a reduction in organ volumes, improvement in hematological parameters and amelioration of bone pains have dramatically improved the quality of life for many patients (Futerman, Sussman et al. 2004, Weinreb, Goldblatt et al. 2013, Souza, Muniz et al. 2014). There are three recombinant enzymes with similar activity available for the treatment of GD today: imiglucerase, velaglucerase alfa, and taliglucerase alfa (Bennett and Mohan 2013) (Tekoah, Tzaban et al. 2013). However, because of the limited effectiveness of these GCase, the cost of ERT ranges from US$100,000 to more than $250,000 per year (Grabowski 2008), which impose burdens on patients. Engineering a more-stable enzyme, or an enzyme with a higher catalytic activity, could reduce the number of infusions and potentially also reduce cost (Futerman, Sussman et al. 2004).

Several different scaffolds of non-iminosugar inhibitory modulators (Zheng, Padia et al. 2007) and non-inhibitory modulator 1 (FIG. 1) (Patnaik, Zheng et al. 2012) were reported since 2007. These modulators are suggested to bind in other site than the active site, and stabilize the enzyme (Zheng, Padia et al. 2007) (Patnaik, Zheng et al. 2012). Modulator 1 can activate purified wt. GCase with AC$_{50}$ of 5.2 μM and around 100% maximum activation activity (Patnaik, Zheng et al. 2012). To improve the GCase enzyme activity and stability for ERT and study the activation mechanism of the modulators, in current study, we firstly report the high activation activators and an activator covalent modified GCase.

Results

Discovery of High Activation Activators.

To develop potent and high activation activators, the pyrazolopyrimidine ring of 1 was modified to give pyrrolopyrimidine scaffold compounds exhibiting higher enzyme activity. The alkyne group on the phenyl ring was coupled with an azide bearing a polyethylene glycol (PEG$_2$) linker by click reaction to give 2 (Scheme 1). With around 14 folds of maximum activity and AC$_{50}$ of 6.31 μM in 4MU-Glc substrate enzyme activity assay (FIG. 2A), 2 is, to our knowledge, among the most potent activators yet identified. Moreover, 2 highly activated (10 folds) Res-β-glc substrate hydrolysis at 50 μM, while lead compound 1 did not show any activation activity in the Res-β-glc substrate enzyme activity assay. Consistent with the previous report (Patnaik, Zheng et al. 2012), none of these compounds demonstrated any activation activity in current in vitro natural substrate assay.

Design of the Fluorescent Probe for Fluorescence Polarization Assay.

Figure 3:
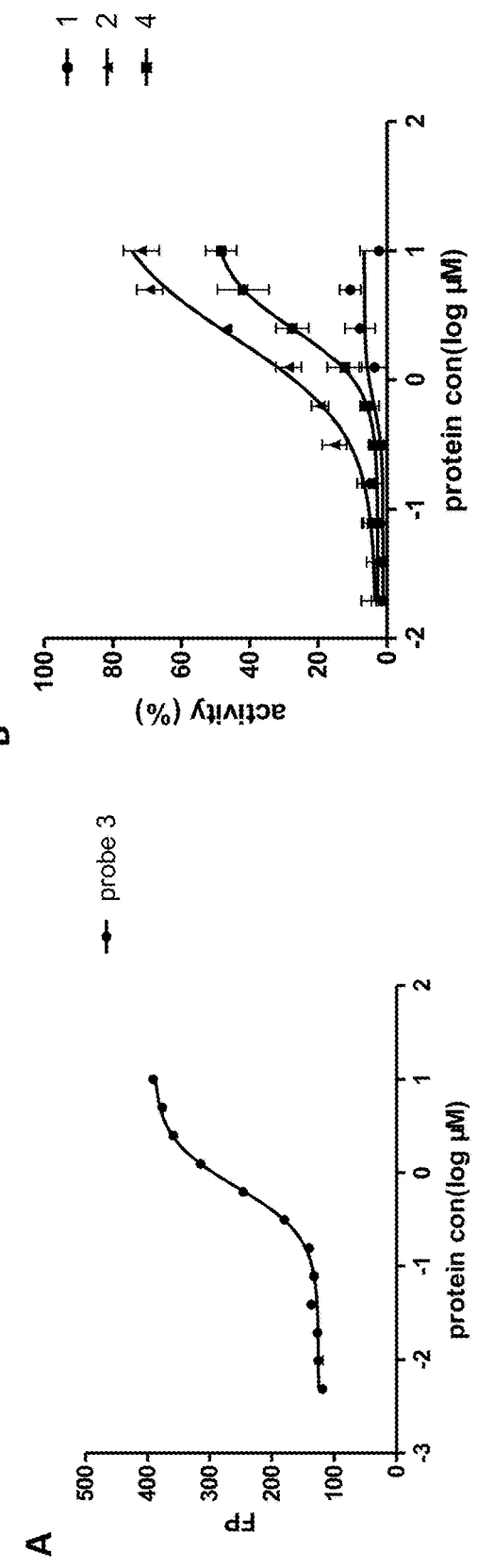
FIG. 3. FP curves for probes 3 and compete assay with compound 1 and 2.
Figure 4:
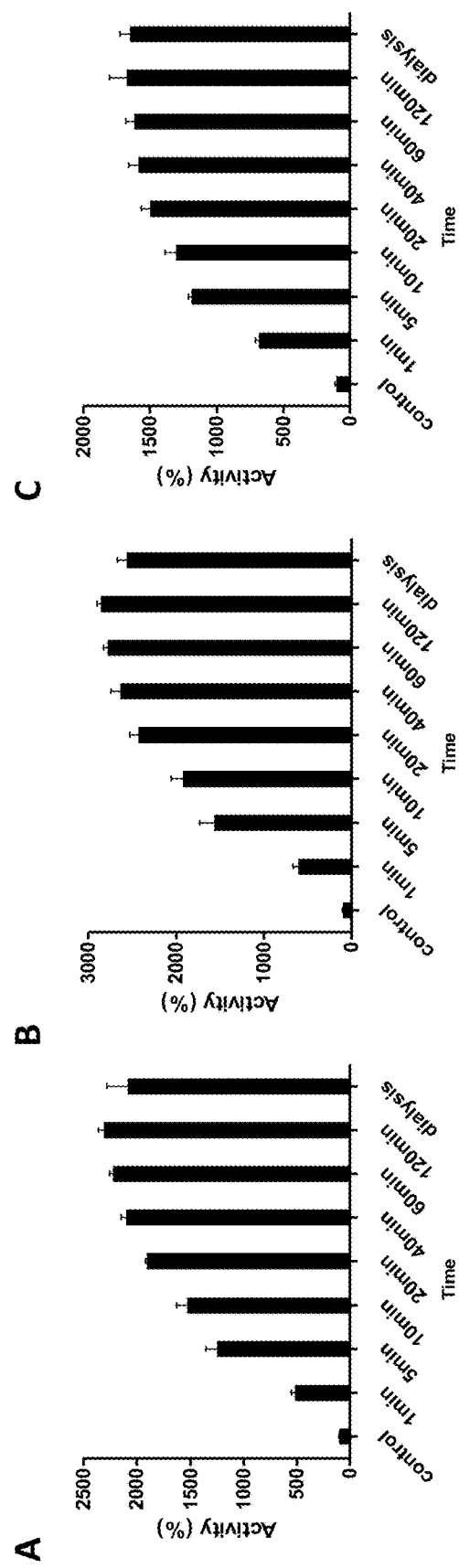
FIG. 4. GCase was activated by probe 4 in a time-dependent manner for A) 4MU-β-glc substrate; B) Res-β-glc substrate, and (C) natural substrate.

To facilitate the detection of the activator binding affinity, compound 2 was coupling with a fluorophore, to afford the probe 3 (Scheme 1). The fluorescence polarization (FP) signal was gradually saturated with the increased concentration of the enzyme (FIG. 3A). Probe 3 was observed to have a potent binding affinity with a Kd value of 0.71 μM, indicating that the probe 3 could bind to GCase directly. To determine the binding affinity of the activators, probe 3 was competed with different concentrations of compound 1 and 2, respectively. Compound 1 showed very weak activity in this assay, while compound 2 exhibited much higher activity (FIG. 3B).

Design of an Electrophilic Probe 4 and the Covalent Binding Assay.

Figure 2:
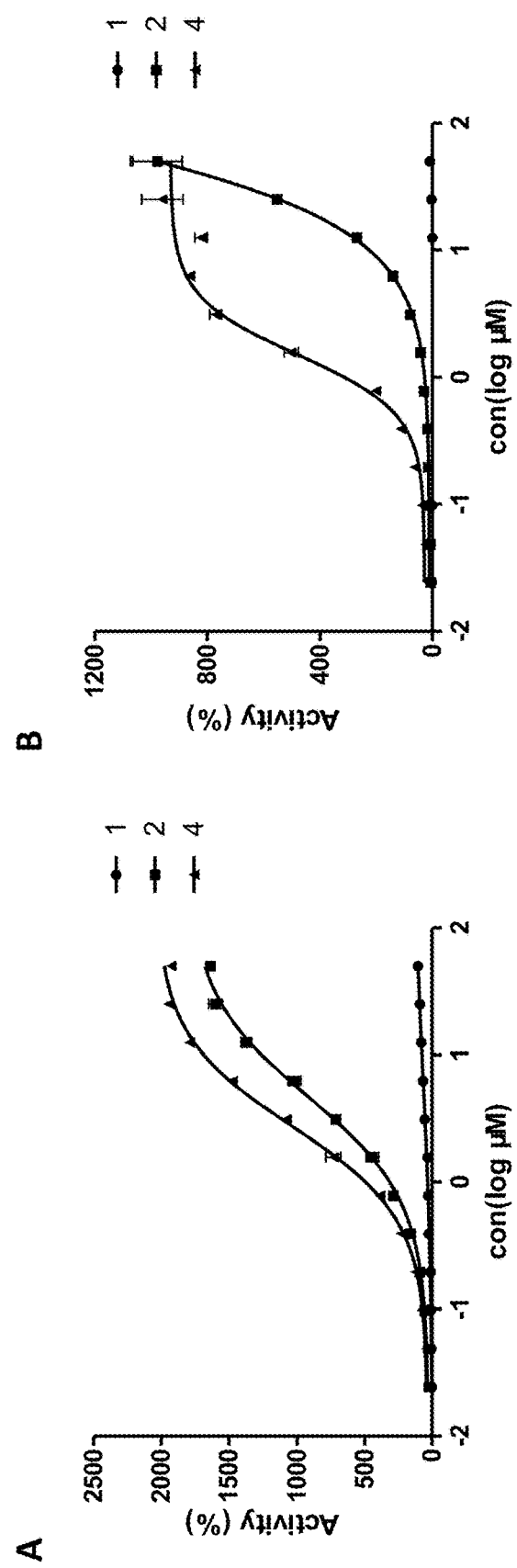
FIG. 2. Dose-response curves for the GCase activators 1, 2 and 4 with A) 4MU-Glc substrate; and B) red substrate.

Probe 4 was designed and synthesized to target the lysine residues surrounding the binding site by the reaction of NHS ester with primary amine (Scheme 1). The probe 4 also showed high activation activity in both of the 4MU-Glc (20 folds) and red substrates (10 folds) enzyme activity assays (FIGS. 2A and 2B).

Figure 5:
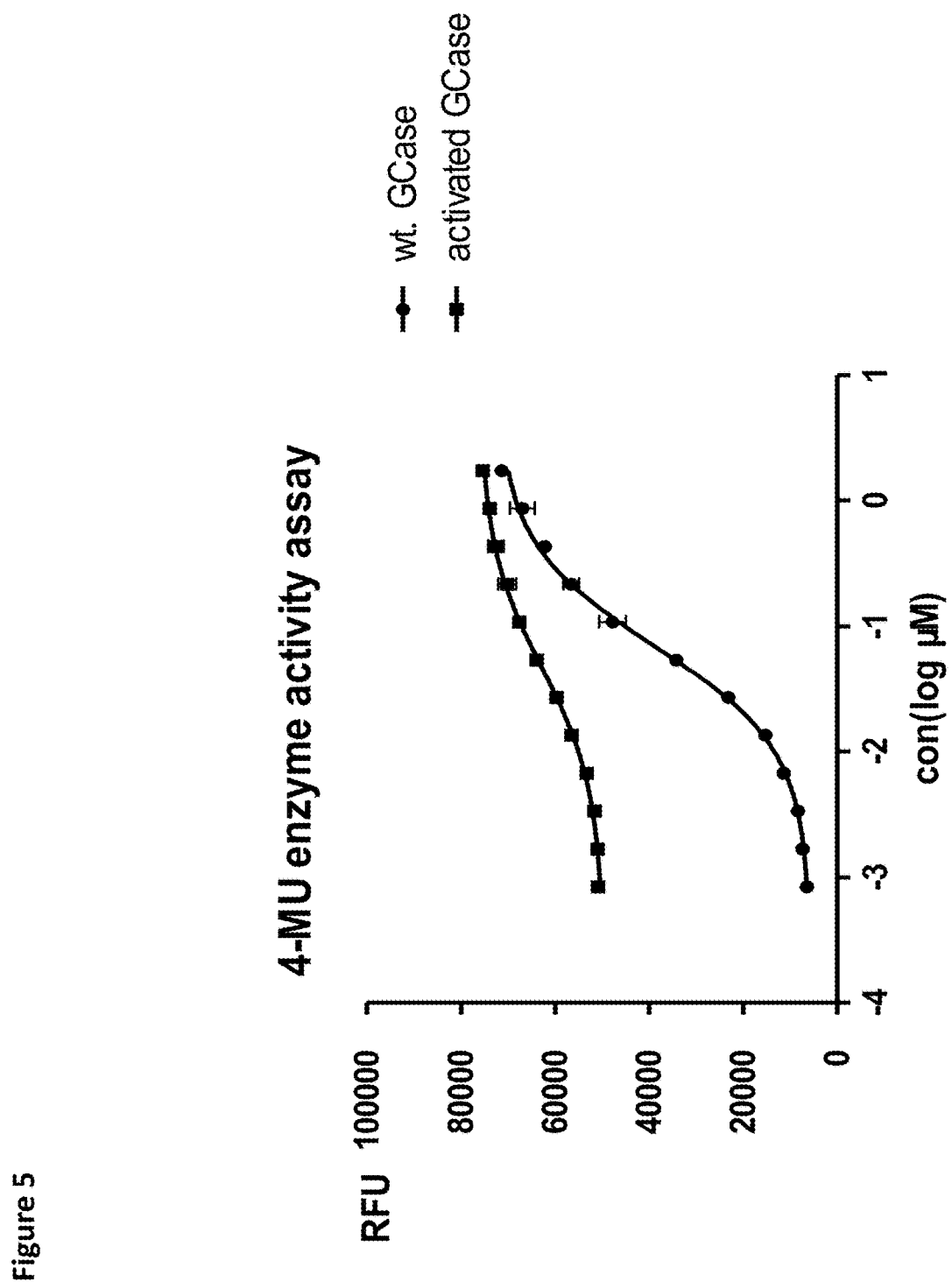
FIG. 5. The wt. and pre-activated GCase were activated by saposin C in a dose-dependent manner.

The probe 4 was subjected to the covalent binding assay against GCase. The reaction conditions, including the buffer pH value, the concentration of the protein and probe, and the reaction temperature were carefully adjusted to achieve the maximum activation. With the optimized reaction condition, the enzyme activity was activated in a time-dependent manner (FIG. 5). The enzyme could be activated by probe 4 with around 22 and 28 folds activity comparing to the wt. GCase in the 4MU-Glc substrate (FIG. 5A) and red substrate (FIG. 5B) enzyme activity assay respectively. To our surprise, the covalent activated enzyme also demonstrated 16 folds activity improvement in the natural substrate assay (FIG. 5C). The enzyme activity was not decreased significantly followed by dialysis in three substrate assays, indicating that the enzyme had been covalent modified by probe 4. This result was also confirmed by high-resolution LC-MS spectrum, indicating that GCase was modified by 1-3 ligands, despite the presence of twenty two lysine residues on the protein.

Saposin C Compete Assay with Probe 4 Pre-activated GCase.

The wt. GCase could be activated by Saposin C (Tamargo, Velayati et al. 2012), a natural co-factor of GCase in a dose-dependent manner with an $AC_{50}$ value of 100 nM (FIG. 5). However, the binding site and binding mode of saposin C remains unknown. To investigate whether saposin C and probe 4 share the same binding site, the covalent activated GCase was titrated with saposin C, and the enzyme activity was tested in the 4MU-Glc substrate enzyme activity assay. The pre-activated enzyme could be further activated by saposin C in a dose-dependent manner with an $AC_{50}$ value of 71 nM (FIG. 5). It seemed that the enzyme activity was modulated by the activator and saposin C in a synergy mode, suggesting that the binding site of the probe 4 and saposin C are different.

Enzyme Stability Assay in pH 4.7 Buffer and Human Plasma.

To test whether probe 4 changed the enzyme stability of GCase, we used two environments for GCase activity stability assay (Tekoah, Tzaban et al. 2013). The first one was citrate/phosphorylate buffer, which was at pH 4.7. In this condition, the wt. GCase only had about 15% activity left on day 4 (FIGS. 6A and 6B), which is similar to the previous research (Tekoah, Tzaban et al. 2013). An interesting finding was that even on day 10, activated GCase still had more than 20% activity left. This result suggested that the activated GCase not only had higher absolute GCase activity on each day, but also showed a strong delay of activity reduction after normalization in low pH buffer. One possible reason for the higher enzyme activity in low pH buffer was that activated GCase was stabilized by the covalent compound, and was more difficult to unfold.

Figure 6:
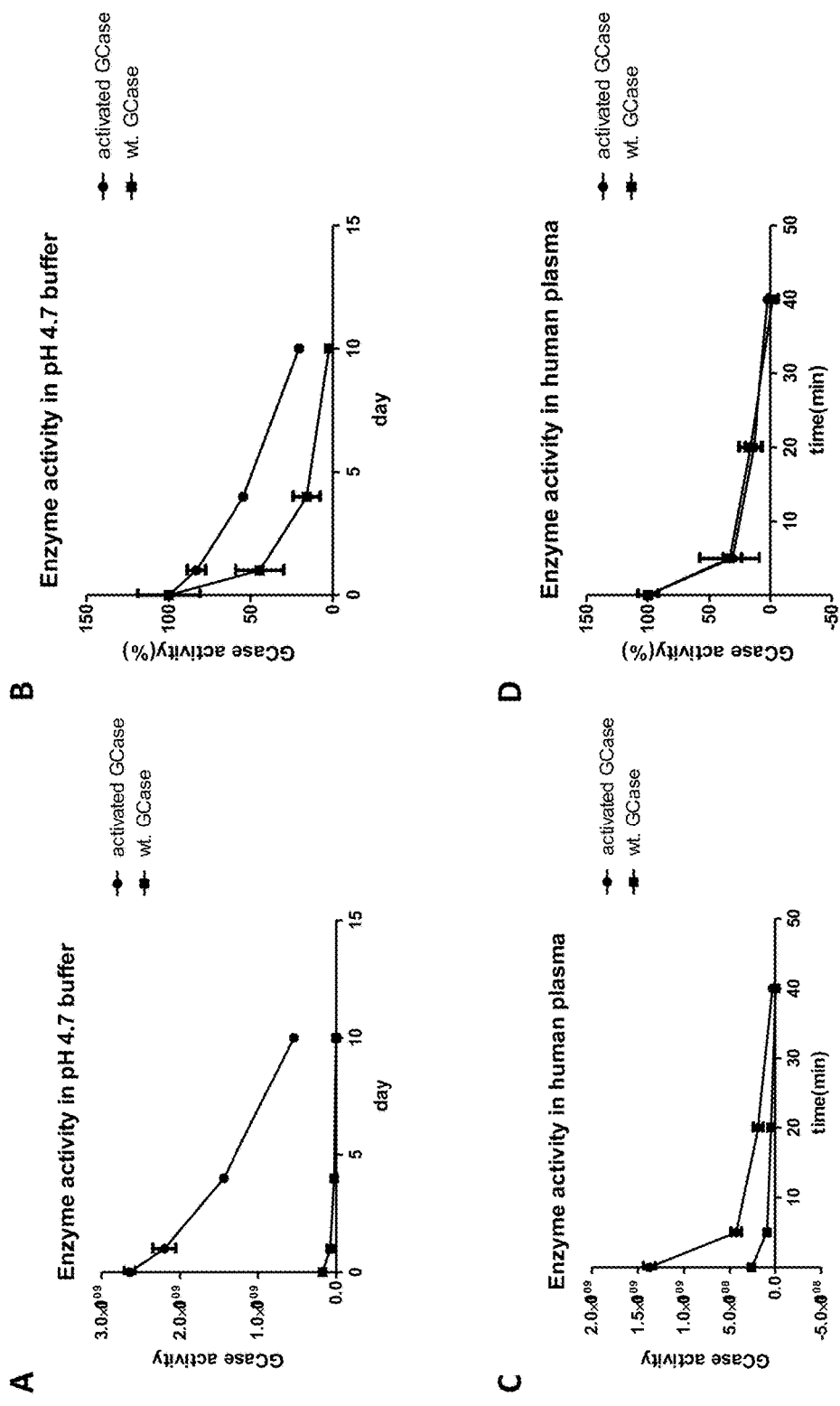
FIG. 6. Enzyme activity of the activated enzyme and wt. enzyme in pH 4.7 buffer and human plasma. A) Enzyme activity of activated GCase vs. wt. GCase tested by 4MU- β-glc substrate enzyme activity assay in pH 4.7 buffer; B) Normalization of the enzyme activity in pH 4.7 buffer; C) Enzyme activity of activated GCase vs wt. GCase tested by 4MU-β-glc substrate enzyme activity assay in human plasma; D) Normalization of the enzyme activity in human plasma FIG. 7. Cell uptake assay (U937 macrophage). A) Enzyme activity of activated GCase vs wt. GCase tested by 4MU-β-glc substrate enzyme activity assay; B) Western blot: endogenous, activated and wt. GCase.

Then we tested both the activated GCase and wt. GCase in human plasma (pH 7.4). To our surprise, even though the activated GCase had higher activity at each time point, after normalization, the activated GCase and wt. GCase showed similar enzyme activity stability curves (FIGS. 6C and 6D). This result suggested that probe 4 didn't affect the degradation of GCase in human plasma.

U937 Macrophage Uptake Assay.

Figure 7:
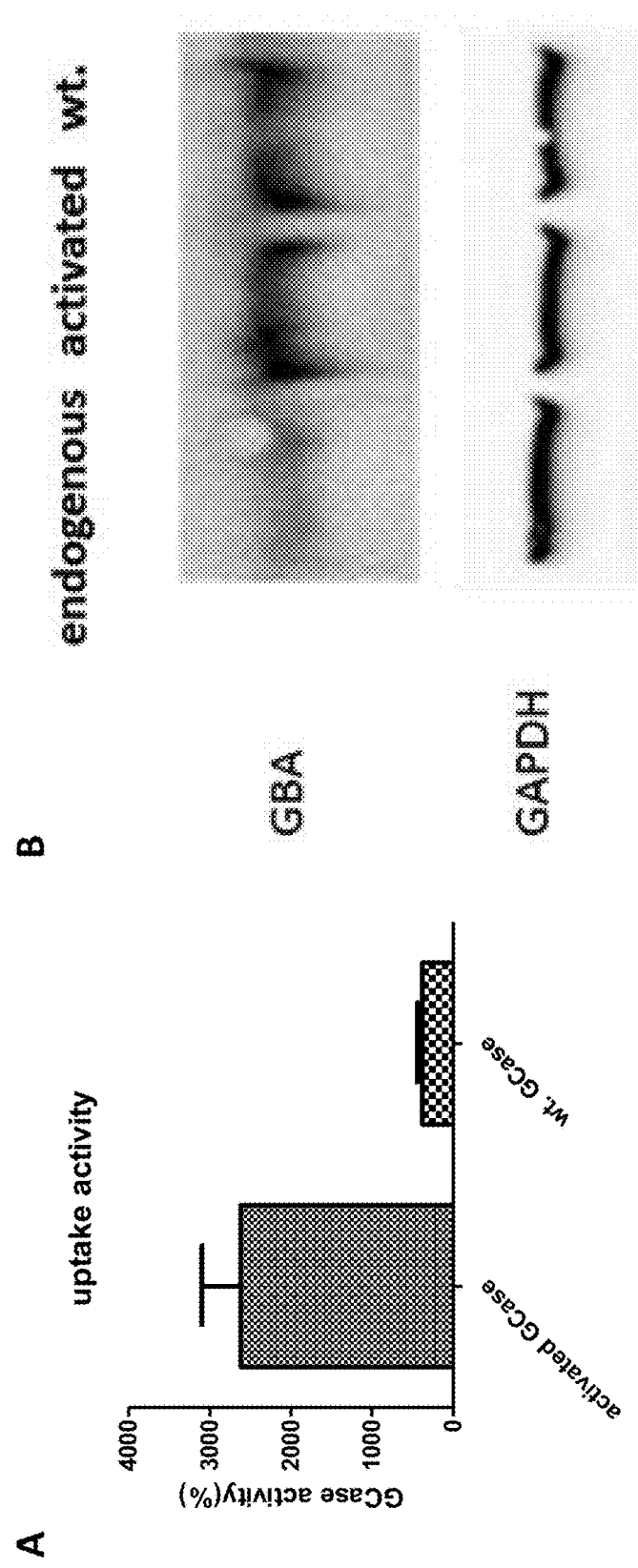

The following question we asked was whether human macrophage cell, GD's target cell, could uptake activated GCase normally. After PMA induction, we treated the U937 cell line with both activated GCase and wt. GCase (Tekoah, Tzaban et al. 2013). The activated GCase showed more than 25 folds activity compared to endogenous GC, while wt. GCase had only about 3 folds activity (FIG. 7A), despite the protein uptake level of the activated GCase and wt. GCase were equal (FIG. 7B). These results indicated that probe 4 would not affect the uptake of GCase into macrophage cells but it could improve GCase enzyme activity in cells.

Discussion

In over two decades, enzyme replacement therapy (ERT) had achieved great success in the treatment of genetic lysosomal storage diseases, such as Gaucher's disease (Futerman, Sussman et al. 2004) Fabry disease (Pisani, Visciano et al. 2012) and Pompe disease (Angelini and Semplicini 2012). However, the major issue of ERT is the cost of the enzyme treatment (Grabowski 2008), which preventing many of the patients access this therapy. In this study, we discovered the high activation compounds and use them for specific modification of recombinant glucocerebrosidase to improve the enzyme activity as well as stability.

Lead compound 1 was discovered as a non-inhibitory chaperone in 2012 (Patnaik, Zheng et al. 2012). In our effort to discover potent activators, according to our SAR study, a new pyrrolopyrimidine scaffold had been found to have high activation activity and binding affinity than 1. Because of low solubility of these activators in aqueous solution, further modification on the para position of the phenyl ring with a trizole ring bearing a PEG linker had been discovered to present higher activation activity and better solubility. Compound 2, with a $PEG_2$ linker, was found to give the highest activation in these series of activators.

To evaluate the SAR of these activators, a binding assay is needed to evaluate their binding affinity. The only detection method reported for the binding of GCase and the activators is microscale thermophoresis (MST) (Patnaik, Zheng et al. 2012). Some other biophysics techniques, such as isothermal titration calorimetry (ITC), surface plasmon resonance (SPR), and fluorescence thermal shift, had been attempted to find out the binding of the GCase activators. Unfortunately, these methods failed to give any positive result in our study. Fluorescence polarization (FP) assay is a homogeneous method that allows rapid and quantitative analysis of diverse molecular interactions and enzyme activities (Rossi and Taylor 2011). A fluorescent probe was designed and synthesized to measure the binding affinity of the probe and GCase. Probe 3 was measured to have an Kd value around 0.71 uM, indicating that this probe binds tightly with GCase. With this FP assay, we could detect the binding of the compounds with GCase, whatever they are activators, inhibitors or just binders. So this method could be further utilized in the high throughput screening (HTS) to discover more diverse compounds as the modulators of GCase.

Since we have the high activation activators in hand, we hypothesized that once GCase was covalent modified by our compound, the enzyme activity could be enhanced to the maximum activity of the activator because the local concentration of the activator is high. Primary amine of lysine residue, a high reactive group exists on most protein surface, could be modified by many diverse chemicals (Nakamura, Kawai et al. 2009, Choi, Connelly et al. 2010). NHS ester had been use to react with lysine in a plenty of biological studies (Nanda and Lorsch 2014). Based on our SAR study, we found a $PEG_2$ linker was the suitable length to achieve maximum enzyme activity. In the covalent binding assay, wt. GCase was modified and activated by probe 4 in a time-dependent manner. The maximum enzyme activity could be achieved by using two equivalent of 4 in one hour at pH 7.2. Either higher pH value or increased ratio of probe 4 could reduce the enzyme activity, suggesting that the non-specified binding of probe 4 will affect the enzyme activity. Considering of the conditions we used in the covalent binding assay, this result demonstrated that the elevated enzyme activity coming from the scaffold of the ligand and the specific covalent modification of the enzyme.

Saposin C binding mode had been studied and modeled (Atrian, Lopez-Vinas et al. 2008). If the activated enzyme could not be activated by Saposin C, the binding site of the activator and Saposin C would be the same. Actually, the activated GCase could be further activated by Saposin C. The modification of the activator did not interfere with Saposin C interaction, indicating that the binding site of the activator is different from Saposin C. The result also suggested that our high activated GCase may not require Saposin C for further activation. This enzyme could be used for the patients with Saposin C mutation.

To evaluate whether the activated enzyme could be used in ERT, we examined the enzyme stability and cell uptake property. The activated enzyme demonstrated much more stability in acidic buffer and same stability in human plasma to wt. GCase. In U937 uptake assay, the same amount of the activated GCase could be uptaken by PMA induced U937 macrophage cell comparing to wt. GCase, indicating that compound modification does not affect the GCase uptake process. With much higher enzyme activity and stability of the activated GCase in the acidic condition, as demonstrated in this study, we may suggest that diminished injection dose of this enzyme might be used in ERT for GD.

In addition, more different recombinant lysosomal enzymes, such as α-1-iduronidase, α-galactosidase, α-glucosidase, N-acetylgalactosamine 4-sulfatase and iduronate sulfatase, had been approved to treat for their respective deficiency diseases (MPS I, Fabry disease, Pompe disease, MPS VI and MPS II)(Desnick and Schuchman 2012, Valayannopoulos 2013). Wide application of our activator modified enzyme approach has the potential to improve the treatment in other lysosomal storage diseases.

Methods

Biology

4-Methylumbelliferyl β-D-glucopyranoside (4MU-β-glc), a blue-fluorogenic substrate, resorufin β-D-glucopyranoside (Res-β-glc), a red-fluorogenic substrate, and the buffer components were purchased from Sigma-Aldrich (St. Louis, Mo.). Natural substrate, glucosylceramide was purchased from Avanti Polar Lipids, Inc. (Alabaster, Ala.). The Amplex Red Glucose/Glucose Oxidase Assay Kit was purchased from Invitrogen (Eugene, Oreg.) to measure the amount of glucose produced when glucosylceramide is cleaved by glucocerebrosidase.

The recombinant wt. enzyme velaglucerase alfa (Vpriv®, Shire Human Genetic Therapies, Inc.) was obtained from residual solution after clinical infusions. The GCase activity assay buffer was composed of 50 mM citric acid, 176 mM $K_2HPO_4$, and 0.01% Tween-20 at pH 5.9. A solution of 1 M sodium hydroxide and 1 M glycine was used as the stop solution for the 4MU-β-glc substrate assay.

Compound Activity Assay with 4MU-β-glc Substrate and Res-β-glc Substrate.

The compounds in DMSO solution 0.5 µL/well was transferred to a black 96-well plate (the final titration was 24 nM to 50 µM, 12 concentrations). 33.5 µL enzyme solution (7.5 nM final concentration) was transferred to the wells. After 5 min of incubation at room temperature, the enzyme reaction was initiated by the addition of 33 µL/well 4MU-Glc substrate or 66.5 µL/well red substrate. Final concentrations of the 4MU-Glc substrate and Res-Glc substrate were 1.5 mM and 30 µM, respectively. The red substrate reaction was measured in the Biotek Synergy H1 multi-mode plate reader with Ex=573 nm and Em=610 nm at 37° C. in every 20 seconds for 30 min. The 4MU-Glc substrate reaction was terminated by the addition of 33 µL/well stop solution (1 M NaOH and 1 M glycine mixture, pH 10) after 30 min of incubation at 37° C. The fluorescence was then measured in the plate reader with Ex=365 nm and Em=440 nm.

Compound Activity Assay with Natural Substrate.

The compounds were tested with natural substrate by using the slight modified method as described previously (Motabar, Goldin et al. 2012). The compounds in DMSO solution 0.5 µL/well was transferred to a black 96-well plate (the final titration was 24 nM to 50 µM, 12 concentrations). 33.5 µL enzyme solution was transferred to the wells. After 5 min of incubation at room temperature, the enzyme reaction was initiated by the addition of 16 µL/well natural substrate. Final concentrations of the natural substrate (glucosylceramide) was 100 µM. The plate was incubated for 30 min at 37° C., and was added the Amplex Red Glucose/Glucose Oxidase Assay buffer (50 µL/well). The plate was measured in the Biotek Synergy H1 multi-mode plate reader with Ex=573 nm and Em=610 nm at 37° C. every 20 seconds for 30 min.

Fluorescence Polarization (FP) Assay.

The fluorescent probe 3 (25 nL/well, 50 nM final concentration) was transferred to a 384-wells black plate by using Labcyte Echo 550 Liquid Handler system. The 25 µL/well enzyme dilutions in GCase enzyme activity buffer (the final titration was 5 nM to 10 µM, 10 concentrations, 2 times dilution) were added to the plate, and shook at room temperature in dark for 20 min. The fluorescence polarization was measured in Molecular Devices Analyst GT with Ex=535 nm and Em=580 nm, G Factor=1.05.

Binding Affinity Test by FP Assay.

The enzyme in GCase enzyme activity buffer (25 µL/well) was added to a 384-wells black plate, The fluorescent probe 3 (25 nL/well, 50 nM final concentration) was transferred to a 384-wells black plate by using Labcyte Echo 550 Liquid Handler system. Compounds 1, and 2 in DMSO stock solution (50 nL) (the final titration was 19.5 nM to 10 µM, 10 concentrations) were transferred to the plate. The plate was shook at room temperature in dark for 20 min. The fluorescence polarization was measured in Molecular Devices Analyst GT with Ex=535 nm and Em=580 nm, G Factor=1.05.

Saposin C Activation Assay with 4MU-Glc Substrate.

Saposin C (0.5 µL/well) was added to a black 96-well plate (the final titration was 1.72 nM to 1.76 µM, 12 concentrations). The compound 4 activated enzyme and wt. enzyme (33.5 µL/well, 7.5 nM final concentration) in assay buffer (50 mM Citric acid, 176 mM $K_2HPO_4$, 0.01% tween-20, 0.01% (g/mL) phosphatidylserine, pH 4.7) was added to the wells, respectively. After 5 min of incubation at room temperature, the enzyme reaction was initiated by the addition of 33 µL/well 4MU-Glc substrate. Final concentrations of the 4MU-Glc substrate was 1.5 mM. The reaction was terminated by the addition of 33 µL/well stop solution (1 M NaOH and 1 M glycine mixture, pH 10) after 30 min of incubation at 37° C. The fluorescence was then measured in the plate reader with Ex=365 nm and Em=440 nm.

High Resolution HPLC-MS Spectrum.

The enzyme was treated with compound 4 at pH 7.2 for 60 min as described above. The sample was dialyzed with 0.1 M Tris pH 7.2 buffer and analyzed on Agilent 6210A LC-TOF mass spectrometer equipped with a C8 column.

Differentiation of Human U937 Macrophage Cells.

Human monocyte cell line U937 was optimally differentiated into macrophages by the addition of 75 ng/ml PMA (Brumshtein, Salinas et al. 2010) to the monocyte culture for 3 days (in 75 cm² flasks). Macrophages were enriched by adhesion to the culture plate and identified by morphology and receptor staining.

GCase Uptake Studies in Macrophage Cells.

The assay was carried out according to the reported method (Tekoah, Tzaban et al. 2013) with slight modification. The enzyme was treated with compound 4 or DMSO at pH 7.2 for 60 min as described above, then dialyzed with PBS. U937 cells, after differentiation (~1.6*106 cells), were incubated with 60 µg/ml of the activated enzymes and wt. enzyme in F12K medium for 10 min at 5% $CO_2$, 37° C. incubator. The cells were then washed twice with ice cold PBS enriched with Mannan (1 mg/ml). To further ensure release of any proteins bound non-specifically to the membrane half of the cells were washed with ice cold glycine buffer: (0.8% NaCl, 0.038% KCl, 0.01% $MgCl_2$, 0.01% $CaCl_2$, 0.7% glycine [pH 3]) followed by two additional cold PBS washes. The other half of the wells were used as controls for measuring total enzymatic activity (bound and internalized enzyme). The cells were lysed by adding β-glucocerebrosidase activity buffer (60 mM phosphate-citrate buffer; 0.15% Triton X-100; 0.125% sodium taurocholate, pH 5.5), followed by pipetting and one freeze/thaw cycle. The obtained lysates were subjected to determination of enzymatic activity using the colorimetric method detailed above. The total enzymatic activity was normalized to total soluble proteins as measured by Bradford assay. The effective uptake was calculated as the percentage of activity within the cells out of the total enzymatic activity of the controls.

Chemistry

Commercially available reagents and solvents were used without further purification. Compounds were synthesized and analyzed as indicated in this example and the foregoing examples. All reactions were monitored by thin layer chromatography (TLC) with 0.25 mm Silicycle extra hard 250 µM TLC plates (60 F254). Purification of reaction products was carried out by flash chromatography using Agilent 971-FP flash purification system with Silicycle Silica Gel columns (4 g, 12 g, 24 g, 40 g or 80 g). The purity of all compounds was over 95% and was analyzed with Agilent 1260 Infinity HPLC system. $^1H$ NMR spectra and $^{13}C$ NMR were obtained using a Bruker Avance III 500 MHz system (500 MHz for $^1H$ NMR and 125 MHz for $^{13}C$ NMR) spectrometer. Chemical shifts are reported relative to chloroform ($\delta$=7.26) for $^1H$ NMR and chloroform ($\delta$=77.16) for $^{13}C$ NMR or dimethyl sulfoxide ($\delta$=2.50) for $^1H$ and dimethyl sulfoxide ($\delta$=39.52) for $^{13}C$ NMR. Data are reported as (br=broad, s=singlet, d=doublet, t=triplet, q=quartet, m=multiplet). Mass spectra were obtained using Bruker AmaZon SL system.

REFERENCES

Angelini, C. and C. Semplicini (2012). "Enzyme replacement therapy for Pompe disease." Curr Neurol Neurosci Rep 12(1): 70-75.

Atrian, S., et al. (2008). "An evolutionary and structure-based docking model for glucocerebrosidase-saposin C and glucocerebrosidase-substrate interactions—relevance for Gaucher disease." Proteins 70(3): 882-891.

Bennett, L. L. and D. Mohan (2013). "Gaucher disease and its treatment options." Ann Pharmacother 47(9): 1182-1193.

Brumshtein, B., et al. (2010). "Characterization of gene-activated human acid-beta-glucosidase: crystal structure, glycan composition, and internalization into macrophages." Glycobiology 20(1): 24-32.

Choi, S., et al. (2010). "Chemoselective small molecules that covalently modify one lysine in a non-enzyme protein in plasma." Nature Chemical Biology 6(2): 133-139.

Desnick, R. J. and E. H. Schuchman (2012). "Enzyme replacement therapy for lysosomal diseases: lessons from 20 years of experience and remaining challenges." Annu Rev Genomics Hum Genet 13: 307-335.

Futerman, A. H., et al. (2004). "New directions in the treatment of Gaucher disease." Trends in Pharmacological Sciences 25(3): 147-151.

Futerman, A. H. and G. van Meer (2004). "The cell biology of lysosomal storage disorders." Nat Rev Mol Cell Biol 5(7): 554-565.

Grabowski, G. A. (2008). "Phenotype, diagnosis, and treatment of Gaucher's disease." Lancet 372(9645): 1263-1271.

Lin, M. K. and M. J. Farrer (2014). "Genetics and genomics of Parkinson's disease." Genome Medicine 6.

Mazzulli, J. R., et al. (2011). "Gaucher disease glucocerebrosidase and alpha-synuclein form a bidirectional pathogenic loop in synucleinopathies." Cell 146(1): 37-52.

Motabar, O., et al. (2012). "A high throughput glucocerebrosidase assay using the natural substrate glucosylceramide." Anal Bioanal Chem 402(2): 731-739.

Nakamura, T., et al. (2009). "Covalent modification of lysine residues by allyl isothiocyanate in physiological conditions: plausible transformation of isothiocyanate from thiol to amine." Chem Res Toxicol 22(3): 536-542.

Nanda, J. S. and J. R. Lorsch (2014). "Labeling a Protein with Fluorophores Using NHS Ester Derivitization." Laboratory Methods in Enzymology: Protein Pt A 536: 87-94.

Patnaik, S., et al. (2012). "Discovery, structure-activity relationship, and biological evaluation of noninhibitory small molecule chaperones of glucocerebrosidase." J Med Chem 55(12): 5734-5748.

Pisani, A., et al. (2012). "Enzyme replacement therapy in patients with Fabry disease: state of the art and review of the literature." Mol Genet Metab 107(3): 267-275.

Rossi, A. M. and C. W. Taylor (2011). "Analysis of protein-ligand interactions by fluorescence polarization." Nat Protoc 6(3): 365-387.

Sardi, S. P., et al. (2013). "Augmenting CNS glucocerebrosidase activity as a therapeutic strategy for parkinsonism and other Gaucher-related synucleinopathies." Proceedings of the National Academy of Sciences of the United States of America 110(9): 3537-3542.

Schapira, A. H. V., et al. (2014). "Slowing of neurodegeneration in Parkinson's disease and Huntington's disease: future therapeutic perspectives." Lancet 384(9942): 545-555.

Sidransky, E. and G. Lopez (2012). "The link between the GBA gene and parkinsonism." Lancet Neurology 11(11): 986-998.

Sidransky, E., et al. (2009). "Multicenter analysis of glucocerebrosidase mutations in Parkinson's disease." N Engl J Med 361(17): 1651-1661.

Souza, A. M., et al. (2014). "Study of enzyme replacement therapy for Gaucher Disease: comparative analysis of clinical and laboratory parameters at diagnosis and after two, five and ten years of treatment." Rev Bras Hematol Hemoter 36(5): 345-350.

Sybertz, E. and D. Krainc (2014). "Development of targeted therapies for Parkinson's disease and related synucleinopathies." J Lipid Res 55(10): 1996-2003.

Tamargo, R. J., et al. (2012). "The role of saposin C in Gaucher disease." Mol Genet Metab 106(3): 257-263.

Tekoah, Y., et al. (2013). "Glycosylation and functionality of recombinant beta-glucocerebrosidase from various production systems." Bioscience Reports 33: 771-U272.

Toja, E., et al. (1986). "Pyrrolopyridine Analogs of Nalidixic-Acid 0.1. Pyrrolo[2,3-B]Pyridines." Journal of Heterocyclic Chemistry 23(5): 1555-1560.

Valayannopoulos, V. (2013). "Enzyme replacement therapy and substrate reduction therapy in lysosomal storage disorders with neurological expression." Handb Clin Neurol 113: 1851-1857.

Vitner, E. B., et al. (2014). "RIPK3 as a potential therapeutic target for Gaucher's disease." Nature Medicine 20(2): 204-208.

Weinreb, N. J., et al. (2013). "Long-term clinical outcomes in type 1 Gaucher disease following 10 years of imiglucerase treatment." J Inherit Metab Dis 36(3): 543-553.

Zheng, W., et al. (2007). "Three classes of glucocerebrosidase inhibitors identified by quantitative high-throughput screening are chaperone leads for Gaucher disease." Proc Natl Acad Sci USA 104(32): 13192-13197.

Example 12—Synthesis and Testing of Additional Substituted Quinazoline Compounds Additional compounds were prepared and tested according to the procedures provided in the examples above. Results are shown in Table 2.

TABLE 2

| No. | Structure | MW | Activity $AC_{50}$ or $IC_{50}$ (μM) |
|---|---|---|---|
| 71 | 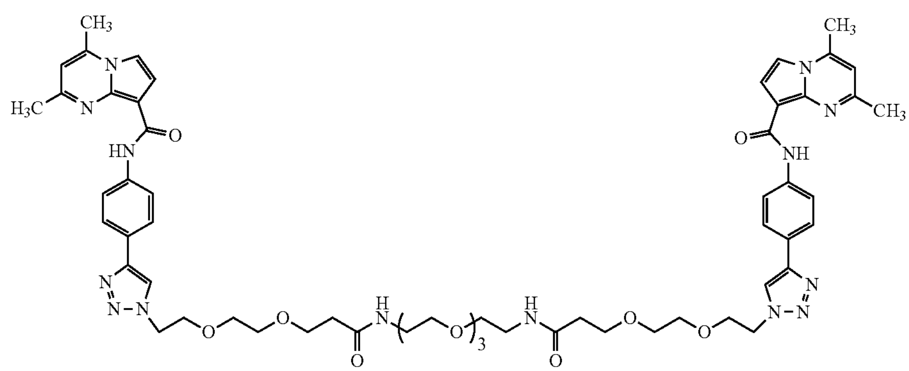 | 1140 | 1.26 activator |
| 72 | 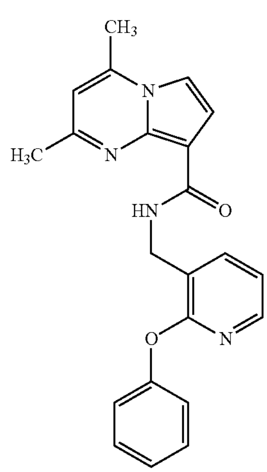 [SMILES: Cc1cc(C)n2ccc(C(=O)NCc3cccnc3Oc3ccccc3)c2n1] | 370 | 6.13 activator |

TABLE 2-continued
| No. | Structure | MW | Activity AC$_{50}$ or IC$_{50}$ (μM) |
|---|---|---|---|
| 73 | 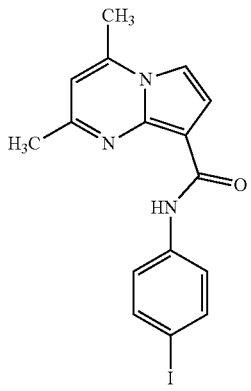 [SMILES: Cc1cc(C)n2ccc(C(=O)Nc3ccc(I)cc3)c2n1] | 391 | 0.316 activator |
| 74 | 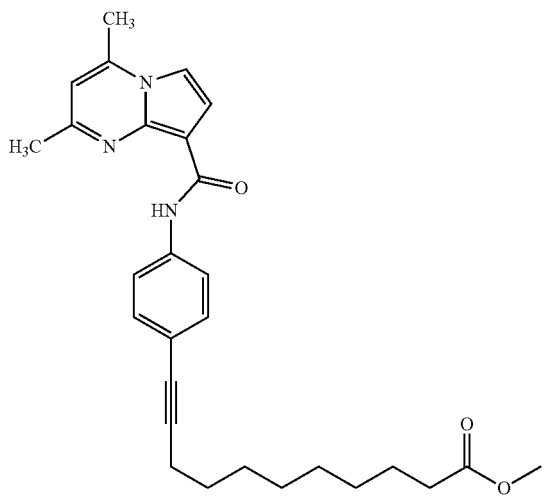 | 459 | 0.71 activator |
| 75 | 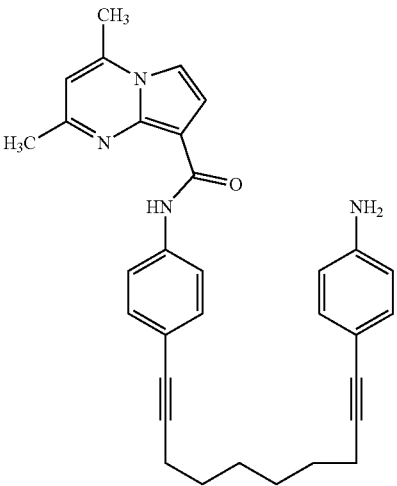 [SMILES: Cc1cc(C)n2ccc(C(=O)Nc3ccc(C#CCCCCCCC#Cc4ccc(N)cc4)cc3)c2n1] | 488 | 1.26 activator |

TABLE 2-continued
| No. | Structure | MW | Activity AC$_{50}$ or IC$_{50}$ (μM) |
|---|---|---|---|
| 76 | 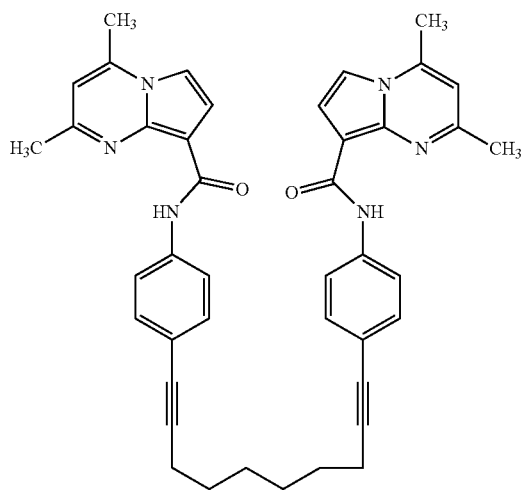 | 660 | 28.18 activator |
| 77 | 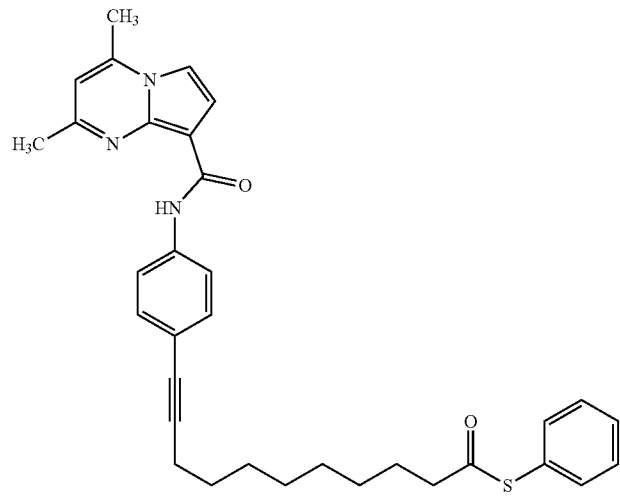 [SMILES: Cc1cc(C)n2ccc(C(=O)Nc3ccc(C#CCCCCCCCCC(=O)Sc4ccccc4)cc3)c2n1] | 537 | NA |
| 78 | 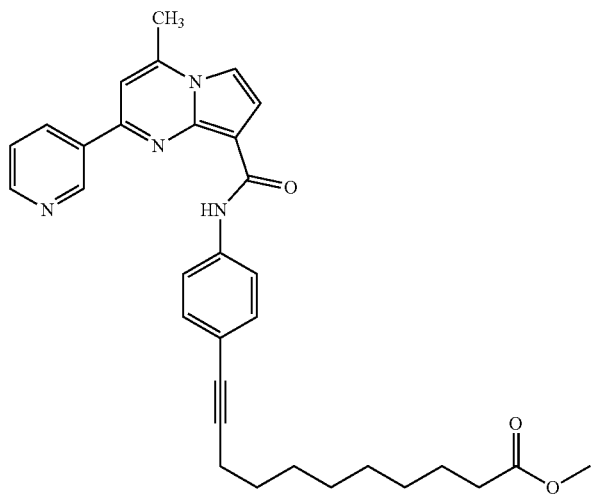 [SMILES: COC(=O)CCCCCCCCC#Cc1ccc(NC(=O)c2ccn3c(C)cc(-c4cccnc4)nc23)cc1] | 522 | 0.71 activator |

TABLE 2-continued

| No. | Structure | MW | Activity AC$_{50}$ or IC$_{50}$ (μM) |
|---|---|---|---|
| 79 | 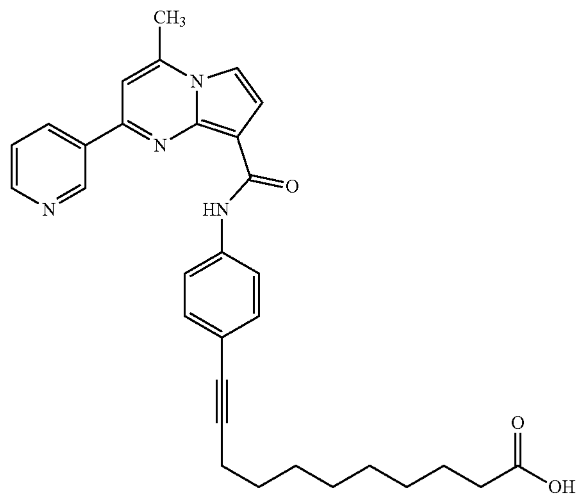 [SMILES: Cc1cc(-c2cccnc2)nc2c(C(=O)Nc3ccc(C#CCCCCCCCCC(=O)O)cc3)ccn12] | 508 | 3.54 activator |
| 80 | 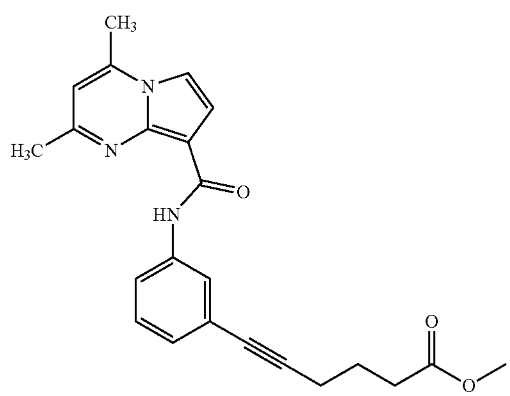 | 389 | activator |
| 81 | 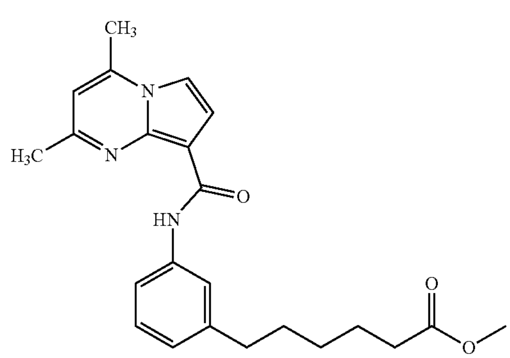 | 393 | 1.78 activator |

TABLE 2-continued

| No. | Structure | MW | Activity AC$_{50}$ or IC$_{50}$ (μM) |
|---|---|---|---|
| 82 | 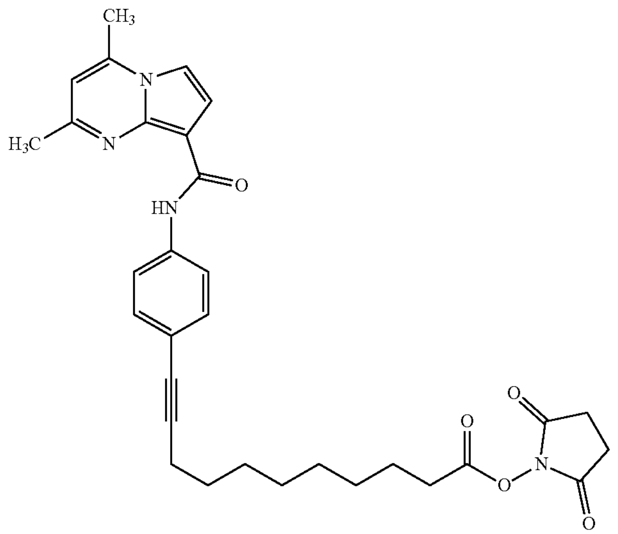 [SMILES: Cc1cc(C)n2ccc(C(=O)Nc3ccc(C#CCCCCCCCCC(=O)ON4C(=O)CCC4=O)cc3)c2n1] | 542 | 0.8 activator |
| 83 | 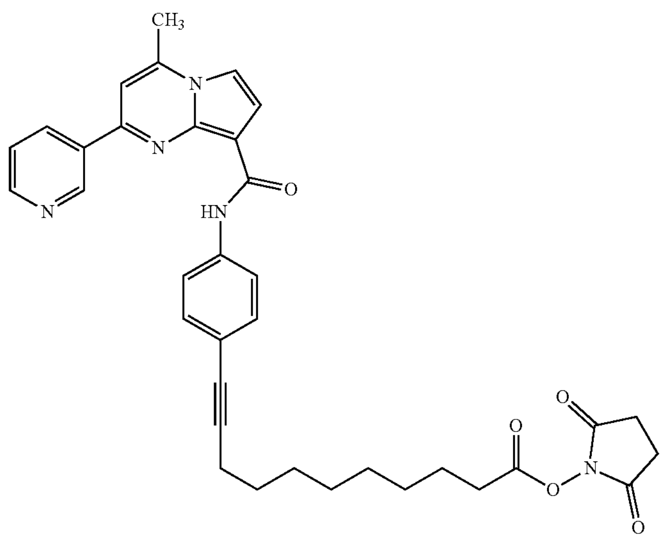 [SMILES: Cc1cc(-c2cccnc2)nc2c(C(=O)Nc3ccc(C#CCCCCCCCCC(=O)ON4C(=O)CCC4=O)cc3)ccn12] | 605 | 0.56 activator |
| 84 | n = 1-6 | | |

TABLE 2-continued
| No. | Structure | MW | Activity AC$_{50}$ or IC$_{50}$ (μM) |
|---|---|---|---|
| 85 | 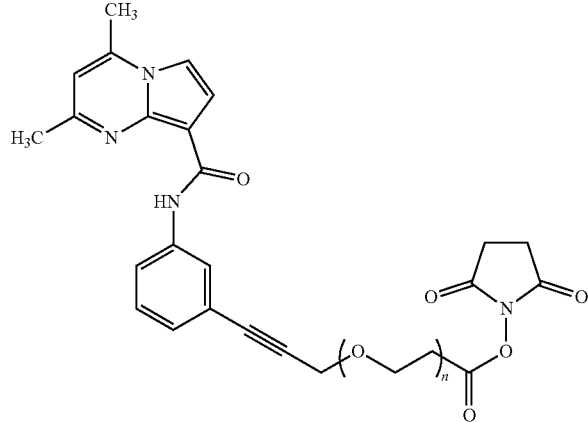<br>n = 1-4 | | |
| 86 | 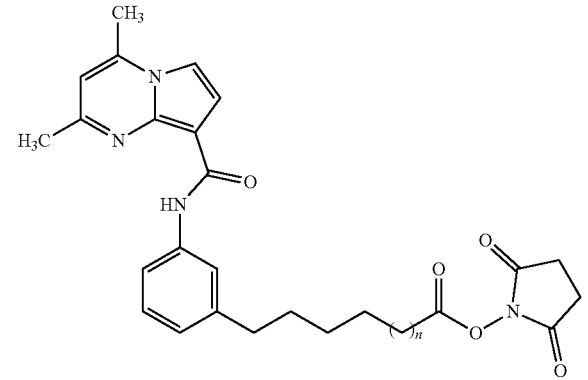<br>n = 1-6 | | |
| 87 | 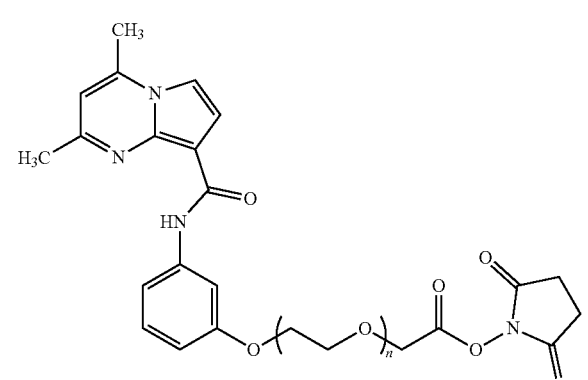<br>n = 1-4 | | |

TABLE 2-continued

| No. | Structure | MW | Activity AC$_{50}$ or IC$_{50}$ (μM) |
|---|---|---|---|
| 88 | (structure shown, n = 1-6) | | |
| 89 | (structure shown, n = 1-4) | | |

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:
1. A compound or a salt or solvate thereof having a formula:

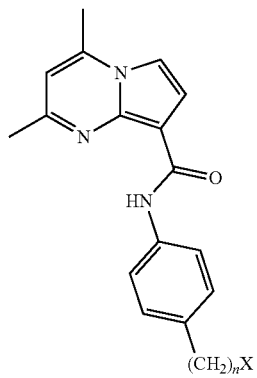

wherein:
n is 0-2; and
X is selected from hydrogen, alkyl, halo, haloalkyl, phenyl optionally substituted with alkyl or halo, alkylamino, N-pyrrolidinyl, alkyl-N-piperidinyl, 4-N,N-dialkylamino-N-piperidinyl, N-piperazinyl, N-alkyl-N- piperazinyl, N-benzyl-N-piperazinyl, N-morpholinyl, azido, hydroxyl, alkylhydroxyl, alkynylphenyl, phenoxy, oxophenyl, and oxyalkylcarboxyl.

2. A pharmaceutical composition comprising the compound of claim 1 and a pharmaceutical carrier.

3. A method for treating Gaucher's disease in a subject in need thereof, the method comprising administering to the subject the pharmaceutical composition of claim 2 to the subject.

4. A method for treating Parkinson's disease in a subject in need thereof, the method comprising administering to the subject the pharmaceutical composition of claim 2 to the subject.

5. The compound of claim 1 covalently attached to glucocerebrosidase.

6. A pharmaceutical composition comprising: (i) the compound of claim 1 covalently attached to glucocerebrosidase; and (ii) a pharmaceutical carrier.

7. A method for treating Gaucher's disease in a subject in need thereof, the method comprising administering to the subject the pharmaceutical composition of claim 6 to the subject.

8. A method for treating Parkinson's disease in a subject in need thereof, the method comprising administering to the subject the pharmaceutical composition of claim 6 to the subject.

9. A compound or a salt or solvate thereof having a formula:

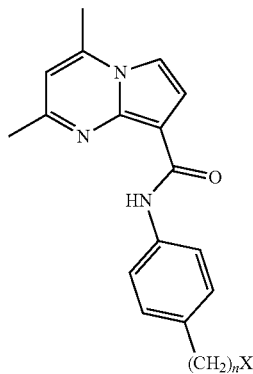

wherein:
n is 0-2; and
X is selected from the group consisting of:

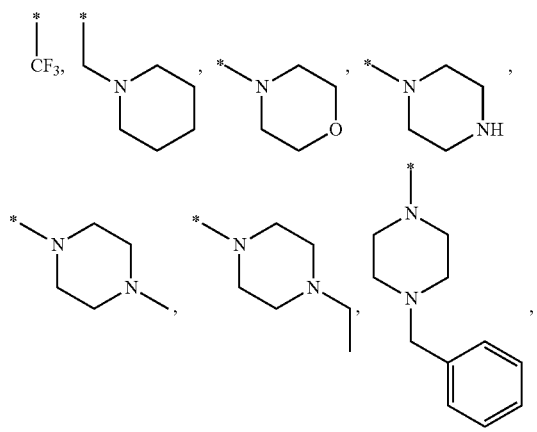

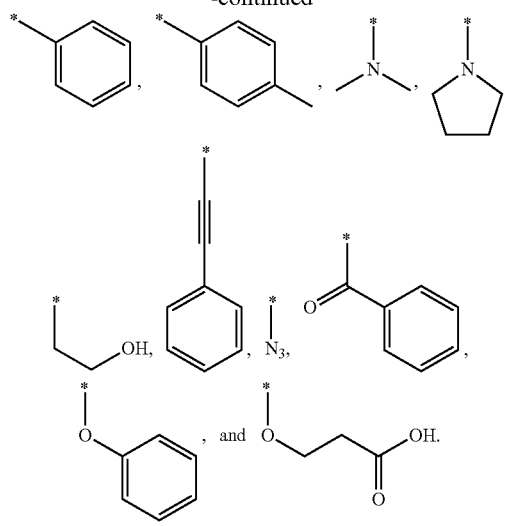

10. A pharmaceutical composition comprising the compound of claim 9 and a pharmaceutical carrier.

11. A method for treating Gaucher's disease in a subject in need thereof, the method comprising administering to the subject the pharmaceutical composition of claim 10 to the subject.

12. A method for treating Parkinson's disease in a subject in need thereof, the method comprising administering to the subject the pharmaceutical composition of claim 10 to the subject.

13. The compound of claim 9 covalently attached to glucocerebrosidase.

14. A pharmaceutical composition comprising: (i) the compound of claim 9 covalently attached to glucocerebrosidase; and (ii) a pharmaceutical carrier.

15. A method for treating Gaucher's disease in a subject in need thereof, the method comprising administering to the subject the pharmaceutical composition of claim 14 to the subject.

16. A method for treating Parkinson's disease in a subject in need thereof, the method comprising administering to the subject the pharmaceutical composition of claim 14 to the subject.

17. A compound having a formula selected from:

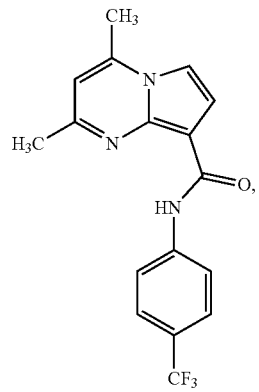

121
-continued
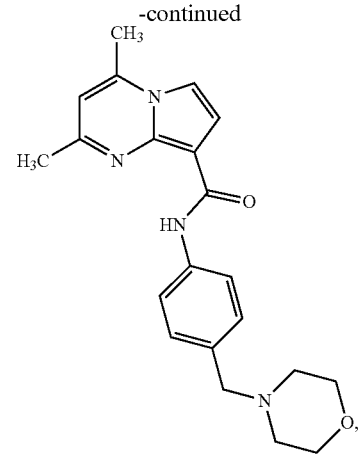
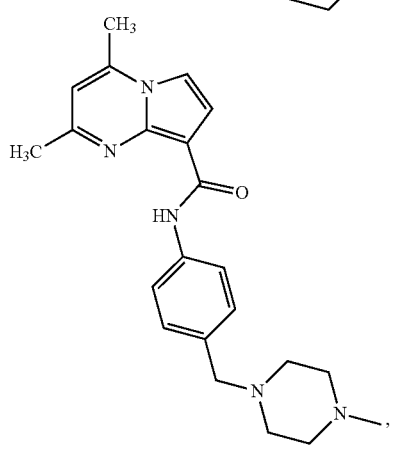
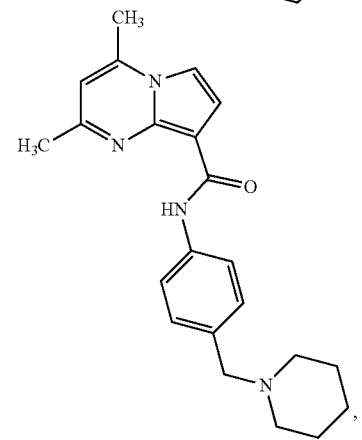
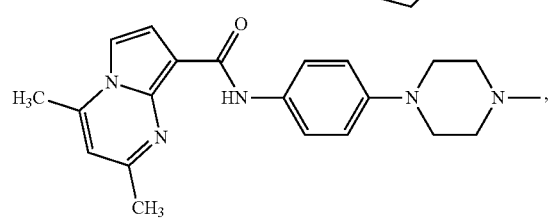
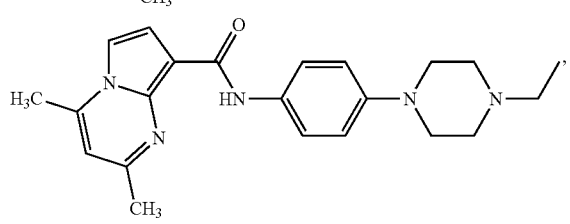
122
-continued
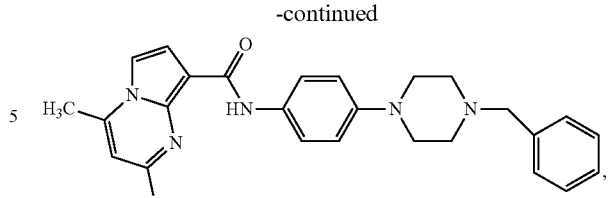
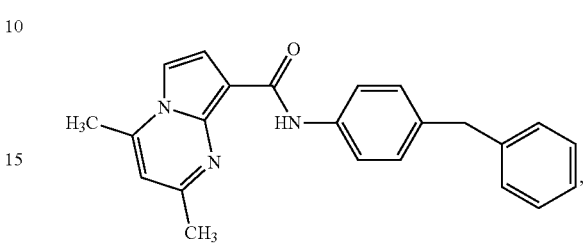
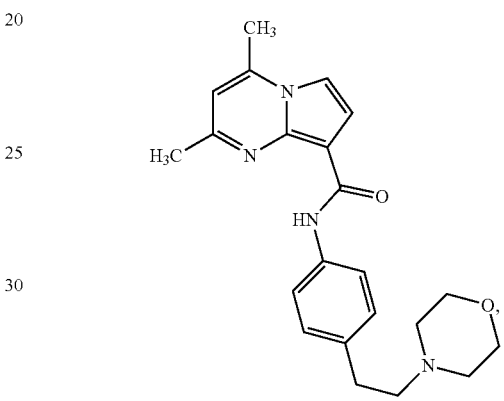
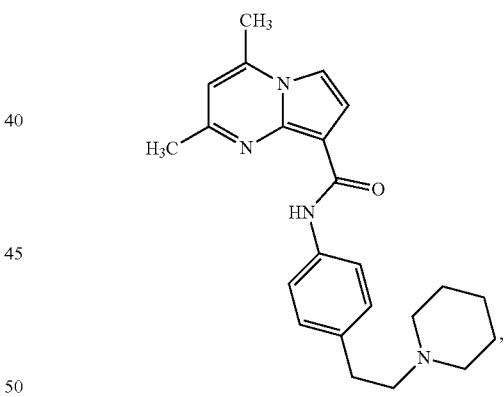
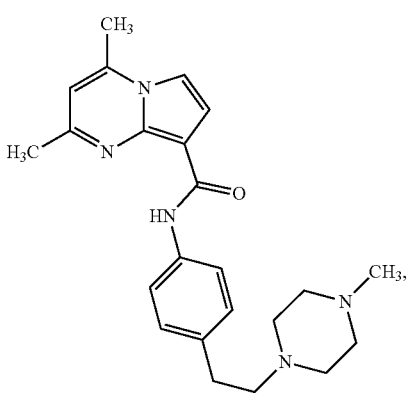

123
-continued
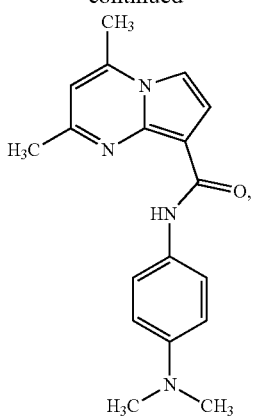
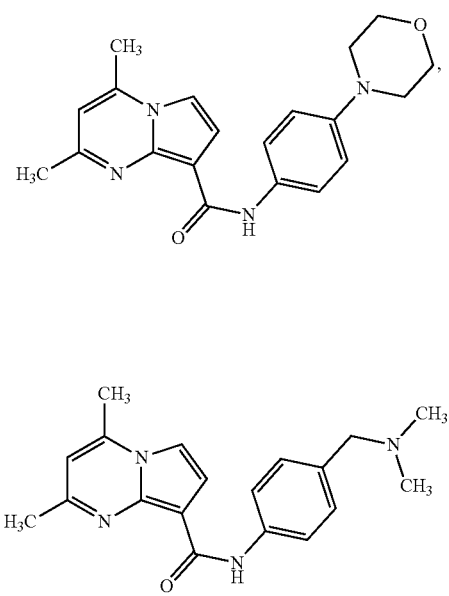
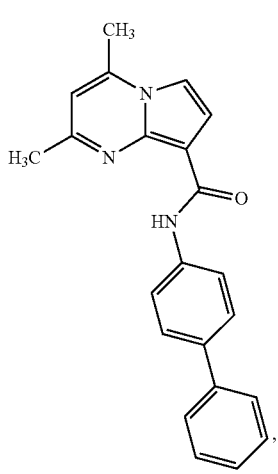
124
-continued
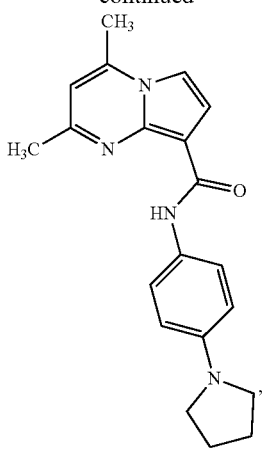
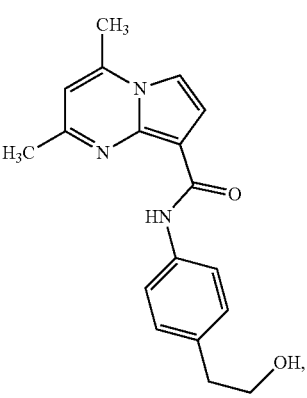
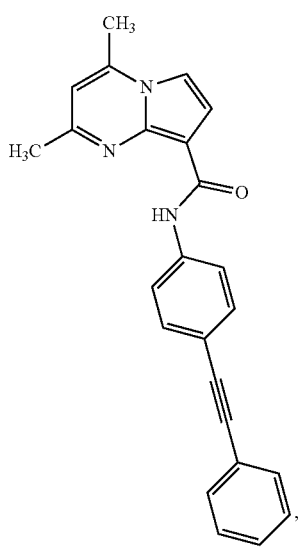

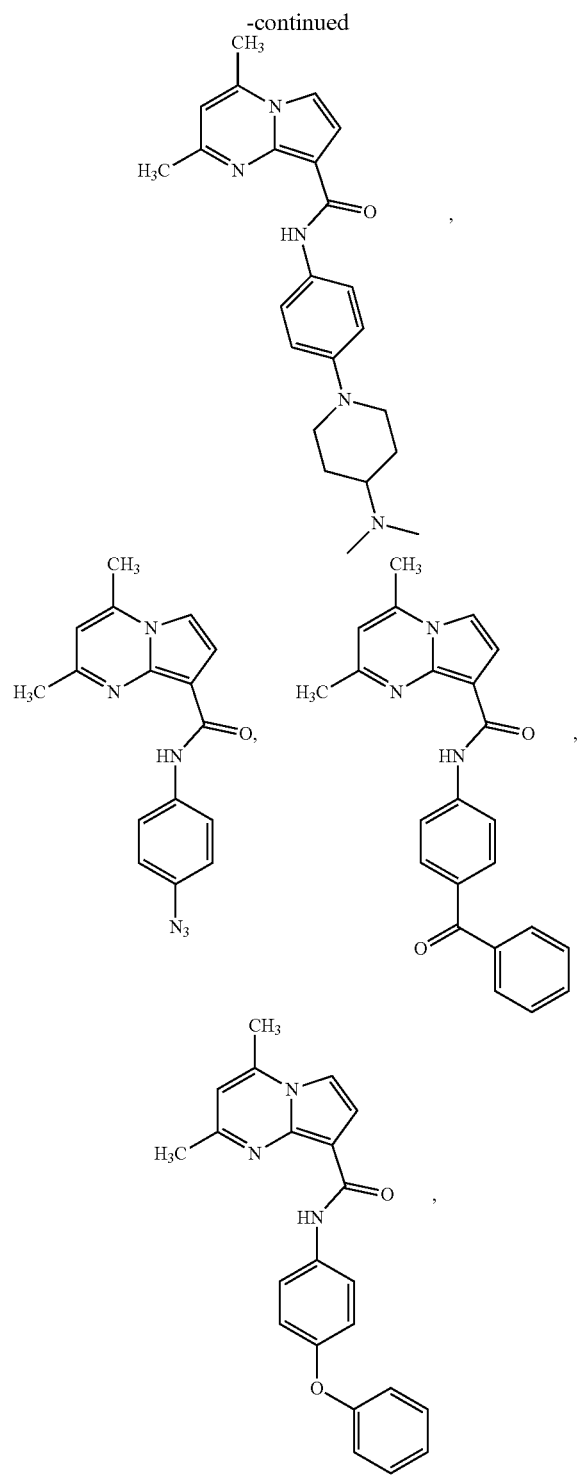
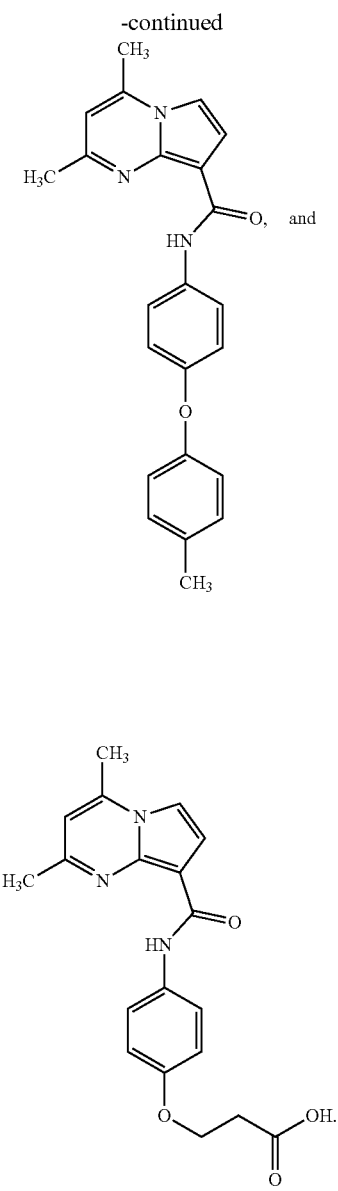
18. A pharmaceutical composition comprising the compound of claim 17 and a pharmaceutical carrier.
19. The compound of claim 17 covalently attached to glucocerebrosidase.
20. A pharmaceutical composition comprising: (i) the compound of claim 17 covalently attached to glucocerebrosidase; and (ii) a pharmaceutical carrier.
* * * * *